US010813825B2

(12) United States Patent
Schubert

(10) Patent No.: US 10,813,825 B2
(45) Date of Patent: Oct. 27, 2020

(54) COMPRESSION DEVICE

(71) Applicant: Portable Therapeutix, LLC, Houston, TX (US)

(72) Inventor: Shai Yehoshua Schubert, Brookline, MA (US)

(73) Assignee: Portable Therapeutix, LLC, Houston, TX (US)

( * ) Notice: Subject to any disclaimer, the term of this patent is extended or adjusted under 35 U.S.C. 154(b) by 742 days.

(21) Appl. No.: 14/321,805

(22) Filed: Jul. 1, 2014

(65) Prior Publication Data

US 2014/0316314 A1 Oct. 23, 2014

Related U.S. Application Data

(63) Continuation-in-part of application No. 13/523,632, filed on Jun. 14, 2012, now abandoned.
(Continued)

(51) Int. Cl.
*A61H 9/00* (2006.01)
*A61F 7/02* (2006.01)

(52) U.S. Cl.
CPC ......... *A61H 9/0078* (2013.01); *A61H 9/0092* (2013.01); *A61H 2201/0157* (2013.01); *A61H 2201/0214* (2013.01); *A61H 2201/0257* (2013.01); *A61H 2201/5015* (2013.01); *A61H 2201/5035* (2013.01);
(Continued)

(58) Field of Classification Search
CPC ...... A61H 9/00; A61H 9/0078; A61H 9/0092; A61F 7/00; A61F 2007/00; A61F 5/012; A61F 5/05816
See application file for complete search history.

(56) References Cited

U.S. PATENT DOCUMENTS 3,463,161 A * 8/1969 Andrassy .................. F25D 3/00 607/110
3,717,145 A * 2/1973 Berndt ...................... A61F 7/10 128/DIG. 20

(Continued)

FOREIGN PATENT DOCUMENTS

CA 2269440 A1 4/1998
JP 10-337313 A 12/1998

(Continued)

OTHER PUBLICATIONS

PCT Jan. 30, 2013 International Search Report and Written Opinion issued for International Application No. PCT/US2012/042510.

(Continued)

*Primary Examiner* — Justine R Yu
*Assistant Examiner* — Christopher E Miller
(74) *Attorney, Agent, or Firm* — Foley & Lardner LLP

(57) ABSTRACT

Apparatus and devices for intermittently and sequentially compressing a body site include a first segment cooperative with a fluid chamber, the fluid chamber adapted for inflation by fluid; and a second segment cooperative with the first segment, the second segment housing a temperature sensitive material, wherein the temperature sensitive material is uniquely compartmentalized in the second segment. Methods for using said apparatus and devices include site specific treatment to achieve a desired temperature of the underlying tissue.

38 Claims, 47 Drawing Sheets

Related U.S. Application Data

(60) Provisional application No. 61/841,567, filed on Jul. 1, 2013, provisional application No. 61/497,059, filed on Jun. 15, 2011, provisional application No. 61/497,050, filed on Jun. 14, 2011.

(52) U.S. Cl.
CPC .. *A61H 2201/5071* (2013.01); *A61H 2205/06* (2013.01); *A61H 2205/062* (2013.01); *A61H 2205/065* (2013.01); *A61H 2205/102* (2013.01); *A61H 2205/12* (2013.01)

(56) References Cited

U.S. PATENT DOCUMENTS 3,830,676 A * 8/1974 Elkins ........ A61F 7/02 156/289
3,901,225 A * 8/1975 Sconce ........ A61F 5/05816 128/DIG. 15
4,149,529 A * 4/1979 Copeland ........ A61H 9/0078 601/151
4,370,975 A 2/1983 Wright
4,462,224 A * 7/1984 Dunshee ........ A61F 7/106 62/530
4,527,565 A * 7/1985 Ellis ........ A61F 7/10 607/109
4,597,384 A * 7/1986 Whitney ........ A61F 13/085 128/DIG. 20
4,671,267 A 6/1987 Stout
5,072,875 A * 12/1991 Zacoi ........ A61F 7/02 607/104
5,074,285 A 12/1991 Wright
5,086,771 A * 2/1992 Molloy ........ A61F 7/10 128/892
5,097,829 A * 3/1992 Quisenberry ........ A61F 7/02 219/490
5,129,391 A * 7/1992 Brodsky ........ A61F 7/10 607/110
5,163,425 A * 11/1992 Nambu ........ A42B 1/008 607/110
5,172,689 A * 12/1992 Wright ........ A61F 7/10 602/2
5,230,335 A * 7/1993 Johnson, Jr. ........ A61F 7/08 607/104
5,339,541 A 8/1994 Owens
RE34,883 E * 3/1995 Grim ........ A61F 5/028 602/13
5,407,421 A * 4/1995 Goldsmith ........ A61F 5/012 128/882
5,409,500 A 4/1995 Dyrek
5,411,541 A * 5/1995 Bell ........ A61F 7/02 601/15
5,449,379 A * 9/1995 Hadtke ........ A61B 17/1325 606/203
5,456,701 A * 10/1995 Stout ........ A61F 7/02 165/46
RE35,113 E * 12/1995 Grim ........ A61F 5/0111 602/14
5,496,358 A * 3/1996 Rosenwald ........ A61F 5/0104 126/204
5,507,792 A * 4/1996 Mason ........ A61F 5/05816 601/15
5,643,336 A * 7/1997 Lopez-Claros ........ A61F 7/02 126/204
5,806,335 A * 9/1998 Herbert ........ A61F 7/10 607/114
5,865,841 A * 2/1999 Kolen ........ A61F 7/02 126/204
5,871,526 A * 2/1999 Gibbs ........ A61F 7/02 165/46
5,948,010 A * 9/1999 Adamec ........ A61F 7/02 607/108
6,113,626 A * 9/2000 Clifton ........ A61F 7/0097 607/104
6,117,164 A * 9/2000 Gildersleeve ........ A61F 7/02 607/108
6,149,674 A * 11/2000 Borders ........ A61F 7/007 607/96
6,203,510 B1 3/2001 Takeuchi et al.
6,238,427 B1 * 5/2001 Matta ........ A61F 7/02 607/104
6,290,662 B1 * 9/2001 Morris ........ A61H 9/0078 601/149
6,336,907 B1 * 1/2002 Dono ........ A47C 7/467 601/148
6,375,673 B1 * 4/2002 Clifton ........ A61G 7/0507 607/104
6,416,534 B1 * 7/2002 Montagnino ........ A61F 7/007 602/14
6,419,691 B1 * 7/2002 Hanner ........ A61F 7/02 607/108
6,500,200 B1 * 12/2002 Kushnir ........ A61F 7/02 165/46
6,942,015 B1 * 9/2005 Jenkins ........ A41D 13/005 165/104.14
7,264,630 B1 * 9/2007 Webb ........ A61F 7/02 128/898
7,846,141 B2 12/2010 Weston
8,444,581 B1 5/2013 Maxon-Maldonado et al.
8,485,995 B1 * 7/2013 Maxon-Maldonado ........ A61H 9/00 601/148
8,894,698 B2 * 11/2014 Gammons ........ A61F 7/02 607/104
9,510,994 B2 * 12/2016 Wilford ........ A61H 9/0078
9,615,967 B2 * 4/2017 Lowe ........ A61H 9/0021
2001/0034545 A1 * 10/2001 Elkins ........ A61F 7/02 607/108
2002/0042583 A1 * 4/2002 Barak ........ A61F 5/012 601/1
2003/0109910 A1 6/2003 Lachenbruch et al.
2003/0181990 A1 * 9/2003 Phillips ........ A61F 2/80 623/37
2005/0143797 A1 * 6/2005 Parish ........ A61F 5/34 607/104
2005/0256556 A1 * 11/2005 Schirrmacher ........ A61F 7/02 607/104
2006/0155350 A1 * 7/2006 Lu ........ A61F 7/10 607/114
2007/0049853 A1 * 3/2007 Adams ........ A61H 9/0078 601/151
2007/0118194 A1 * 5/2007 Mason ........ A61F 7/02 607/104
2007/0161932 A1 7/2007 Pick et al.
2008/0132976 A1 6/2008 Kane et al.
2008/0195012 A1 * 8/2008 Miros ........ A61F 5/0106 602/26
2009/0149925 A1 * 6/2009 MacDonald ........ A61F 7/034 607/96
2009/0260639 A1 10/2009 Hsu et al.
2009/0312681 A1 * 12/2009 McSpadden ........ A61F 5/0123 602/2
2009/0312823 A1 * 12/2009 Patience ........ A61F 7/007 607/104
2010/0081977 A1 * 4/2010 Vess ........ A61H 9/0092 602/13
2010/0137764 A1 * 6/2010 Eddy ........ A61H 9/0078 601/152
2010/0210982 A1 * 8/2010 Balachandran ........ A61F 7/0085 601/152
2011/0004133 A1 * 1/2011 Viner ........ A61F 7/10 602/14
2012/0172774 A1 * 7/2012 Lowe ........ A61F 7/02 602/13
2012/0185021 A1 * 7/2012 Johnson ........ F28F 3/12 607/104
2012/0245661 A1 * 9/2012 Mason ........ A61F 7/02 607/104

(56) References Cited

U.S. PATENT DOCUMENTS

| | | | | |
|---|---|---|---|---|
| 2012/0323152 | A1 | 12/2012 | Schubert | |
| 2013/0006335 | A1* | 1/2013 | Lowe | A61N 1/39 607/104 |
| 2013/0261712 | A1* | 10/2013 | Ebel | A61F 7/02 607/112 |

FOREIGN PATENT DOCUMENTS

| | | | |
|---|---|---|---|
| JP | 2002-065784 | A | 3/2002 |
| JP | 2005-143828 | A | 6/2005 |
| JP | 2010-082454 | A | 4/2010 |
| WO | WO-0198741 | A2 | 12/2001 |

OTHER PUBLICATIONS

CN Dec. 8, 2014 Office Action mailed in Chinese Patent Application No. 201280029076.6.

EP Mar. 27, 2015 Supplemental European Search Report issued in European Pat. App. No. 12801143.4.

EP Oct. 26, 2015 Response to Supplemental European Search Report with Amended Claims filed in European Pat. App. No. 12801143.4.

PCT Oct. 2, 2015 International Search Report and Written Opinion issued for International Application No. PCT/US2015/038236.

JP Jan. 12, 2016 Office Action mailed in Japanese Patent Application No. 2014-515999 (with English translation).

CN Aug. 30, 2016 Fourth Office Action mailed in Chinese Patent Application No. 201280029076.6 (with English translation).

EP Dec. 9, 2016 First Examination Report mailed in European Patent Application No. 12801143.4.

JP Nov. 8, 2016 Office Action / Decision to Refuse mailed in Japanese Patent Application No. 2014-515999 (with English translation).

CN Mar. 21, 2017 Fifth Office Action mailed in Chinese Patent Application No. 201280029076.6 (with English translation).

EP Jun. 15, 2017 Response to First Examination Report dated Dec. 9, 2016 in European Patent Application No. 12801143.4.

US Mar. 11, 2015 Non-Final Office Action mailed in U.S. Appl. No. 13/523632, filed Jun. 14, 2012.

US Jun. 8, 2015 Amendment and Response to Office Action dated Mar. 11, 2015, for U.S. Appl. No. 13/523,632, filed Jun. 14, 2012.

US Sep. 4, 2015 Final Office Action mailed in U.S. Appl. No. 13/523,632, filed Jun. 14, 2012.

US Oct. 27, 2015 Applicant Initiated Interview Request Form with Proposed Claim Amendments for U.S. Appl. No. 13/523,632, filed Jun. 14, 2012.

US Nov. 27, 2015 Office Communication—Applicant-Initiated Interview Summary mailed in U.S. Appl. No. 13/523,632, filed Jun. 14, 2012.

US Jan. 4, 2016 Amendment and Response to Final Office Action dated Sep. 4, 2015; Petition for One-Month Extension of Time; and Request for Continued Examination for U.S. Appl. No. 13/523,632, filed Jun. 14, 2012.

US Feb. 10, 2016 Non-Final Office Action mailed in U.S. Appl. No. 13/523,632, filed Jun. 14, 2012.

US May 10, 2016 Amendment and Response to Office Action dated Feb. 10, 2016 for U.S. Appl. No. 13/523,632, filed Jun. 14, 2012.

US Jun. 28, 2016 Final Office Action mailed in U.S. Appl. No. 13/523,632, filed Jun. 14, 2012.

US Sep. 27, 2016 Applicant Initiated Interview Request Form with Proposed Claim Amendments for U.S. Appl. No. 13/523,632, filed Jun. 14, 2012.

US Oct. 5, 2016 Office Communication—Applicant-Initiated Interview Summary mailed in U.S. Appl. No. 13/523,632, filed Jun. 14, 2012.

US Oct. 19, 2016 Amendment and Response to Final Office Action dated Jun. 28, 2016; Petition for One-Month Extension of Time; and Second Request for Continued Examination for U.S. Appl. No. 13/523,632, filed Jun. 14, 2012.

US Nov. 15, 2016 Non-Final Office Action mailed in U.S. Appl. No. 13/523,632, filed Jun. 14, 2012.

US Feb. 28, 2017 Amendment and Response to Office Action dated Nov. 15, 2016; and Petition for One-Month Extension of Time for U.S. Appl. No. 13/523,632, filed Jun. 14, 2012.

US Jul. 11, 2017 Non-Final Office Action mailed in U.S. Appl. No. 13/523,632, filed Jun. 14, 2012.

US Jan. 25, 2018 Amendment and Response to Office Action dated Jul. 11, 2017 and to Office Communication dated Oct. 27, 2017 for U.S. Appl. No. 13/523,632, filed Jun. 14, 2012.

US Mar. 5, 2018 Final Office Action mailed in U.S. Appl. No. 13/523,632, filed Jun. 14, 2012.

* cited by examiner

COMPRESSION DEVICE

CROSS-REFERENCE TO RELATED APPLICATIONS

This application is a continuation-in-part application of U.S. patent application Ser. No. 13/523,632, filed Jun. 14, 2012, which claims the benefit of U.S. Provisional Patent Application No. 61/497,050 filed Jun. 14, 2011, and U.S. Provisional Patent Application No. 61/497,059 filed Jun. 15, 2011. This application also claims the benefit of U.S. Provisional Patent Application No. 61/841,567 filed Jul. 1, 2013. All of said priority claimed applications are hereby incorporated by reference in their entirety.

BACKGROUND

The invention described relates generally to compression devices, including those used for treatment of a body site of interest in a person.

Compression devices have been used to apply pressure to a part of the body. The devices can apply pressure sequentially or simultaneously. These devices are often combined with other modes of therapy to treat a site of interest, such as with a cold therapy. Complications with some devices have arisen because of the type of compression and/or the placement or positioning of the device. There remains a need for compression devices that provide proper placement, offer site specific compression with high and reproducible effectiveness, may be optimally temperature controlled and are also portable.

SUMMARY

Described herein are improved devices for intermittently and sequentially compressing a site specific area of the body and methods for using said devices.

In one form is an apparatus configured for placement on a person at a specific site of the body, the apparatus comprising a first segment cooperative with a fluid chamber, the fluid chamber adapted for inflation by fluid from a fluid source; and a second segment cooperative with the first segment, the second segment housing a temperature sensitive material, wherein the temperature sensitive material is compartmentalized in the second segment in a manner that prevents migration and/or is not equally distributed in the second segment. The temperature sensitive material may be compartmentalized in a plurality of chambers in the second chamber. The compartments in the second chamber may be the same as and align with one or more chambers in the fluid chamber. The temperature sensitive material may include a chemical indicator. The temperature sensitive material may be a hydrogel. The first segment may be shaped for positioning about only a portion of a joint. The first segment may be shaped for positioning about a front portion of a knee. The apparatus may further comprise one or more fasteners cooperative with and extending from the first segment for securing the first and second segments about the site of the body. The fluid introduced to the fluid chamber may be controlled by a predefined algorithm. The fluid introduced to the fluid chamber is controlled by a controller having one or more predefined settings. A control unit associate with the apparatus may control operation of the apparatus, the control unit selected from the group consisting of external device, internal controller and combinations thereof. The apparatus may further comprise one or more ergonomically positioned fasteners cooperative with and extending from the first segment for securing the first and second segments about the body site without compressing one or more sensitive regions near the body site and/or preventing migration of the fasteners from their initial position. The first segment may be selectively shaped for positioning about only a portion of a joint. The second segment may be further shaped prior to its cooperation with the first segment (from a first shape to a second shape). Inflation of the fluid chamber may be performed by a portable unit adapted for and coupled with the first segment. The fluid chamber may be contained within the first segment. The fluid chamber and the second segment may be of a similar size in at least two dimensions. The fluid chamber may be filled intermittently whereby intermittent filling comprises a period of inflation and a period of deflation, wherein the period of inflation is not the same as the period of deflation. The fluid chamber may be filled intermittently whereby intermittent filling comprises a period of inflation and a period of deflation, wherein the period of inflation is the same as the period of deflation.

In other forms, described herein is a therapy system for use and placement on a body site of a person, the system comprising: a first segment comprising a fluid chamber adapted for inflation; a second segment comprising a temperature sensitive material, wherein the temperature sensitive material is compartmentalized in the second segment to prevent migration, and wherein, the first and second segments are removably coupled to one another; a fluid source fluidly coupled to the fluid chamber; and one or more extending members for coupling to and extending from the first segment, the one or more extending member for securing the first segment about the body site, wherein at least a portion of the one or more extending members are shaped curvilinearly to prevent their migration from an initial position. The inflation may be intermittent. Inflation of the fluid chamber provides compression to the body site and the total time for compression may be about thirty minutes or less. Inflation of the fluid chamber may provide compression to all of the temperature sensitive material in a sequential manner. The fluid chamber may be contained within the first segment. The fluid chamber may overlap substantially all of the temperature sensitive material to provide compression to substantially all of the temperature sensitive material. The second segment may be removably secured to the first segment. The first and second segments may be of a similar size in at least two dimensions. The system typically further comprises a control unit having one or more predefined algorithms for achieving a desired temperature on the body site by adjusting one or both of a fluid pressure and time of inflation associated with the fluid chamber.

In still other forms is a method of introducing a therapy system on a person at a body site comprising: providing an apparatus to only the body site, the apparatus comprising: at least a first segment cooperative with a fluid chamber, the fluid chamber adapted for intermittent inflation by a fluid; a fluid source fluidly coupled to the fluid chamber to introduce the fluid to the fluid chamber; and one or more extending members ergonomically positioned for coupling to and extending from the first segment and for securing the first segment about the body site without migrating from an initial position and/or one or more extending members ergonomically positioned for coupling to and extending from the first segment and for securing the first segment about the body site without compressing one or more sensitive regions near the body site. The method further comprises introducing fluid intermittently for a defined period of time to the fluid chamber thereby intermittently compressing only the body site while maintaining the one or more extending members in their initial position. The method may include coupling a temperature sensitive material with the first segment. The fluid may be introduced for about thirty minutes or less. The fluid chamber may be compartmentalized introducing fluid sequentially and intermittently to the body site, wherein the sequential compression is from a distal portion of the body site to a proximal portion of the body site.

Still further is provided an apparatus for compressing at a site in need thereof, the apparatus comprising: a segment having a body with a distal end and a proximal end, an interior space within the body, an inlet located at the distal end for access into the interior space, and one or more extending regions for securing said body at the site, the segment further comprising a shape when formed that is ergonomic for the site; an inflatable bladder positioned within the interior space of the body, having a fluid port at a distal end; and a leakproof element containing at least a temperature sensitive material, the leakproof element having coupling elements for detaching and attaching to a portion of the body of the segment. The inflatable bladder may be compartmentalized. The leakproof element may be compartmentalized. The inflatable bladder may be compartmentalized with seams formed between compartments and may comprise one or more filler materials positioned where there is a gap in the seam. The inflatable element may be coupled to a source providing fluid to the inflatable element. The inflatable element may be coupled to a source providing fluid to the inflatable element, the fluid introduced in cycles that deflate and inflate the inflatable element over a period of time. The extensions are secured by one or more securing elements. The extensions are secured by one or more attachable and detachable securing elements and when secured help prevent movement of the device during operation. The apparatus may further comprise a portable fluid source for inflating the inflatable bladder. The fluid port of the inflatable bladder exits the inlet of the segment. The inflatable bladder and the leakproof element may be approximately the same overall size with respect to a front view of each. The inflatable bladder may be of a larger size than the leakproof element with respect to a front view of each. The inflatable bladder and the leakproof element may comprise the same number of compartments, and the compartments of the inflatable bladder are cooperative with the compartments of the leakproof element. The inflatable bladder inflates from the distal end to a proximal end.

In further embodiments, described herein is method of providing an apparatus for compressing at a site in need thereof, the method comprising: providing a segment having a body with a distal end and a proximal end, an interior space within the body, an inlet located at the distal end for access into the interior space, and one or more extending regions; positioning an inflatable bladder in the interior space of the body with a fluid port extending from the inflatable bladder exiting the inlet of the segment; enclosing the inflatable bladder by securing the body along the body's periphery while the inflatable bladder remains within the interior space of the body; and attaching a leakproof element to an exterior portion of the body so that the leakproof element is cooperative with the inflatable bladder. The leakproof element is detachable from the body. Enclosing of the inflatable body inflatable body may be reversible, to remove the inflatable body when damaged or desired.

BRIEF DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

DESCRIPTION

Figure 1A:
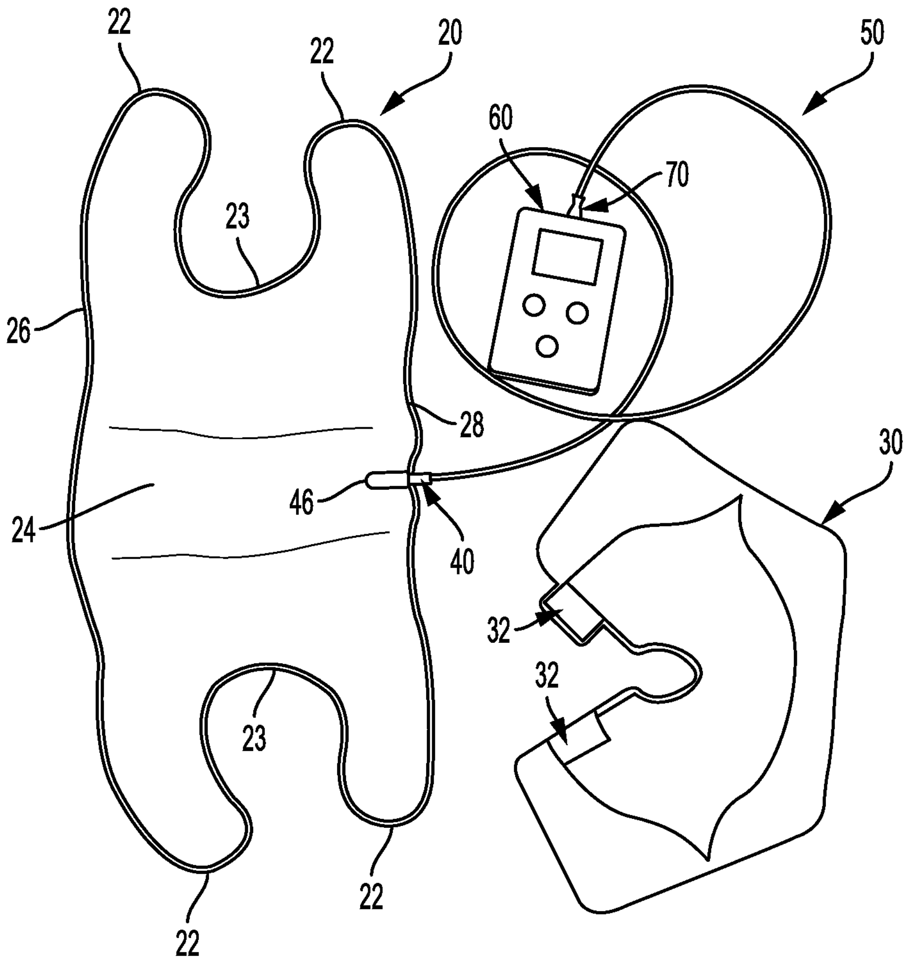
FIG. 1A depicts a representative device with a view of one of its outwardly facing surfaces and accompanying components as described herein.

In the description which follows like parts are marked throughout the specification and drawing with the same reference numerals respectively. The drawing figures are not necessarily to scale and certain features may be shown in generalized or schematic form in the interest of clarity and conciseness or for informational purposes.

Described herein are compression devices and methods of operation and use for compression treatment of one or more body sites or anatomic structures. The compression treatment may be for an acute injury, chronic injury, after surgery or recovery from other injury, for pain or inflammation, for use after exercise, or to prevent injury or worsening of an existing condition to the one or more body sites. The device promotes sequential compression of a fluid within the device in a direction towards the heart when the device is positioned on or about the body site. Compression is intermittent, generally applied in a predetermined fashion upon proper placement of the device and performed with sequential movement and/or distribution of the fluid (e.g., gas, liquid, etc.) on or about the body site. Fluid movement follows a predefined algorithm as further described herein; generally fluid movement is in a direction towards the heart, hence from a more distal location to a more proximal location. The device itself may be worn while a person is stationary or in motion. In many embodiments, the device includes a temperature adjustable component or temperature sensitive component, which, when combined with the compression and with a pre-defined algorithm, provides a controlled environment for efficacious treatment on or about the body site. Various components of the device may be reusable, washable, and/or disposable.

Referring to FIG. 1A, a representative compression device is shown comprising a first segment 20 and a second segment 30. Either or both the first and second segments may be transparent, partially transparent, opaque or combinations thereof. When including the second segment, the first and second segments are cooperative with one another. Cooperation may include a securement or fitting of the first and second segment by one or a number of means for securing 34, including but not limited to adhesive fitting, mechanical fitting, and/or chemical fitting. Suitable examples include fastening with one or more securing elements, such as but not limited to clips, buttons, hooks, magnets, ties, tabs, buckles, snaps, hook and loop, Velcro, adhesive, by sewing and any combination thereof. Other means for securing are within the understanding of one of skill in the relevant art. Representative examples of means for securing or securing elements 34 are depicted at least in FIGS. 1F, 1G, 4C, 5C, and 6C, as well as FIGS. 31-36. The cooperation is, in one or more embodiments, provided at or near the periphery of the segments and does not require, though it may include, securement around the entire periphery; securement may be only at various specific locations between the first and second segments. The cooperation may also include a pocket or housing on the first segment into which all or a portion of the second segment is positioned.

FIG. 1A further illustrates a connecting element 40 adapted for providing a releasable connection between tubing 50 and the device. While connecting element 40 is shown to provide said connection between the tubing and the first segment 20, connecting element 40 may also or alternatively be located to provide a connection between the tubing and the second segment 30. As depicted, connecting element 40 includes a port for providing a fluid connection between tubing 50 and the interior of first segment 20 (and may also include though not shown a port for providing a fluid connection between tubing 50 and/or the interior of second segment 30). The fluid connection to the interior of the first segment 20 is provided by a receiver or an inlet through a wall of first segment 20, so that the connecting element 40 cooperates with a fill port associated with a chamber of a filling element or bladder that is, in some embodiments, fitted or configured in the interior space of first segment 20. The fill port is cooperative with connecting element 40 allowing fluid entry to the chamber (not shown in FIG. 1A) housed in the interior space of first segment 20. The fill port (of the filling element) and the inlet or receiver of the first segment are generally located at or near a distal end of the device when the device is positioned for use. Generally, the location of the fill port and inlet are closer to the distal end than to a mid-section of the device, the mid-section including a line between the proximal end and the distal end of the device, said distal and proximal ends defining the ends of the device when the device is positioned for use. In some embodiments the fill port and inlet are positioned in a location between the mid-section and the distal end of the device, said distal and proximal ends defining the ends of the device when the device is positioned for use. In some embodiments, the fill port and the inlet are positioned in some region between the mid-section and the distal end of the device, said distal and proximal ends defining the ends of the device when the device is positioned for use. Connecting element 70 provides a releasable connection between the tubing and source 60. Connecting element 70 also includes a port for providing a fluid connection between tubing 50 and source 60.

The source may be portable or may be in the form of a machine that is less portable or is fixed. In FIG. 1A, a portable source is shown. In one or more embodiments, a portable source may be about or less than 8 inches in its longest length. The source, whether portable, less portable or fixed in some location, provides fluid, via the tubing, ports and connecting means, to the first segment (when connected to the filling element or bladder segment) and/or provides fluid, via the tubing, ports and connecting means, to the second segment (when connected to the second segment). The fluid is generally pressurized (e.g., by way of a pump that fluidly communicates with the device by battery power or other power source). The source may include a controller (e.g., microprocessor) that monitors and/or adjusts pressure and/or temperature. In some embodiments, the source is coupled to a pressure sensor (e.g., for monitoring fluid pressure in the device), a temperature sensor (e.g., for monitoring temperature at a body site), and/or a sensor that measures impedance (e.g., for monitoring impedance at a body site). The source may further include a detachable cover. In addition, the source may also include an analog or digital readout and/or an associated control panel (e.g., with manually or remotely activated switches). The source may further comprise one or more safety features that allow the pump to stop or reduce its pressure when a particular pressure is reached; the safety feature may be coupled to an alarm, a warning light and various combinations thereof. As an example, a source includes a controller operably connected to a compressor and valve mechanism (e.g., solenoid valve), each of which are mounted to a base (e.g., manifold), and a pressure sensor operable with a safety (e.g., valve) mechanism for releasing pressure should pressure become greater than a maximum pressure set for the device. As another example, a source includes a controller operable with a pump, a valve mechanism (e.g., solenoid valve), pressure gauge, muffler and exhaust or release mechanism (e.g., mechanical blow valve or other active or passive mechanism), each of which are operable with the inlet tubing communicating with the pump and bladder. In this embodiment, the pressure gauge is in operable communication with the solenoid valve (regarding opening and pressure release) and with the pump (regarding starting and stopping the pump) and the release mechanism is in operable communication with the bladder as a passive safety mechanism to release pressure should it become greater than a maximum pressure set for the device.

Figure 17A:
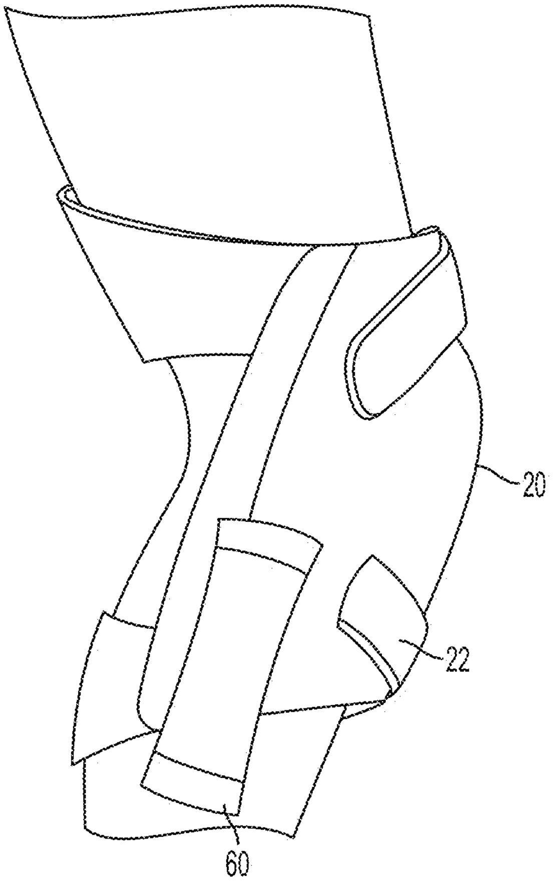
FIG. 17A depicts another representative device described herein with a portable source, the source shown in plan view is depicted in FIG. 17B.
Figure 17B:
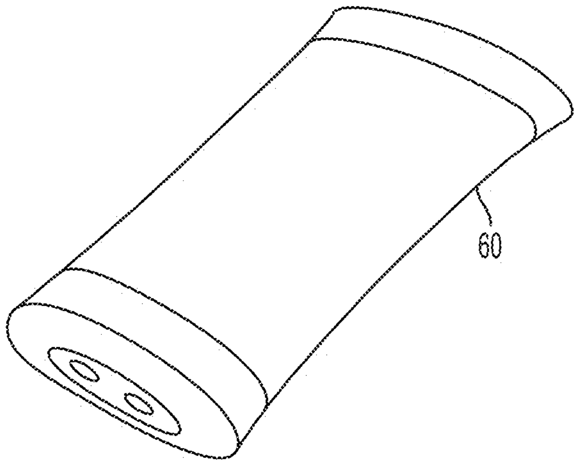
Figure 18A:
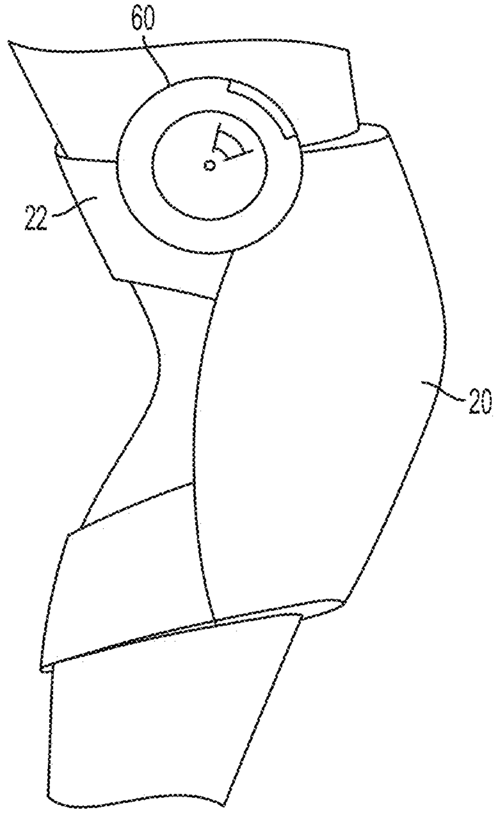
FIG. 18A depicts another representative device described herein with a portable source, the source shown in plan view (FIG. 18B) and in top view (FIG. 18C) is also depicted.
Figure 18B:
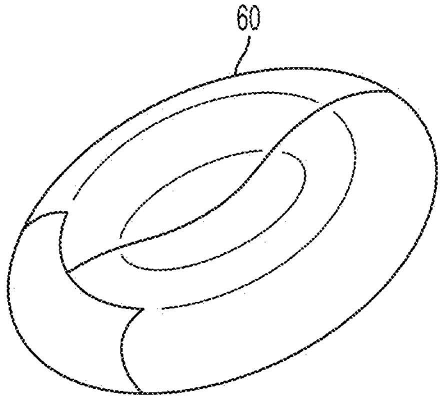
Figure 18C:
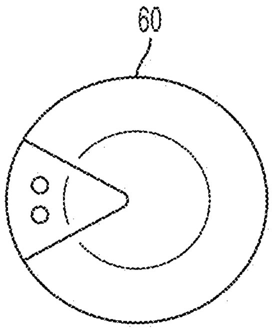
Figure 19A:
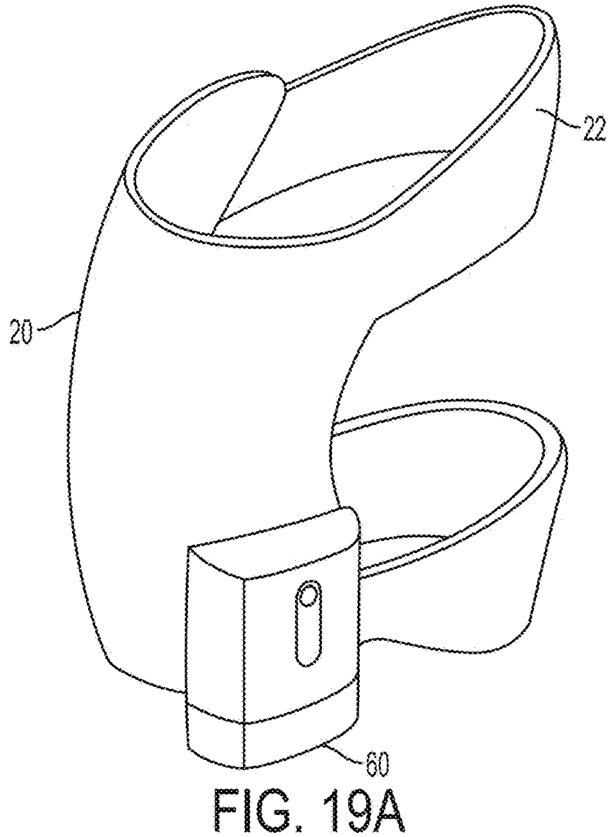
FIGS. 19A and 19B depict still another representative device with a portable source shown in plan view and side view, respectively.
Figure 19B:
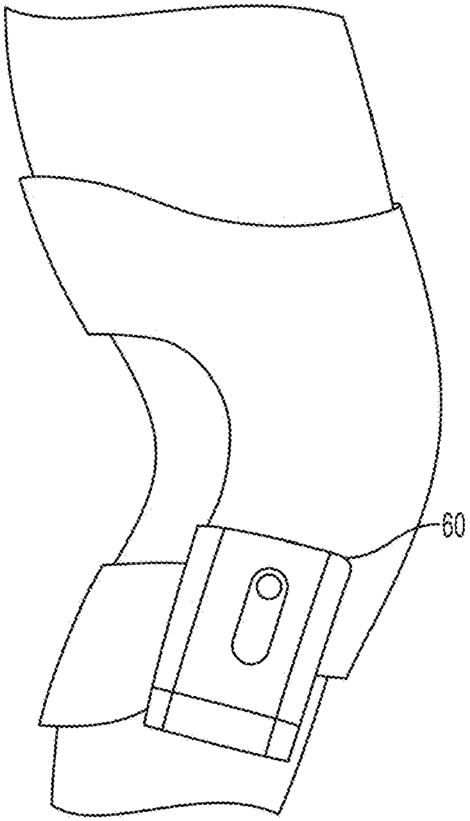

In one or more embodiments, the source is compact and may be removable, or may be permanently positioned on the exterior facing surface of the first segment. Representative examples are depicted in FIGS. 17, 18 and 19. Thus, the source may, in some embodiments, be coupled to and/or be detachable from the device. For portability, the source may include a portable power source (e.g., battery that is solar, electrical or nonelectrical, or may be non-battery powered) supplying power to the source components. The source may also include an indicator for battery charge level. When desired, one or more source components may be rechargeable and/or disposable.

First segment 20 will typically include a body 24, opposing lateral sides 23, a proximal portion 26, which will include but is not limited to a proximal side or edge more proximal to the heart and a distal portion 28, which will include but is not limited to a distal side or edge more distal to the heart. The distal and proximal portions can be said to be defined in view of the positioning of the device when in use. The distal portion and end generally defining said regions distal from a mid-section or mid region of the device, which includes a mid-line between the distal end and the proximal end when the device is positioned for use. The proximal portion and end generally include said regions proximal to a mid-section or mid region of the device, which includes a mid-line between the distal end and the proximal end when the device is positioned for use. Generally, connecting element 40, when positioned to couple with the fill port, will be placed at or near distal portion 28. Distal portion 28 may be near the distal end or edge of the device. In one or more embodiments the port for fluid entry that passes into the interior of the first segment is not at the distal end or edge but may be in close proximity to the distal end or edge, and in a region closer to the distal end or edge than to the mid-section of the device, when the device is positioned for use. The receiver of the first segment may be sized to allow only the fill port to pass there through. The receiver of the fill port may also be sized larger than the outer cross-sectional diameter of the fill port. Several representative embodiments showing representative configurations for the first segment are illustrated in FIGS. 2-19, 31A, 32A, 33A, 34A, 35A and 36A. Said embodiments illustrate that said first segment may include a shape that matches the anatomic shape of the portion of the body on which it will be positioned or includes features, such as cut-outs, seams, darts, indentations, flaps, tucks, folds, creases, ribbings, and other means or materials for making the anatomic shapes with the first segment.

Figure 4A:
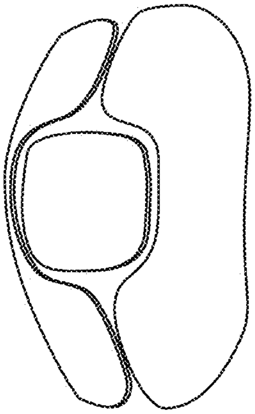
FIGS. 4A-4C depict further representative first segments with detachable second segments described herein.
Figure 4B:
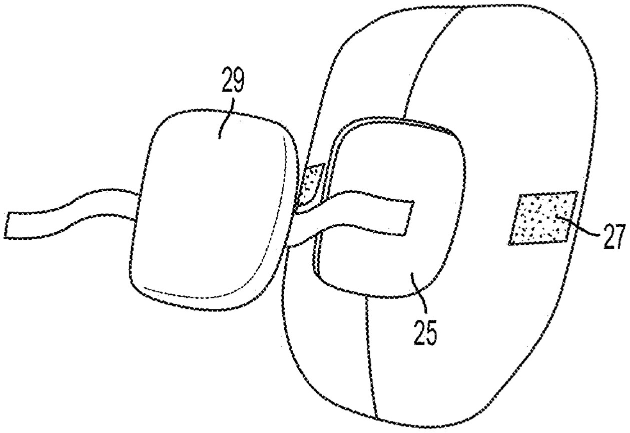
Figure 4C:
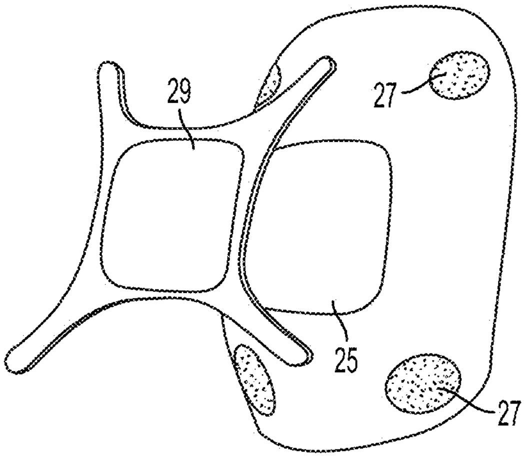
Figure 4D:
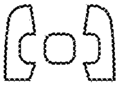
FIG. 4D depicts a front view of the first and second segments of FIG. 4A.
Figure 5A:
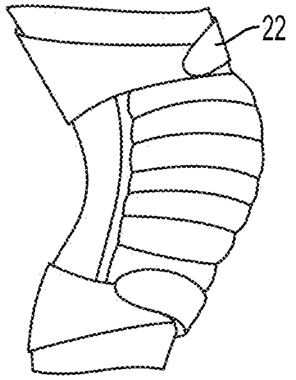
FIGS. 5A and 5B depict a side view and plan view, respectively, of a representative device described herein.
Figure 5B:
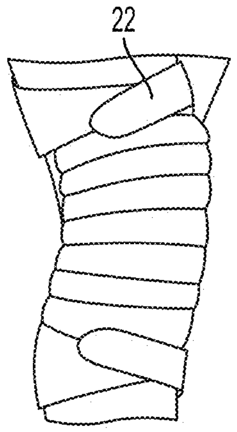
Figure 5C:
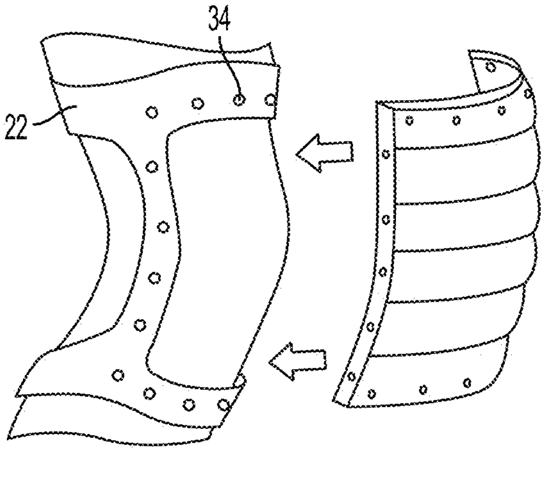
FIG. 5C depicts another representative first segment with a detachable second segment described herein.
Figure 6A:
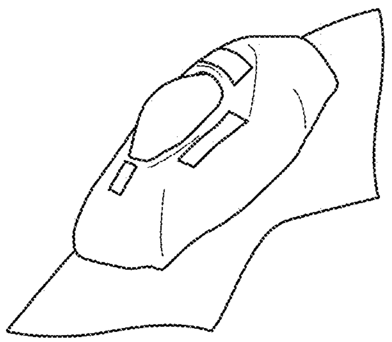
FIGS. 6A-6C depict various photographs of a further representative device without the second segment (6A), with the second segment on cooperation with the first segment (6B) and with the detached second segment, as described herein.
Figure 6B:
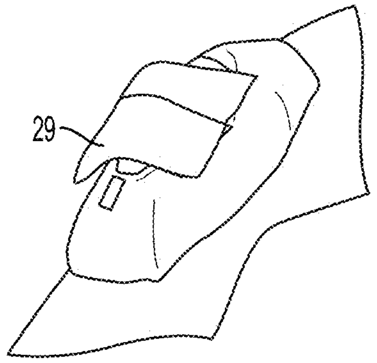
Figure 6C:
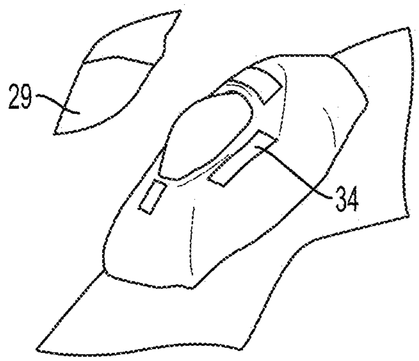
Figure 7B:
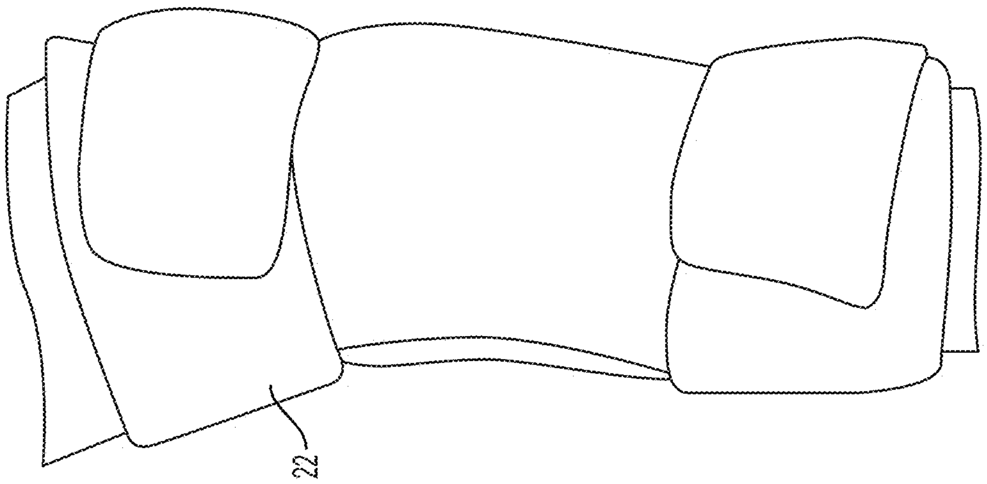
FIGS. 7A and 7B depict views of a representative device described herein in place on the body and positioned in flexion and in extension, respectively.
Figure 7A:
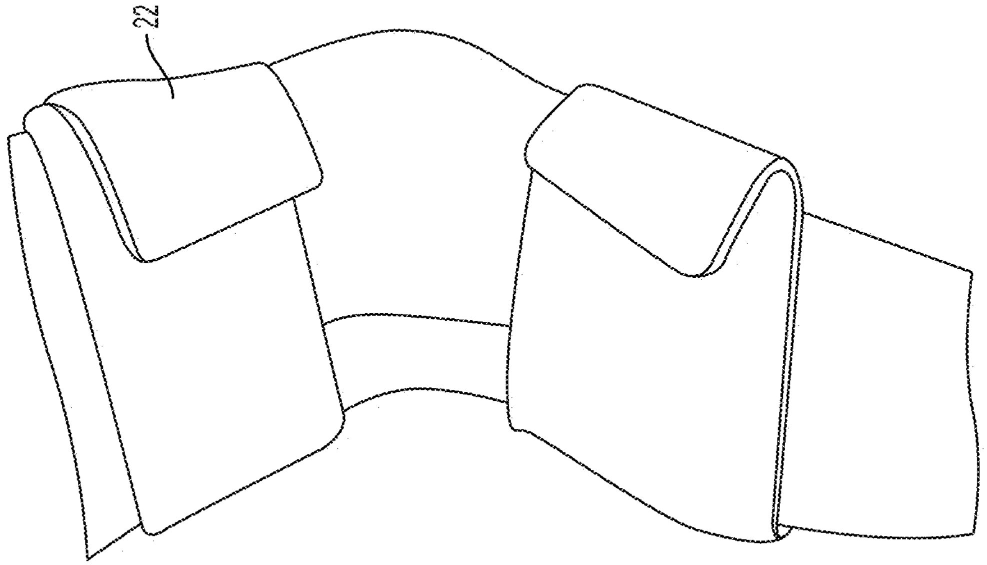
Figure 8B:
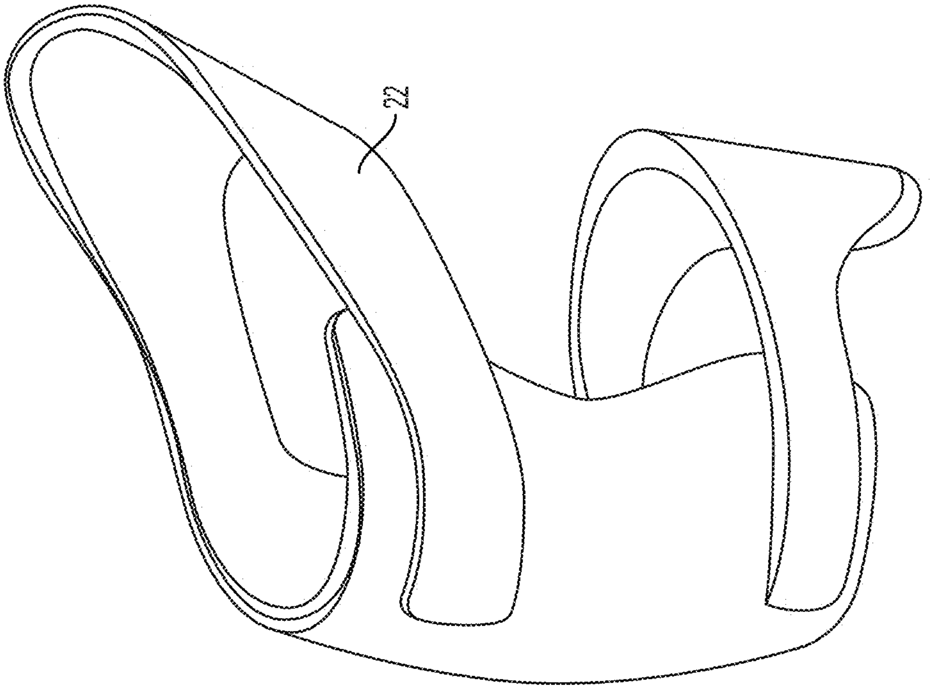
FIGS. 8A and 8B depict views of another representative device described herein in place on the body and positioned in flexion and in extension, respectively.
Figure 8A:
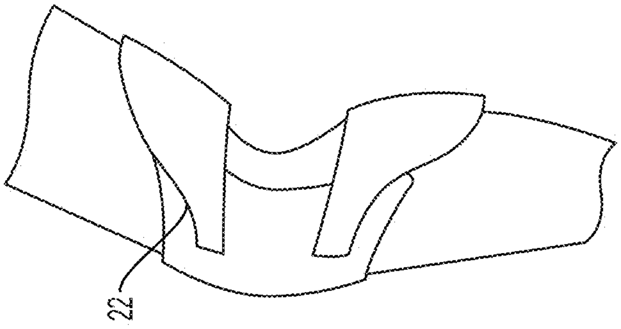
Figure 9B:
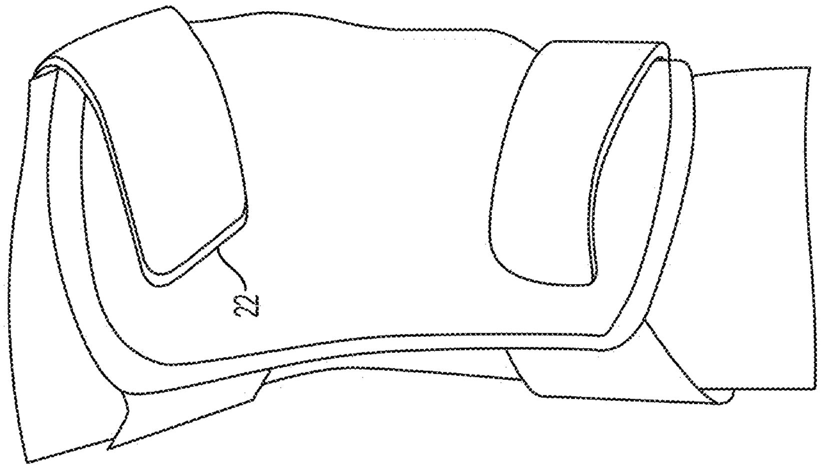
FIGS. 9A and 9B depict views a further representative device described herein in place on the body and positioned in flexion and in extension, respectively.
Figure 9A:
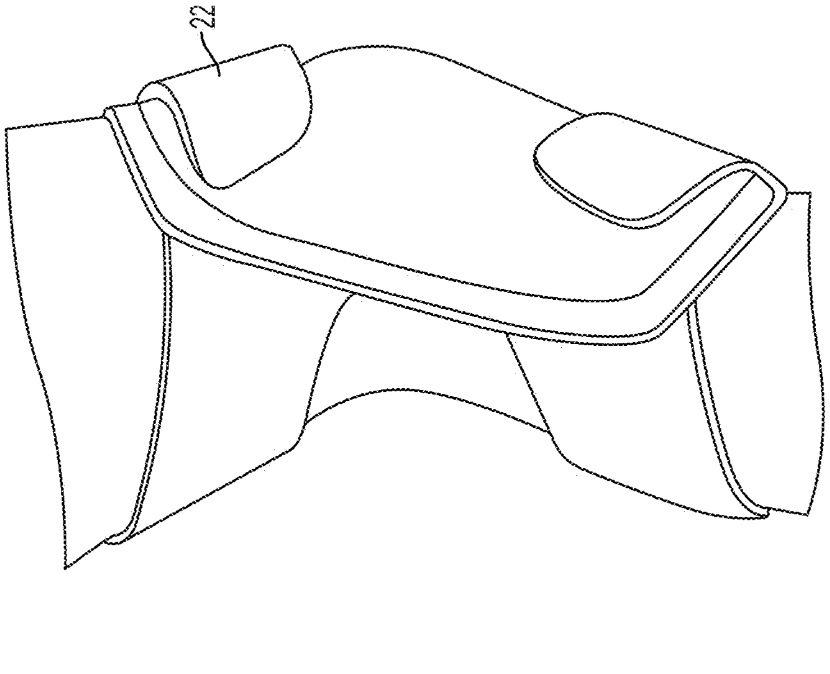
Figure 10B:
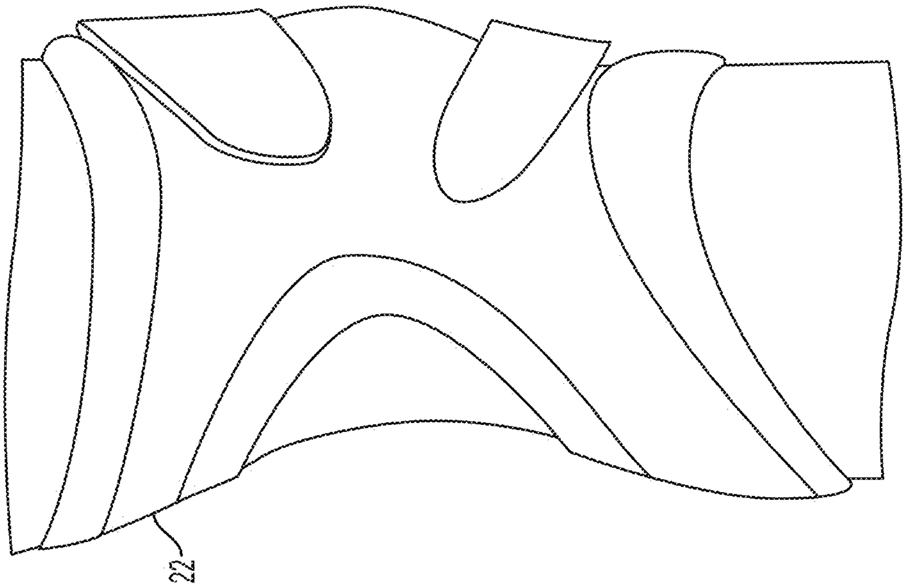
FIGS. 10A and 10B depict views of still another representative device described herein in place on the body and positioned in flexion and in extension, respectively.
Figure 10A:
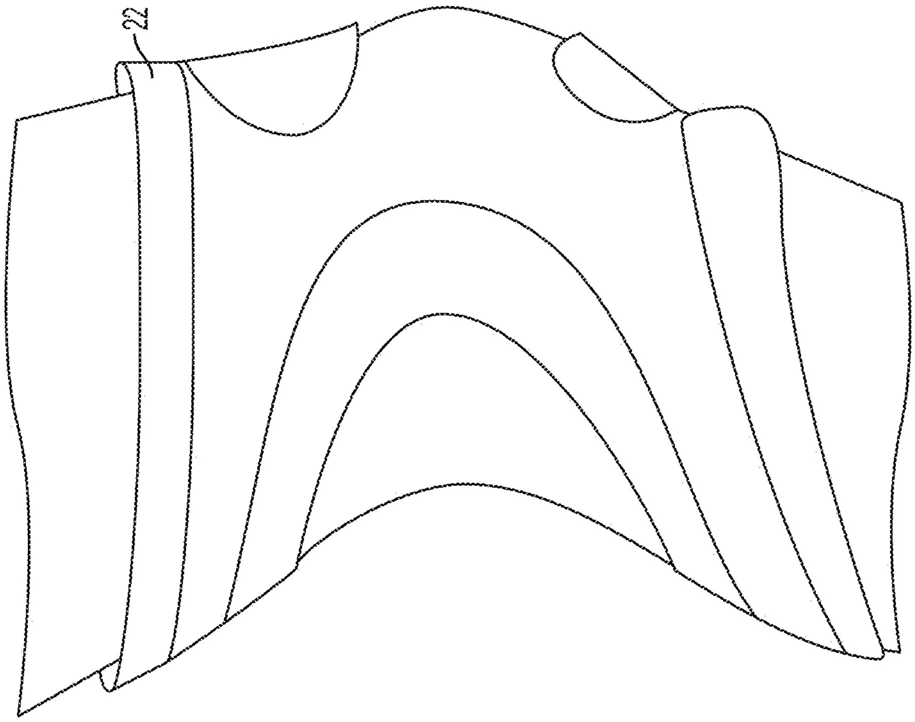
Figure 11B:
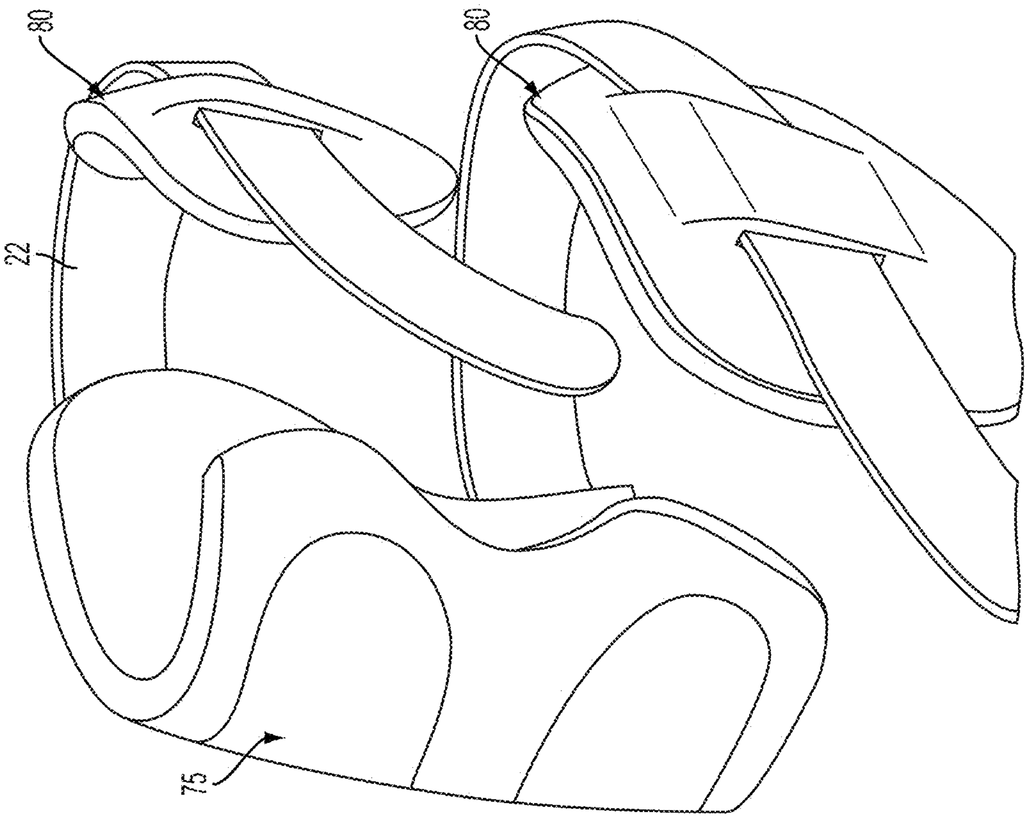
FIGS. 11A and 11B depict views of yet another representative device described herein, showing placement on the body and positioned in flexion (11A) or not on the body (11B).
Figure 11A:
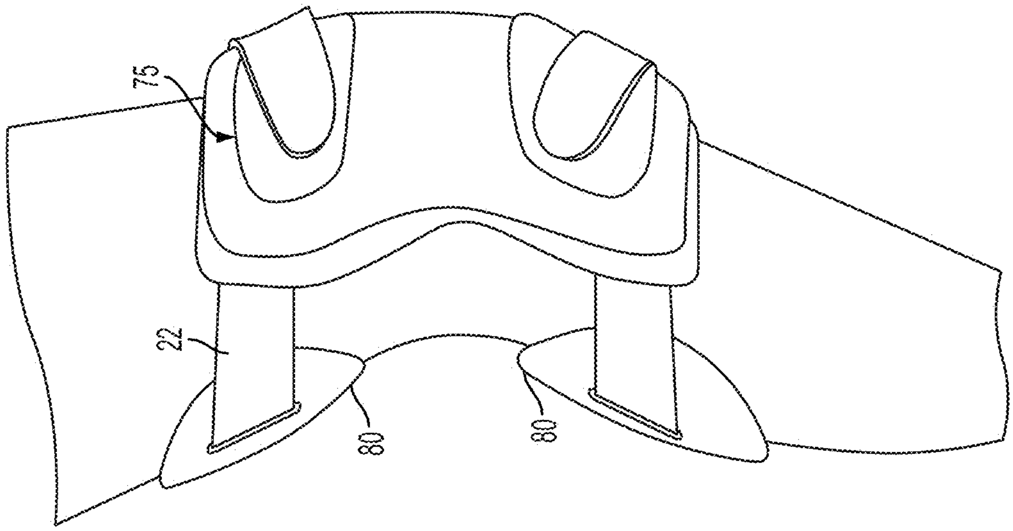
Figure 12A:
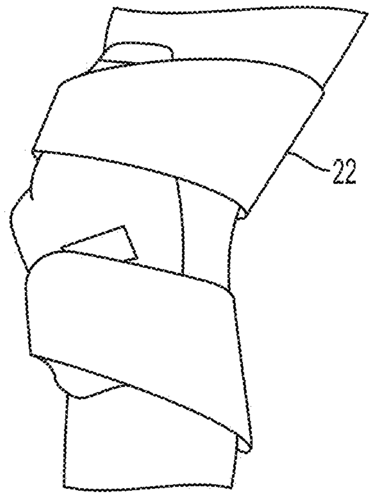
FIGS. 12A-12C depict a further representative device described herein showing a side view in place on the body and positioned in flexion (12A) or a plan view in place on the body and positioned in flexion (12C) or not on the body (12B).
Figure 12B:
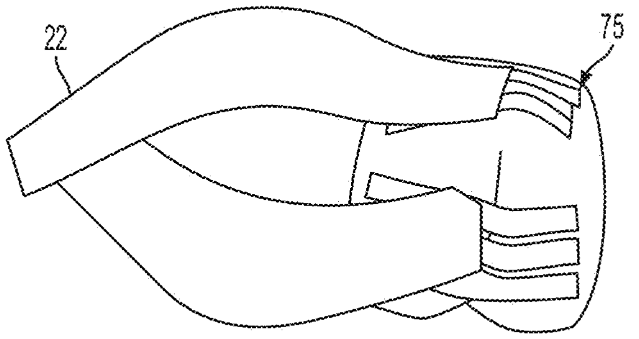
Figure 12C:
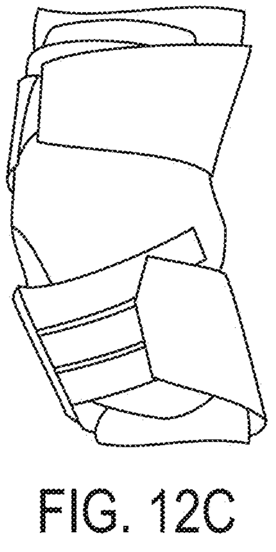
Figure 13A:
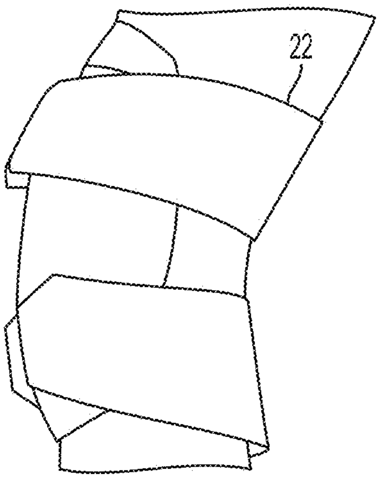
FIGS. 13A-13C depict a still further representative device described herein showing a side view in place on the body and positioned in flexion (13A) or a plan view in place on the body and positioned in flexion (13C) or not on the body (13B).
Figure 13B:
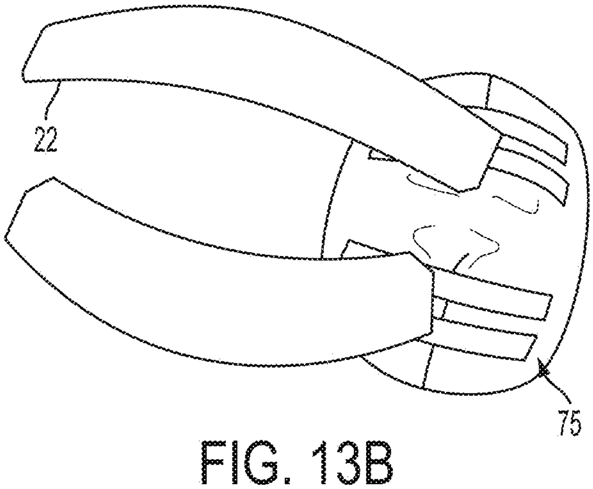
Figure 13C:
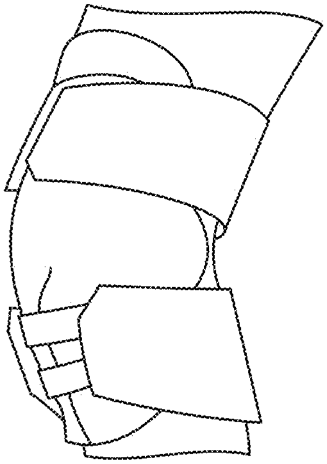
Figure 14A:
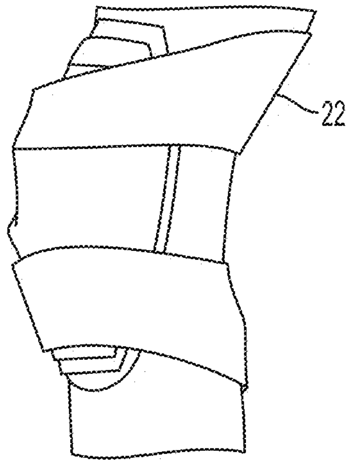
FIGS. 14A-14C depict another representative device described herein showing a side view in place on the body and positioned in flexion (14A) or a plan view in place on the body and positioned in flexion (14C) or not on the body (14B).
Figure 14B:
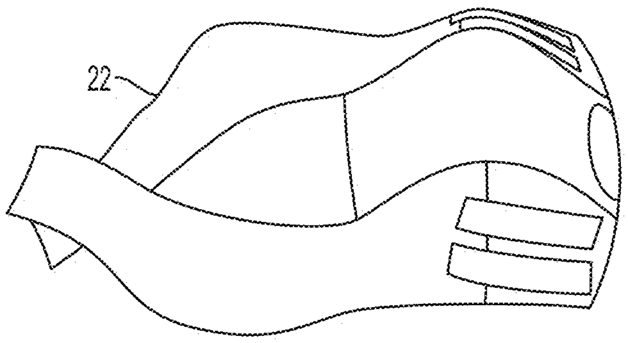
Figure 14C:
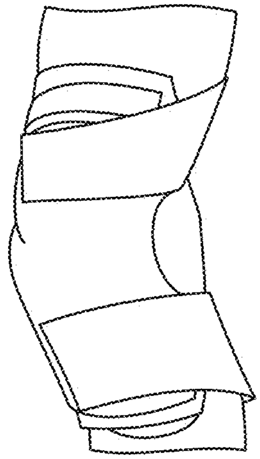
Figure 15A:
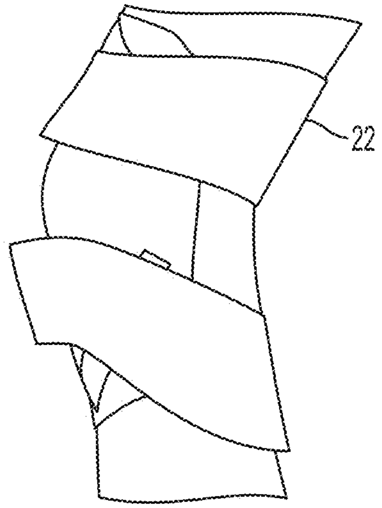
FIGS. 15A-15C depict yet another representative device described herein showing a side view in place on the body and positioned in flexion (15A) or a plan view in place on the body and positioned in flexion (15C) or not on the body (15B).
Figure 15B:
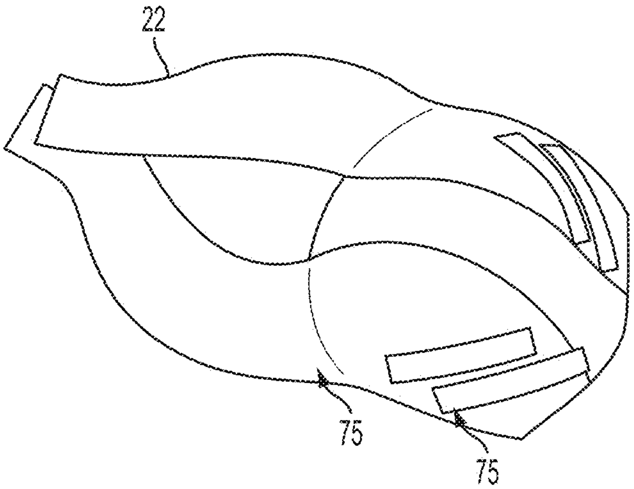
Figure 15C:
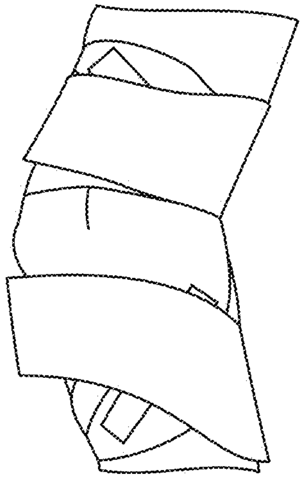
Figure 16A:
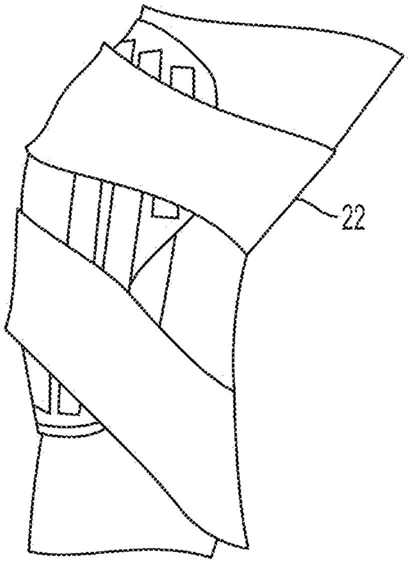
FIGS. 16A-16C depict another representative device described herein showing a side view in place on the body and positioned in flexion (16A) or a plan view in place on the body and positioned in flexion (16C) or not on the body (16B).
Figure 16B:
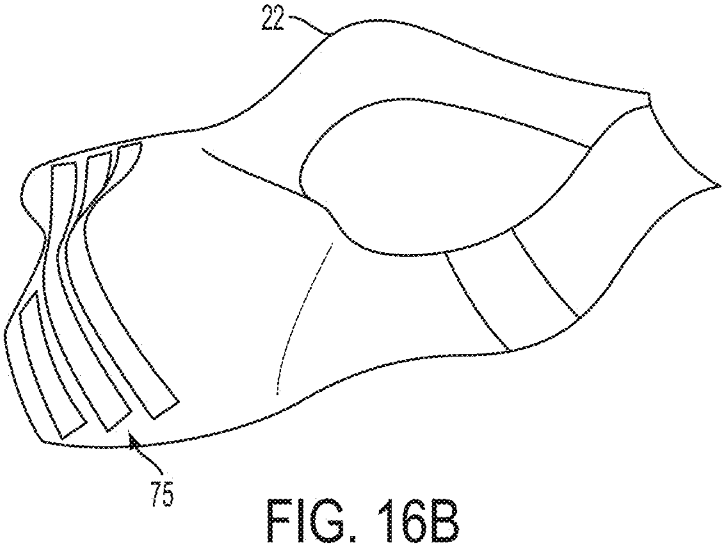
Figure 16C:
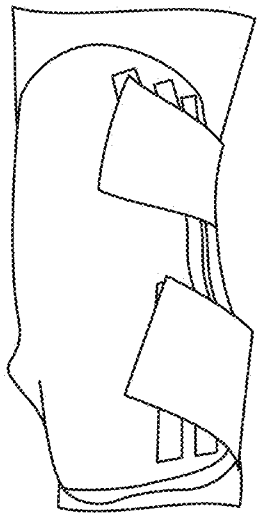

As depicted in the drawings and with additional embodiments, first segment 20 will generally include an improved ergonomic design suited to fit or conform to one or more body sites and anatomic structures. With anatomic sites, including those that are irregularly shaped, including but not limited to the knee, shoulder, elbow, and ankle, as examples, a first segment may have a first outward surface that is a receding surface and a second outward surface that is a protruding surface when formed or when forming for use, as exemplified in FIGS. 2A-2J, and 4A-4C. To assist in forming said receding and protruding outward surfaces, the first segment may further comprise gaps, slits or spaces 25 and/or accompanied with closure means or elements 27 on its first outward surface and/or its second outward surface (see FIGS. 2A-2J). The closure means, include but are not limited to adhesive fitting and/or mechanical fitting. Suitable examples include one or more clips, buttons, hooks, magnets, ties, tabs, buckles, snaps, hook and loop, Velcro, adhesive, sewing and any combination thereof. Other means are within the understanding of one of skill in the relevant art. As illustrated in FIGS. 4B 4C, and 6C, the ergonomic design may include detachable portion 29 for improved anatomic fit or operation of the device when desired. The detachable portion(s) 29 may be used to prevent fluid compression or temperature adjustments to one or more specific anatomic sites on or about the body site of interest. As such, the detachable portion(s) will often exclude components for providing fluid compression. The detachable portion may or may not include a temperature adjustable component or temperature sensitive component, as will be discussed further.

First segment 20 typically further comprises one or more extensions 22. Said extensions may be integral and continuous with first segment 20 (e.g., as depicted in FIGS. 1A, 14B, 15B, 16B) and/or may be separable (detachable and re-attachable) from the first segment 20 (e.g., FIGS. 5A-5C, 12B, 13B). Additional representative examples of extensions 22 and exemplary designs, including those for placement on a front of a knee joint, are depicted in FIGS. 7-11 and 17-19. Extensions are not required to have a particularly length or thickness, as is depicted in FIGS. 31A, 32A, 33A, 34A, 35A, and 36A. Further designs not shown would be understood by one skilled in the relevant art. The one or more extension may cooperate with each other and/or with the first segment (often on its outside or on its outward surface) by any means for securing or fastening via securing element 75, which may include but are not limited to an adhesive fitting, mechanical fitting, and/or chemical fitting. Suitable examples include a securing element having or comprising one or more clips, buttons, hooks, magnets, ties, tabs, buckles, snaps, hook and loop, Velcro, adhesive, sewing and combinations thereof. Other means for securing are within the understanding of one of skill in the relevant art. Representative examples of means for securing 75 are identified in FIGS. 11A-11B, 12A-12C, 13A-13C and 16A-16C, and are also depicted in FIGS. 31A, 32A, 33A, 34A, 35A, and 36A.

When the body site of interest is located on a limb, the one or more extensions may, in some embodiments, have a length that allows at least one extension to encircle the limb (e.g., FIGS. 8B, 11B, 12B, 13B, 14B, 15B and 16B). Alternatively, the first segment may be of a sufficient size to essentially encircle the limb. When the site of interest is located on the trunk of the body, the one or more extensions may, in some embodiments, have a length that allows at least one extension to encircle the trunk, respectively. In addition or in the alternative, a pair of extension may meet one another and cooperate by any means for securing or fastening, such as but not limited to adhesive fitting, mechanical fitting, and/or chemical fitting. Suitable examples include those previously identified, such as one or more clips, buttons, hooks, magnets, ties, tabs, buckles, snaps, hook and loop, Velcro, adhesive, sewing and combinations thereof. Other means are within the understanding of one of skill in the relevant art.

The one or more extensions as described herein provide proper placement and assist with ergonomic positioning of the device. Such described extension(s) differ from alternative forms because extensions herein are purposefully placed and configured to prevent slippage as well as migration of the extensions due to the surrounding anatomy of an area, including an area or region that said extensions should not be positioned on. For example, in one form the extensions described herein are designed ergonomically to prevent the application of pressure on a portion of the skin or soft tissue that contains sensitive and/or superficial nerves and blood vessels. In addition, the one or more extension, by design and placement ensure correct positioning of the device when under compression. By way of an example of ergonomic design and positioning, the knee is described. The knee includes a region behind the knee joint, the popliteal fossa or popliteal region. This region contains sensitive nerves and blood vessels including the common tibial peroneal nerves, the popliteal vessels, termination of the saphenous vein, an articular branch from the obturator nerve, a lower portion of the posterior femoral cutaneous nerve as well as small lymph glands. To prevent the application of pressure on the popliteal region, in some embodiments, the one or more extensions described herein, when cooperative with a device for use on or near the front of the knee joint (used only as an example), are configured in a manner such that each extension extends away from the region behind the knee when at or near the vicinity of the popliteal region while also being positioned ergonomically at or near the edges (proximal and distal edges) of the devices. This specific and unique design prevents the application of constriction on that region. The design further may include a curvilinear shape to the extension, the shape extending away from the popliteal region. The ergonomic design along with the placement at or near the distal and proximal ends of the device prevents migration of the extensions towards the popliteal region, which occurs in alternative designs that are not configured nor placed as described herein. Thus, as described herein is a device designed for protection of one or more sensitive regions near the body site of interest. This is further combined, in many embodiments, with the prevention of any intermittent compression provided to such sensitive regions.

As such, in some embodiments, the one or more extensions described herein will, in some embodiments, include curvatures in the extension regions (or a portion thereof) that curve away from a sensitive region at that site. In one example when positioning on a front of a knee joint, with use of a pair of extensions to assist in positioning of the device (each or both extensions meeting one another and/or wrapping around the limb), a first extension(s) is placed on or near the proximal end or portion of the device (thus, when secured, is positioned about the lower thigh region and above the popliteal region) and a second extension(s) is placed on or near the distal end or portion of the device (thus, when secured, is positioned about the upper calf region and below the popliteal region). In another example when the site of interest is the elbow joint and with each or both extensions meeting one another and/or wrapping around the limb, each extension may be placed a distance away from each other (generally extension(s) on a more distal portion or edge of the device as well as on a more proximal portion or edge of the device) with each having a curvature curving away from the sensitive nerves and blood vessels on the inside of the articulating elbow for preventing constriction of the radial and brachial artery and median and radial nerves. Thus, when secured, proximal extension(s) position about a lowermost region or the upper arm and above the inside space of the articulating elbow (to prevent constriction of the inside of the articulating elbow) and distal extension(s) position about the uppermost region of the lower arm and below the inside space of the articulating elbow (to prevent constriction of the inside of the articulating elbow). In a further example when a device is about the wrist, proximal and distal extensions may be placed a distance away from each other (each or both extensions meeting one another and/or wrapping around the limb) and each extension may include a curvature away from the palm side of the wrist and the tunnels therein that support and allow passage of the ulnar nerve and the ulnar artery as well as the median nerve (Guyon's canal and the carpal tunnel) to prevent constriction of said canal and tunnel.

Ergonomic assistance may also be provided by support 80 (e.g., FIGS. 11A-11B), which may offer a threaded, looped, Velcro-like and/or other suitable configuration for releasable (and moveable) cooperation with extension 22. Support 80 assists in positioning and placement of extensions, as needed. Support 80 may be provided in a region to prevent excess pressure from the one or more extension and also may be provided to expand the surface area of the extension, and for assisting in the prevention of movement of the extension and of the device.

In one or more embodiments, a described configuration of extensions requires sufficient spacing between extensions and, for many embodiments, includes a curvilinear shaping of at least one of the one or more extensions, in which the curved portion curves away from a particular region to avoid constriction of that particular region as well as preventing migration of the extension towards the particular region. Thickness of the extensions is limited only when preventing constriction of a particular region at or near the body site. In these embodiments, without sufficient spacing and/or curvilinear shaping, the positioning of the extension(s) will be counterproductive. This is because in their absence, migration results in constriction of the particular region, which in some regions may have a detrimental effect.

Figure 1B:
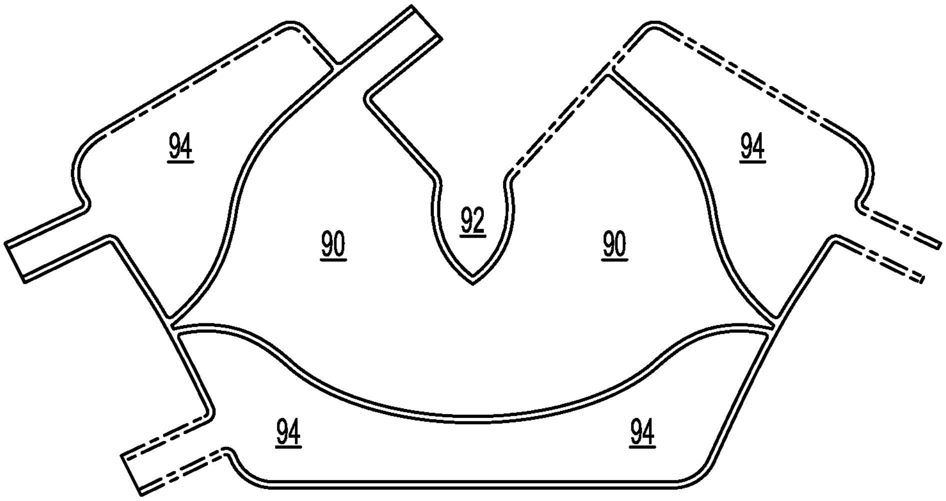
FIGS. 1B and 1E depict representative leakproof elements described herein.
Figure 1C:
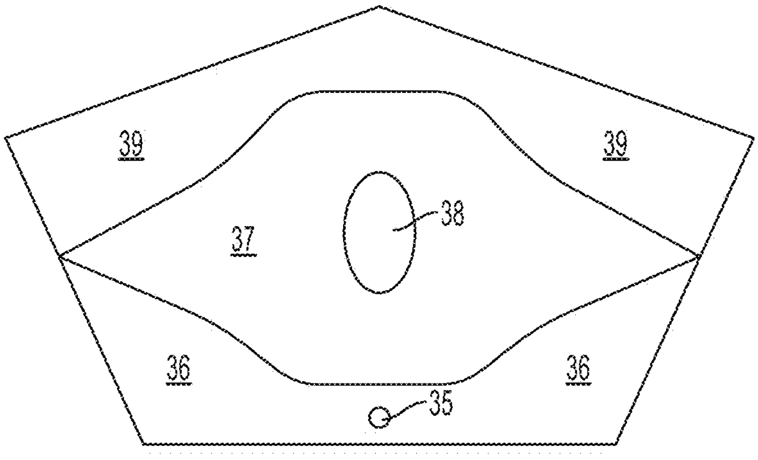
FIGS. 1C and 1D depict representative bladders described herein.
Figure 1D:
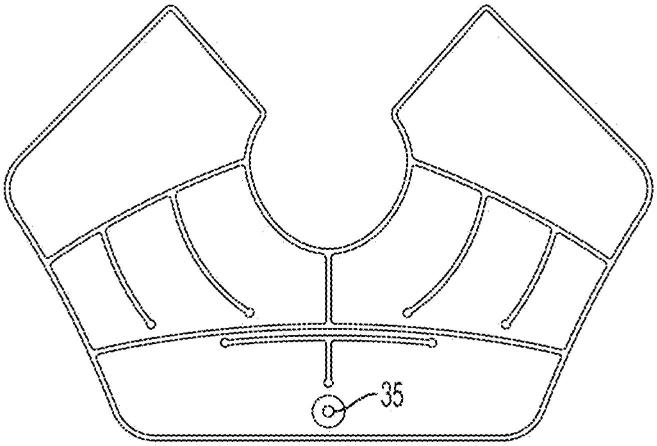

As described previously, the first segment of the compression device will include two opposing facing surfaces, each extending outwardly. The first outward facing surface is the surface that faces the body. This surface may be also be considered an inner (inside) facing surface and, in some embodiments, may be positioned directly on or about the body site or, in other embodiments includes an intervening surface, preventing some of the inner facing surface from direct contact with the body site or body surface. An example of the first outward facing surface (inside facing surface) is depicted in FIG. 1G, in which an intervening surface is shown. The intervening surface may cooperate with the entire first outward facing surface or only one or more portions thereof. In some embodiments, the intervening surface is a protective or resistant surface or layer. In some embodiments, the intervening surface is a plurality of layers. The intervening surface may be a separate layer or a plurality of layers and may be adhered or simply secured in some fashion to either the first outward facing surface of the part of the first outward facing surface, such as its edges. The first outward surface of the first segment may also comprise a pocket or housing into which all or a portion of the second segment is positioned, when included with the device. The first outward surface of the first segment (and/or the intervening surface) may also comprise securing element, such as those identified and understood in the art, to secure at least a portion of the second segment, when included with the device. The portion of the second segment that may be secured to the first segment (when included) is often near the outer or peripheral edges of the second segment. Thus, the means for securing the second segment with the first segment will not interfere with the function of the device or with operation of the second segment. The second segment, when included, is cooperative with the first outward facing surface or with the intervening surface (when included in the manner described, by being located between the first outward facing surface of the first segment and one of the outward surfaces of the second segment).

The second outward facing surface of the first segment is the surface viewed or externally visible when the device is positioned on or about the body site, generally as depicted in FIGS. 1A, 2-16, 17A, 18A, and 19A, and as shown as the outward facing surfaces of FIGS. 31A, 32A, 33A, 34A, 35A, and 36A. One or both of the first and second outward facing surfaces of the first segment may be porous, and/or made in whole or in part of a material that is breathable. A suitable example is a material made into a fabric; the material may be natural or synthetic. The material may be one that can be sewn into, and/or one to which a layer and/or another element may be adhered or otherwise secured to, using a means for securing, as previously described or as is known in the art. One or both of the first and second outward facing surfaces may also, in some embodiments, be of or combined with surfaces or materials or layers that offer water repellency, water resistance, water wicking and combinations thereof. In some embodiments, the intervening surface is water repellent, water resistant, water wicking, or some combination thereof. Examples include a water repellent, water resistant, and/or water wicking plastic, or a water repellent, water resistant, and/or water wicking fabric, or a water repellent, water resistant, and/or water wicking film, and/or water repellent, water resistant, water wicking paint.

The first and second outward facing surfaces may be on opposing sides and may be of the same composition or material or layer thereof (e.g., together forming a singular wall with a first opposing facing surface and a second opposing facing surface) or may be on independent compositions or materials, such that each composition or material is itself a single layer or multiple layers (e.g., each independently forming a singular wall, a first singular wall having the first opposing facing surface and the second singular wall having a second opposing facing surface). When the first and second outward facing surfaces are independent, between the first and second outward facing surfaces is positioned a fluid holding chamber, filling element or bladder. Upon positioning the bladder, the first and second outward facing surfaces are generally secured together. The means for securing may be permanent or may be releasable allowing access to the bladder, now configured within the interior space of the first segment. The means for securing may also be permanent about a portion and releasable about a portion. Often the first and second outward surfaces are secured at their periphery, thereby providing a large interior space for the first segment. When only a portion of the surfaces are secured permanently, the interior surface may be accessed after positioning the bladder. For example, a zipper, snaps or Velcro may be used along a portion of the periphery. Such access allows the bladder, for example, to be replaced when needed, such as when damaged or when requiring a different bladder. In some embodiments, the means for securing does not also secure the bladder to the first segment. In some embodiments, separate securing elements (means for securing as previously described) are used to secure or fasten the bladder to at least a portion of the interior surface of the first segment. It is also possible, in some embodiments, to secure the bladder to the interior of the first segment at the same time that the first segment, itself is secured (e.g., the first and second outward facing surfaces). In all instances, the bladder, when secured, will only be secured (to the interior of the first segment) in regions of the bladder that do not interfere with its operation and/or function.

When the first and second outward facing surfaces are of the same composition or material or layer, there will not be an interior space. Here, the bladder will often be positioned in contact with the first outward facing surface that faces the site of interest (inside facing). In some embodiments, there may be an intervening layer(s) between the outward facing surface and the bladder.

The device described herein generally includes only one bladder. The bladder as described herein comprises one or a plurality of chambers, said chambers configured for sequential and directional inflation of the bladder with input of a fluid. The fluid source may be a pump, compressor or other suitable means for introducing fluid into the bladder. The bladder may be at or about the same size as the body portion of the first segment. In some embodiments, such as when the bladder is fitted in the interior of the first segment, the bladder may be smaller of just slightly smaller in size than the body of the first segment. The bladder, which expands and contracts with each cycle of compression, as such will, depending on its size, and the number of active (e.g., fluid filling) compartments, will expand and contract all, or most, or less than the body portion of the first segment. Representative examples of bladders are depicted in FIGS. 1C-1D, as well as FIGS. 31C-31D, 32C-32D, 33C-33D, 34C-34D, 35C-35D, and 36C-36D. Each configuration is generally suitable for placement about a joint, such as a knee joint, or for placement about a portion of the limb or trunk of the body. Additional configurations and designs are also acceptable as would be understood by one skilled in the relevant art.

The bladder is capable of being filled with fluid, such as air, other gas, liquid or gel and, with each compression cycle, is capable of maintaining said fluid without substantial loss of the fluid. Fluid is introduced into the bladder by way of the fluid source (e.g., source 60 in FIG. 1A) and is directed in via the fill port (e.g., port 35 in FIGS. 1C-1D) generally by way of one or more connecting elements (e.g., connecting element 40 in FIG. 1A). The fill port will be positioned on or near a distal end or distal region of the bladder, and generally includes a region extending through the receiver 46 of the first segment. The fluid may be released, dissipate, vent or may exit by ways known in the art. In one or more forms, fluid release occurs by way of a solenoid valve operably coupled with the fluid source (e.g., pump). In other embodiments, a second port may be provided in the bladder and/or as an exhaust (e.g., conduit) associated with the source. Generally, fluid is moved in cycles. The fluid may be introduced for the same cycle duration each time or different cycle durations. With each cycle, fluid may be introduced for the entire inflation period or in pulses or in sinusoidal fluctuations, sometimes only during a portion of the inflation period.

The directional compression provided by the device described herein is such that fluid is filled directionally from a first chamber of the bladder and optionally to at least one or more additional chambers. The first chamber or at least entry of fluid (via the fill port) into the first chamber is such that fluid entry and/or positioning of the first chamber is further away from or is a more distal chamber or region with respect to the position of the bladder when in use, the distal region being a region of the bladder further from the heart, rather than having fluid entry into a region or compartment of the a chamber that is closest (proximal) to the heart. The remaining chamber(s) when included are closer or less distal than the first chamber with respect to the heart. Thus, in some embodiments, one or more distal chambers fill first followed by one or more less distal chambers. In some embodiments, a single chamber fills passively but is filled at a specific location that is most or more distal from the heart (e.g., near a distal portion of the bladder with respect to the position of the bladder when in use). In FIGS. 1C-1D, a fill port 35 is depicted, which will be used to direct fluid into the bladder. As it can be seen, the fill port is at a distal portion of the bladder, which is a region that is further from the heart. The fill port is not typically at the edge of the bladder but may be near the edge or may at least be near a distal portion of the bladder. In addition, it is noted that for some joints, such as the knee, a bladder may have one or more fluid chambers that are not filled with any fluid, such as depicted in FIG. 1C, with chamber 38, which is a hole or an unfilled space. In one example, fluid is introduced into fill port 35. By way of the chamber configuration of FIG. 1C, fluid will fill chamber 36 first, followed by 37 and finally chamber 39, with no fluid entering chamber 38. As described, in one or more embodiments, fluid enters the bladder in a predetermined and directional fashion, thereby introducing compression to the body site in a sequential and directional manner. For example, the bladder may include channels that direct fluid movement in a directional fashion.

The one or plurality of bladder chambers are, in some embodiments, in fluid communication with one another, such that one fluid source is sufficient to introduce fluid to the bladder in a sequential and directional manner. With more than one chamber, the bladder may, in other embodiments, be wholly or partially compartmentalized, which may use the same fluid source (e.g., by way of one or more valves, couplings and/or connecting elements) or, in turn, use additional and/or separate fluid sources to introduce fluid into each of the compartmentalized chambers in a sequential and directional manner. Such chambers may then be individualized with less, negligible or no fluid communication between them. Regardless of the number of chambers and/or fluid sources, the fluid is introduced into the bladder, as described previously, with an initial introduction to one or more first chambers that are most or more distal from the heart followed by sequentially introducing fluid and, hence compression, to any additional chambers that are located less distal than the first chamber(s) with respect to the heart. As described previously, the bladder may further comprise a discharge unit (e.g., release valve and accompanying components) for release of the fluid, as needed. Access to the discharge unit of the bladder may be through the first segment, when the bladder is fitted within the first segment (e.g., by a separate receiver or inlet). Thus, as described herein is a bladder that may contain at least one chamber that inflates from a distal portion to a proximal portion, or may be a plurality of, or more than one compartment in a chamber, such that the compartments inflate sequentially. Sequential inflation may also be introduced by restricting flow between one or more chambers. In some embodiments this may be via a valve, narrowed passage or a regulated valve set to move only in response to a predefined pressure and/or by compartmentalizing the chambers, each chamber associated with a separate fluid source and inflated under a predefined and controlled pattern or sequence or pressure (e.g., via solenoid valves). In one or more embodiments, a filler material is positioned between adjacent compartments. The filler material is generally a very porous material or a foam-like material, as is known in the art. The filler material should be highly porous or porous enough so that is does not interfere significantly with fluid flow. It generally assists in maintaining an opening between compartments. It is generally positioned where there is a space or a gap provided along a seam line formed between adjacent compartments. The filler material may also be positioned in a larger compartment to prevent collapse and ensure fluid flow and proper filling of the compartment.

The size of the bladder will depend on the treatment area and location of the body site. In many embodiments, the body site is at or about a joint, including one or more of a finger joint, wrist, elbow, shoulder, hip, knee, ankle, foot and toe joint. The body site may further comprise a portion of a limb or the trunk, such as the foot, arm (forearm, upper arm), leg (calf, thigh), or lower trunk (lower back, buttocks). When the device is for positioning on or about a joint surface, the bladder is often designed specifically for placement on or about said joint. As depicted in FIG. 1C-1D, a bladder is uniquely shaped for configuration about a joint, such as a knee. In many embodiments, the bladder, itself, will not wrap around the entire limb, but will be properly sized to provide compression to only the treatment site (e.g., the joint or the portion of the limb or trunk that has been injured). Representative bladder configurations may also prevent compression directly on certain portions of the treatment site that are sensitive to pressure, such as depicted in FIGS. 1B-1C and 6, in which such examples do not introduce compression directly on the patella. Further examples include designs that minimize or avoid pressure on other parts of the body, such as the proximal surface of the proximal phalanx, the lateral malleolus, and the medial malleolus. As an alternative, the entire device, including the bladder may be configured to wrap around a substantial portion of the joint or around the entire limb.

Typically fluid and, hence, compression, is introduced cyclically; the degree of compression depends on the volume of fluid introduced into the bladder. It has been found that by providing specified algorithms for introducing fluid into the bladder, and, hence, compressing the uniquely configured bladder intermittently and/or cyclically, treatment of the site may be optimized. With minimal information, treatment algorithms may be prepared for a variety of body sites in order to maximize treatment and provide a more uniform plan of treatment. In some embodiments, the treatment duration may include a plurality of cyclical inflation and deflation cycles over the treatment duration. The treatment duration may be for only a few minutes or for many minutes, as will be described more fully below. Examples of various inflation-deflation cycles are represented in TABLE 1 as modes A, B, C, and D.

TABLE 1

| Mode | Peak Pressure (ON) (mm Hg) | Low Pressure (mm Hg) | Time (ON) (seconds) | Time (OFF) (seconds) | Duration (minutes) |
|---|---|---|---|---|---|
| A | 30 | 0 | 40 | 20 | 15 |
| B | 50 | 0 | 35 | 25 | 15 |

TABLE 1-continued

| Mode | Peak Pressure (ON) (mm Hg) | Low Pressure (mm Hg) | Time (ON) (seconds) | Time (OFF) (seconds) | Duration (minutes) |
|---|---|---|---|---|---|
| C | 70 | 0 | 30 | 30 | 15 |
| D | 85 | 0 | 25 | 35 | 15 |

In one or more embodiments, the bladder is configured to fit within the first segment. In some embodiments the bladder is cooperative with all or a portion of the second segment (e.g., second segment 30 as depicted in FIG. 1A). In some embodiments, the bladder and second segment will have very similar dimensions, such as length and width, while the thickness of the bladder and the second segment may differ. In some embodiments, the bladder will be smaller or just slightly smaller than the first segment to fit within the body of the first segment. The second segment will also be smaller than the body of the first segment. In some embodiments, the second segment will have similar or many overlapping dimensions as the bladder, while the second segment will overall have reduced dimensions. In one or more embodiments, the body of the first segment (when looking at a front view) will be larger than the overall size and shape of the bladder (when looking at a front view), and the bladder will be larger than the overall size and shape of the second segment (when looking at a front view).

For example, a bladder design such as that represented in FIG. 1C may, in some embodiments, cooperate with a second segment as represented in FIG. 1B, such that chamber 38 of the bladder and region 90 of the second segment are similarly positioned with respect to one another and chamber 37 of the bladder and region 90 of the second segment are similarly positioned with respect to one another (when viewing both elements in a front view). Cooperation between the bladder design and the design of the second segment may refer to their shape and size (when viewing in a front view, such as depicted in FIGS. 1B-1C). Cooperation does not require the bladder and the second segment to be in direct contact with one another. There may be an intervening layer and/or a facing surface of the first segment residing between the bladder and the second segment; however, the bladder and the second segment are generally so positioned that there are compartments in each that are cooperative with one another. It will be further understood that for certain anatomic structures, the second segment may be further shaped in order to offer an improved mating between the first segment and the second segment when the device is positioned for use. For example, when the first segment is shaped for some anatomic structures to include a first outward surface that is a receding surface and a second outward surface that is a protruding surface, the second segment can be similarly shaped by way of one or more connecting elements (e.g., connecting elements or couplers 32, as represented in FIGS. 1A and 1F). Such connecting elements provided to the second segment allow for a similar surface configuration to the second segment in order that it also includes a protruding surface and an opposing receding surface. Connecting elements or couplers may be positioned on spaced apart ends of the second segment that are then brought together via the connecting elements. These ends may be inside ends, as depicted in FIG. 1F. A representative example of such a second segment further shaped with connecting elements to provide a protruding surface and an opposing receding surface is depicted in FIG. 1F. Connecting elements or couplers 32 may be of the same type used, for example, as securing elements 34 or securing element 75, and described previously. Said couplers may are generally adhered to and fixed in position on the second element and include an extended or coupling portion or mating portion that is compatible with another coupler for mating and coupling purposes. As shown in FIGS. 1A and 1F, at least or both of the two mating couplers may be provided on an extended portion or protrusion of the second segment; this helps prevent or reduce interference of the couplers with operation of the second segment.

The second segment is a leakproof element encasing a temperature sensitive component or material. The temperature sensitive component or material described herein is typically a fluid in liquid or gel form but may, in some embodiments, be a malleable or formable solid. In one or more features the temperature sensitive component is a gel and may be a hydrogel, as is understood in the art. Examples of useful materials for a gel include but are not limited to silica (e.g., vinyl-coated silica gel), hydroxyethyl cellulose, cellosize (e.g., Cellosize QP-100M-H), propylene glycol or a slush powder (superabsorbent polymer or superabsorbent crosslinked powder or superabsorbent crosslinked sodium polymer, an example of which is Temtro Dry Gel from Roshgo Corporation, Alpharetta, Ga.). In many embodiments, the temperature sensitive component is capable of achieving a lower freezing temperature than that of water. As such, devices described herein will, when using such lower temperature materials, achieve a temperature in the underlying tissue or body site that is less than what would be achieved with a device that circulates water or ice water. For example, devices that circulate cold or ice water do not achieve a temperature in the tissue that is generally less than about 60 degrees Fahrenheit (F) when applied for short time periods, such as 15 minutes or 20 minutes or 30 minutes (as examples). On the other hand, a device described herein using a temperature sensitive component described herein will achieve a temperature in the underlying tissue that is less than 60 degrees F. and may achieve a temperature in the underlying tissue that is less than 50 degrees F. or even much less. The temperature sensitive component may also contain an antifreeze material, such as but not limited to propylene glycol, ethylene glycol, glycerol, and sodium chloride. When included with a temperature sensitive component that contains some water, the antifreeze material will keep the component elastic when it reaches a temperature below the freezing point of water. The temperature sensitive component may further include a preservative such as, but not limited to methyl chloro isothiazolinone, methyl isothiazolinone, methylparaben, propylparaben, diazolidinyl urea or various combinations thereof. Preservatives can be used to increase the life of the temperature sensitive component by for example inhibiting its degradation or prevents is contamination. The temperature sensitive component may further include a chemical indicator that indicates when a desired temperature is met and/or when a desired temperature is lost. The indicator chemical is generally in the form of a dye or a thermochromic ink or may be a chemiabsorbant molecule. In one or more embodiments, the temperature sensitive component is preferably a material that can be adjusted from a first temperature to a second temperature but will return to (or near) its first temperature over time (e.g., when removed from the second temperature), because the material, when removed from the second temperature can only maintain that second temperature for a set and definite period of time. Such a material is often preferable for treatment of a body site because it is considered safe, according the Federal Drug Administration, since it reduces the risk of direct or indirect injury or damage associated with overheating or overcooling a body site. This is contrasted with a cool or ice water circulating device that has been associated with severe damage as well as frostbite to a body site, such as a limb, when used for a period of time.

Figure 1E:
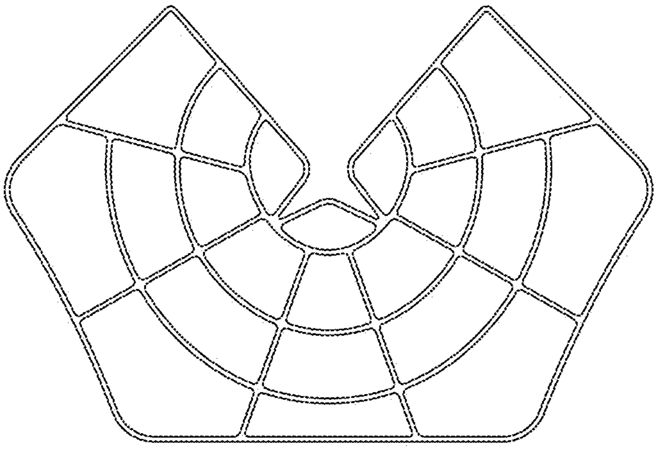
Figure 1F:
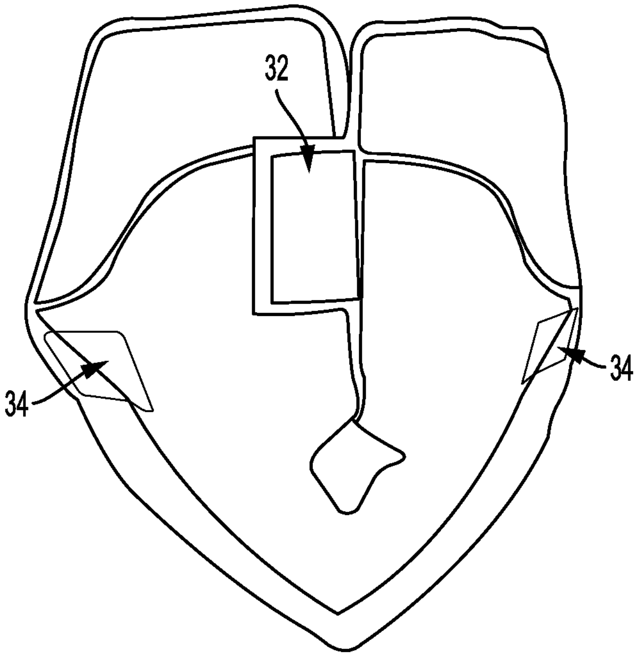
FIG. 1F depicts the leakproof element of FIG. 1B after further shaping for placement on a portion of the body.
Figure 1G:
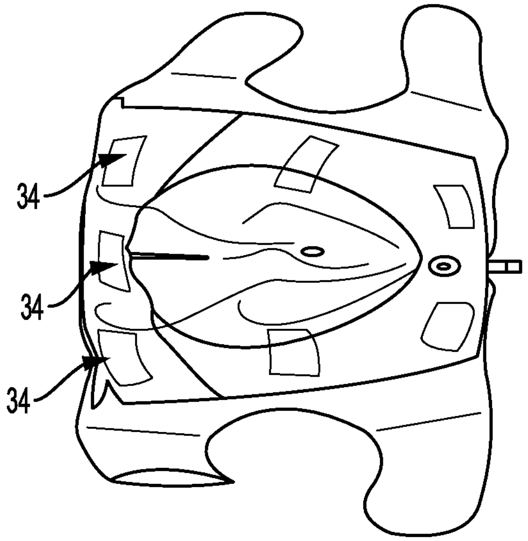
FIG. 1G depicts the opposing outwardly facing surface of the representative device of FIG. 1A.
Figure 2A:
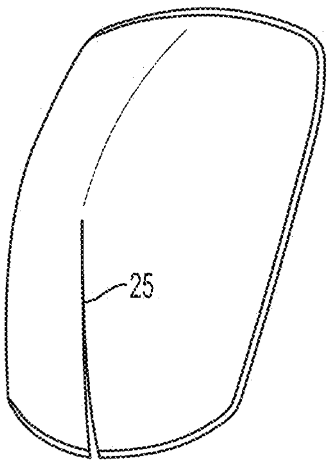
FIGS. 2A-2J depict representative first segments described herein.
Figure 2B:
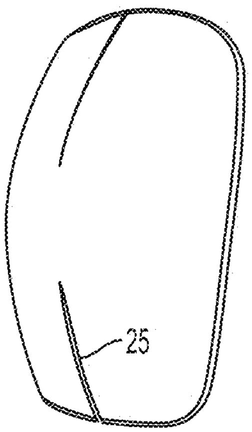
Figure 2C:
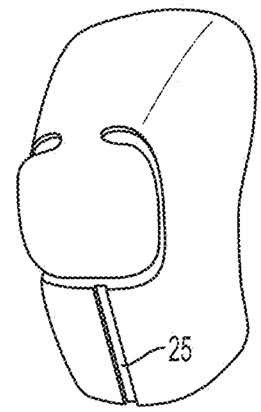
Figure 2D:
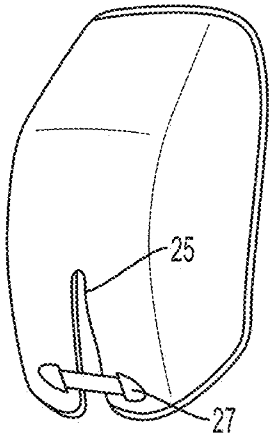
Figure 2E:
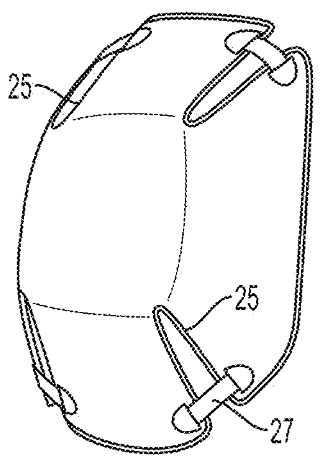
Figure 2F:
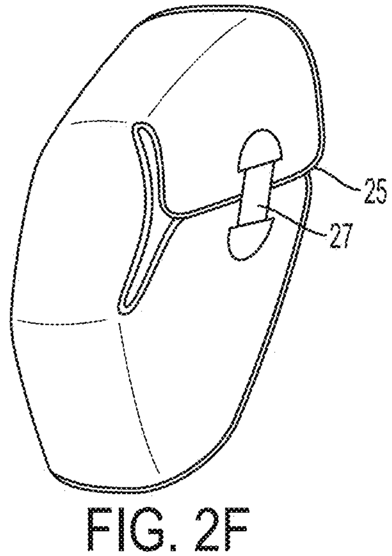
Figure 2G:
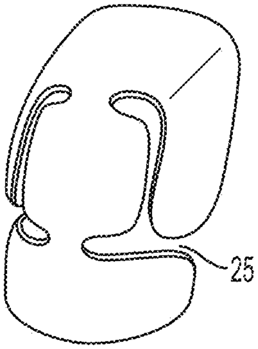
Figure 2H:
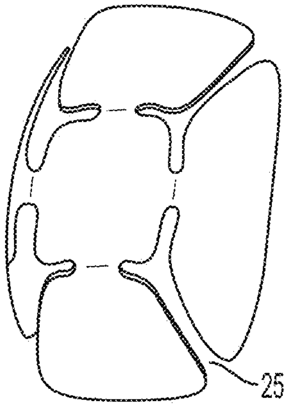
Figure 2I:
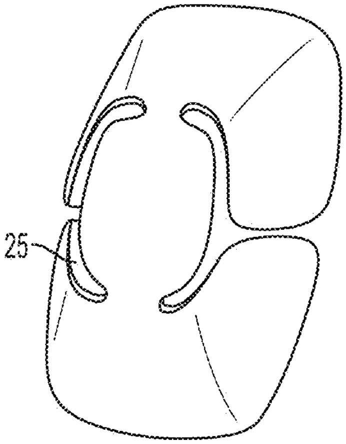
Figure 2J:
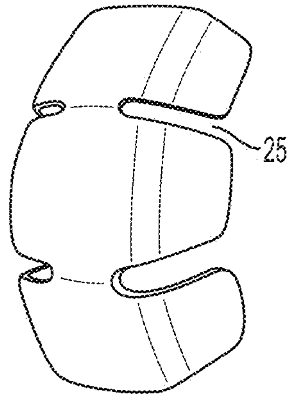
Figure 3A:
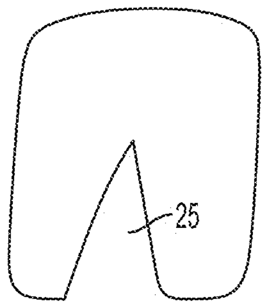
FIG. 3A depicts a front (flat) view of the first segment of FIG. 2A.
Figure 3B:
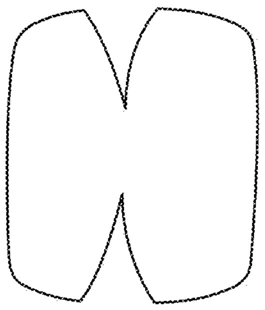
FIG. 3B depicts a front (flat) view of the first segment of FIG. 2B.
Figure 3C:
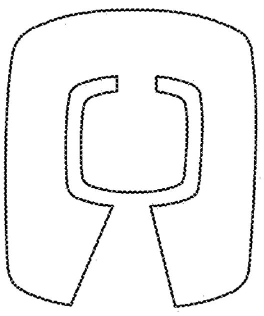
FIG. 3C depicts a front (flat) view of the first segment of FIG. 2C.

Representative examples of leakproof elements are depicted in FIGS. 1A, 1B, 1E, and IF, 31E, 32D, 33D, 34E, 35E, and 36E. As described, the size and shape of the leakproof element may be similar to that of the bladder described above. The size and shape of the leakproof element may also be just slightly less than that of the bladder described above, such as only incrementally smaller (e.g., by less than an inch around its periphery, or by less than an inch or a few inches in overall size and shape when viewed in a front view). The leakproof element may be smaller in general size than the bladder. Such arrangements allow for a unique cooperation between the bladder and the temperature sensitive component, providing a more even distribution of temperature across the one or more areas of compression, which translates to an improvement in the effective temperature achieved in the tissue at the site of interest.

While in some embodiments, the effective temperature achieved in the tissue at the site of interest may be substantially the same across the entire site after providing intermittent compression with a device described herein, in other embodiments, when desired, the effective temperature at portions of the body site of interest may vary. In one or more forms, gradients in temperature may be achieved by compartmentalizing the temperature sensitive component in which some compartments include a larger volume or amount of the temperature sensitive component and/or by offering different pressures to different portions of the bladder. In addition, an intervening layer and or materials may be included in the second segment to enhance or decrease temperature effects on a particular site when the device is positioned for use. In one example, with reference to FIG. 1B, the second segment will include at least compartments or regions 90, 92, and 94. In one embodiment, region 90 has more temperature sensitive component per unit area than either region 94 or region 92. The amount of temperature sensitive component in region 90 (combined) may be as much as or more than twice the amount in region 94 (combined). The amount of temperature sensitive component in region 92 will, in the embodiment of FIG. 1B, be nonexistent. However, should the second segment include instead a nonfunctional compartment in region 92 or one that includes a small or negligible amount of the temperature sensitive component, the amount of temperature sensitive component in region 92 will, in these embodiments, be small or negligible, respectively. In another embodiment, region 90 has the same amount (per unit area) of temperature sensitive component per unit area as region 94.

Compartmentalization within the leakproof element is desired to reduce movement of the temperature sensitive component. Without compartmentalization, at least some of the temperature sensitive component will migrate when the device is compressed in a sequential and intermittent manner, resulting in the unequal distribution of the temperature sensitive component over time, which will lead to an inability of the device to achieve an even temperature distribution in the underlying tissue. Thus, as described herein, the second segment often includes filling compartments to prevent migration of the temperature sensitive component. Said filling compartments may be entirely separate or offer some minimal fluid communication with at least one other compartment. Another advantage of the leakproof elements described herein is that, by allowing them to take one of two shapes (a first initial shape, such as one that can be laid flat on a surface, and a second further shape, such as one that is conformed to that of the first segment via, e.g., couplers and the like), they may be readily stacked when in its first shape (such as laid flat on a supporting surface in a freezer) without taking up a significant amount of space. When desired, the leakproof element may be quickly replaced by another, such as when the temperature sensitive component is no longer capable of achieving a desired temperature. In one or more embodiments, the leakproof element can be secured and also removed from the first segment. Securement is via cooperative mating or coupling of the one or more securing elements 34 on the second elements (see, e.g., FIG. 1F) with the one or more securing elements 34 on the inner facing surface of the first segment described previously (see, e.g., FIG. 1G). Said cooperative mating is generally going to be one that is reversible, thus allowing said first and second segments to join for some period of time (e.g., when in use) and to separate (e.g., when not in use). The cooperative mating helps ensure that the second segment does not move during use, and assists in proper placement of the second segment, such that its temperature sensitive component, especially when compartmentalized, remains cooperative with the bladder. When either or both the second segment and the bladder are compartmentalized, the cooperative mating of the second segment with the first segment helps coordination and alignment of the compartments so that, as designed, said bladder and second segment (as well as their designed compartments) remain cooperative during operation of the device.

In some embodiments, a combination of sequential and intermittent compression associated with the first segment and a unique distribution and compartmentalization of the temperature sensitive component in the second segment is provided. Compartmentalization of the temperature sensitive component in the second segment may be specifically coordinated with the bladder, such that the bladder (associated with the first segment) and the second segment are similar or substantially the same in their overall shape (e.g., similar though not necessarily identical in their overall front view dimensions, as discussed previously). Moreover, the bladder may also be compartmentalized, having at least more than one chamber that cooperates with similarly positioned compartments in the second segment in order to maintain a uniform distribution of the temperature sensitive component housed in the second segment. The bladder may be compartmentalized, having one or more chambers that cooperate with similarly positioned compartments in the second segment, in which one or more compartments in the second segment include a similar or substantially the same volume (amount) of temperature sensitive component in the one or more compartments. In the alternative, the bladder may be compartmentalized, having one or more chambers that cooperate with similarly positioned compartments in the second segment, in which one or more compartments in the second segment include differing volumes (amounts) of temperature sensitive component. Thus, as described, is a leakproof element housing a temperature sensitive component that when positioned as described and aligned with the first segment provides a compression system offering improved temperature distribution as well as a colder temperature to the underlying body site. The device described will, by pressure and/or amount or type of temperature sensitive component, be uniquely designed to provide a specified temperature or pressure, or temperature range or pressure range to the underlying body site. The device described herein is capable of specifying the type of temperature sensitive component, the amount (volume) of the temperature sensitive component and/or the pressure algorithm applied. In addition, when desired, the distribution of temperature across the underlying body site (from one location to another) may be more specifically regulated by compartmentalizing the temperature sensitive component is and/or specifying the distribution of the temperature sensitive component within compartments of the second segment.

A predetermined algorithm described herein may be provided to achieve a desired treatment outcome. It has previously been understood that when a cold ice pack is applied continuously with some pressure to an anatomic site, the longer the time of application of the cold pack the colder the surface of the skin (just below the cold pack) will be (e.g., Janwantanakul P, Physiotherapy 2006; 92(4):254-259). As described herein, compression, applied intermittently, was found to significantly increase the cooling effect on the tissue surface as well as within the tissue (below the tissue surface) (see also Tables 2-4). The described invention has thus, with the application of intermittent compression, been able to alter the amount of compression of the device (pressure) in relation to the total treatment time in order to achieve skin temperature values that are the same or similar (for each treatment scenario). Thus, when a certain relative tissue temperature is desired and the total time for treatment is to remain the same, the pressure level and compression time will be varied as it relates to the time of inflation. In this manner, the total time of inflation and the amount of pressure only are manipulated (while total time of treatment remains the same). In some embodiments, there will then be a general decrease in the total time of inflation when the amount of pressure is increased. In other embodiments, the compression level will be changed (with the same device) in order to achieve a same (or similar) temperature with or without changing the compression time.

Thus, by performing only a few test runs with a device described herein (the device having a specific temperature sensitive component), one will be able to set the device to provide, a similar temperature profile to the anatomic site when intermittent compression is applied by said device. Accordingly, as described herein, is a standardized treatment of care to a site of interest in order to achieve good efficacy and outcome over several separate treatment sessions.

In a first example, a compression device described herein had a first segment with a bladder provided within its body portion; the bladder had a fill hole at its more distal end that introduced pressure via a portable pump that inflated the bladder from the distal end to the proximal end. The bladder in a centermost region had a hole, which, therefore, did not inflate. The first segment had a first outward facing surface that was recessed near its more center region and a second outward facing surface that protruded near its more center region. The first segment as described is suitable for an anatomic structure such as a joint which has an anatomic portion that protrudes or is for use when a joint is bent. The first segment, with or without the protruding and recessed facing surfaces, may also be used on other anatomic structures. The first segment included a pair of extensions at its more distal end and a pair of extensions at its more proximal end. The pairs of extensions were each curved, with curvatures that prevented the extensions from migrating towards one another (arcs curving outwardly, away from the center of the device). The pairs of extensions each had mating connections and hence were capable of securely wrapping about a limb. The second segment had an overall general shape that was similar to the general shape of the bladder in the first segment, with the exception of spaced apart edges on the second segment with a small gap there between. The second segment was compartmentalized with at least two regions, each region contained a different volume (per unit area) of a temperature sensitive material, such that the peripheral portion of the second segment contained significantly less of the temperature sensitive component than did the inner more portion. The inner more region of the second segment had a shape that was generally similar to that of the bladder. This region also contained the temperature sensitive component, which was a cooling hydrogel that had a freezing temperature below that of water. The second segment was stored in the freezer until use and when removed from the freezer was formable. The second segment included several connections positioned on one of its outward facing surfaces at various points near the periphery; the connections affixed to mating connections on one of the outward facing surfaces of the second segment. The second segment before being affixed to the first segment was shaped by couplers or fasteners positioned near the spaced apart ends and was, by means of the couplers, shaped similar to that of the first segment (thus having one outward facing surface that was recessed near its more center region and an opposing outward facing surface that protruded near its more center region). The second segment had a hole in a centermost region and, when shaped and then affixed to the first segment, the hole in the second segment generally aligned with the hole in the bladder. When the device was secured about the joint, pressure was introduced cyclically into the bladder by a portable pump. The bladder inflated only intermittently and each inflation period compressed only the inner more region of the second segment that was shaped generally similar to that of the bladder. The combination, as described, provided, over time, uniform pressure along the entirety of (or most of) the temperature sensitive component, which translated to a more uniform change in temperature to the underlying tissue (the change directed by the temperature sensitive component). In addition, the combination, as described (sequentially compressing only the temperature sensitive component in an intermittent manner), was found to provide a faster temperature change in the underlying tissue.

It will be understood that while a more uniform compression of the temperature sensitive component may be suitable for some anatomic structures, other anatomic structures may be better suited to have an unequal compression of the temperature sensitive component, which can be readily performed by adjusting the volume (per unit area) of the temperature sensitive component in the second segment while providing a generally uniform pressure across all areas housing the temperature sensitive component.

The described device (offering a generally uniform volume [per unit area] of the temperature sensitive component in the second segment while providing a generally uniform pressure over time across all areas housing the temperature sensitive component) was used to apply intermittent compression to a joint, such as the front of a knee. Representative intermittent compression conditions that achieved a relatively uniform cooling and a fast cooling to the underlying tissue (when the temperature sensitive component was a cooling component and the housing for the temperature sensitive components had a shape that was overlapped by the bladder) are presented in TABLE 2.

TABLE 2

| Pressure (mm | Inflation (sec) | Deflation (sec) |
|---|---|---|
| 50 | 40 | 30 |
| 70 | 35 | 35 |
| 90 | 30 | 40 |

In the conditions provided above, the total time of compression (inflation and deflation) was about 15 minutes. The total time of compression may also be about 16 minutes. Additionally, the total time of compression may be about 10 minutes or about 20 minutes or about 25 minutes or about 30 minutes, or about 60 minutes, or about 90 minutes, or about 120 minutes or several hours. Total time of compression may be shorter or longer depending on the tissue and/or anatomic location. In some embodiments, the temperature sensitive component will determine the total time of compression because of the inherent characteristics of the temperature sensitive component.

While representative pressures are depicted in TABLE 2, it will be understood that other pressure may be used. In one or more embodiments, the period of inflation is the same as the period of deflation. In additional embodiments, the period of inflation is not the same as the period of deflation. The period of inflation may be from about 15 seconds to about 20 seconds, or to about 25 seconds, or to about 30 seconds, or to about 35 seconds, or to about 40 seconds, or to about 45 seconds, or to about 50 seconds, or to about 55 seconds, or to about 60 seconds, or to about 90 seconds, or to about 120 seconds, or from about 20 seconds to about 50 seconds, or from about 25 seconds to about 45 seconds, or from about 30 seconds to about 40 seconds, or from about 15 seconds to about 50 seconds, or may be about 15 seconds, or about 20 seconds, or about 25 seconds, or about 30 seconds, or about 35 seconds, or about 40 seconds, or about 45 seconds, or about 50 seconds. Similarly, the deflation period may be from about 15 seconds to about 20 seconds, or to about 25 seconds, or to about 30 seconds, or to about 35 seconds, or to about 40 seconds, or to about 45 seconds, or to about 50 seconds, or to about 55 seconds, or to about 60 seconds, or to about 90 seconds, or to about 120 seconds, or may be from about 20 seconds to about 50 seconds, or from about 25 seconds to about 45 seconds, or from about 30 seconds to about 40 seconds, or from about 15 seconds to about 50 seconds. Or the deflation period may be about 15 seconds, or about 20 seconds, or about 25 seconds, or about 30 seconds, or about 35 seconds, or about 40 seconds, or about 45 seconds, or about 50 seconds, or about 55 seconds, or about 60 seconds, or about 90 seconds, or about 120 seconds. It is also within the scope of the invention to maintain a minimum or base amount of pressure in one or more of the chambers throughout an inflation and/or deflation period. The compression pressure for inflation may be from about 10 mm Hg to about 100 mm Hg, or may be about 10 mm Hg, or about 15 mm Hg, or about 20 mm Hg, or about 25 mm Hg, or about 30 mm Hg, or about 35 mm Hg, or about 35 mm Hg, or about 40 mm Hg, or about 45 mm Hg, or about 50 mm Hg, or about 55 mm Hg, or about 60 mm Hg, or about 65 mm Hg, or about 70 mm Hg, or about 75 mm Hg, or about 80 mm Hg, or about 85 mm Hg, or about 90 mm Hg, or about 95 mm Hg, or about 100 mm Hg.

In one of many representative arrangements, an apparatus described herein included a pump that inflated air into a bladder positioned within the first segment of the device. The pump delivered intermittent pressure to the bladder in cycles that were pre-set. The pump included three pre-defined settings that delivered air to the bladder for a total time for compression of sixteen minutes, each setting offering a different pressure with a different cycle pattern. The pre-defined settings were similar to those presented in TABLE 2. The pump was housed in a unit small enough to allow it to be handheld, placed in a dedicated wearable pouch or strap, carried in the user's pocket, carried on the user's belt or removably coupled to the exterior of the first segment itself. The pump unit was powered by a battery or by an alternating current. The pump was controlled by a controller, coupled to a valve, pressure gauge, muffler and exhaust mechanism; with a safety pre-set to stop compression if the bladder inflated beyond a predetermined pressure, which, in this embodiment, was 10 mm Hg beyond each pre-defined pressure setting. When the pump inflated a device described herein, the device was compressed sequentially and intermittently from its distal portion to its proximal portion. The sequential flow pushed fluid in the underlying tissue towards the center of the body (trunk) rather than to the periphery of the body.

Additional features that may be combined with a device and components described herein include one or more temperature and/or pressure sensors to provide feedback or alarms for the described device (e.g., pressure and/or temperature on the skin or within parts of the device, itself), a keyboard or push button or other interface to input parameters and data, and microchips or indicators (e.g., LED indicator) that provide a digital or analog readout or display of the pressure or temperature during and after usage of the described device. Optionally a remote unit or external device (wired or wireless, including use of smartphone or other external device) may be provided with the device for remote operation, and to download data and/or applications for use with the device. For example, one or more data programs may be accessed by an external device for specific operation of the device at a specific anatomic body site. As an alternative to an internal source of pressure, the device described herein may be operational with an external source of pressure.

Examples of the described device in operation are provided below. Some examples include alternative (comparative) devices that were unable to achieve the same results as the described device.

In a first example, a compression device described herein, similar to one depicted in FIGS. 1A and 1C, was wrapped round a 4 lb. piece of beef muscle contained in saran wrap. A 2-inch thermometer probe was used to measure temperature of the muscle at its surface, as well as 1 cm, 2 cm, 3 cm and 4 cm below the surface. The compression device was inflated with air and the temperature sensitive component was a hydrogel that had been cooled to 0 degrees F. prior to use. The cooled hydrogel (in its housing) was in contact with the saran wrap. An electric pump introduced intermittent sequential compression to the compression device at a pressure of 50 mm Hg; each cycle included 40 seconds of inflation following by 30 seconds of deflation. The beef muscle was compressed for a total compression time of 15 minutes. The temperature of the beef muscle was measured before application of the device and 15 minutes after application of the device. A control sample (same sized beef muscle) had the same device (with a hydrogel that has been cooled to 0 degrees F.) wrapped about the muscle but without activation of the pump and hence no intermittent compression.

Data showing results with intermittent cold compression as compared with only cold compression are shown in TABLE 3. Each data was an average after performing three separate measurements.

TABLE 3

| | Temperature (F.) | | Temperature (F.) | |
|---|---|---|---|---|
| Depth (cm) | IC (0 min) | No IC (0 min) | IC (15 min) | No IC (15 min) |
| 0 | 66.7 | 67.8 | 41.6 | 53.5 |
| 1 | 66.5 | 67.7 | 46.1 | 56.6 |
| 2 | 66.5 | 67.6 | 49.8 | 58.9 |
| 3 | 66.4 | 67.4 | 52.9 | 60.4 |
| 4 | 66.2 | 67.4 | 55 | 61.3 |

Figure 20:
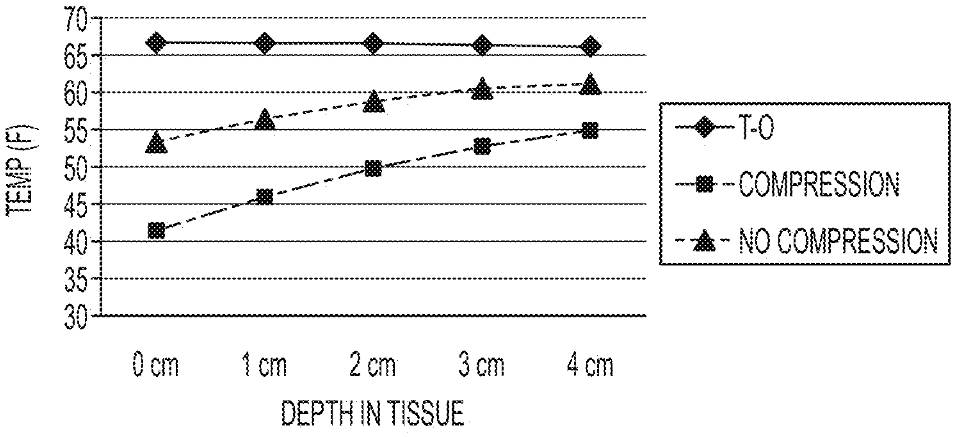
FIG. 20 depicts temperature measurements in a muscle at various muscle depths before treatment (T-O, diamonds), after treatment for 15 minutes with intermittent compression and concomitant temperature (compression, triangles), and after treatment for 15 minutes with the same temperature and no intermittent compression (no compression, squares).

Temperatures well below 50 degrees F. were achieved in muscle tissue that was provided 15 minutes of intermittent cold compression as compared with muscle that was provided only 15 minutes of cold without intermittent compression. With cold alone, the temperature in either the surface tissue or the deeper tissue was never below 53 degrees. This is further exemplified in FIG. 20, in which T-0 is the average of IC (0 min) and No IC (0 min), compression is that which was achieved after 15 minutes of intermittent compression using the cold compression device described herein and no compression is that which was achieved after 15 minutes of the cold device without intermittent compression.

In another example, the described device, similar to one depicted in FIGS. 1A and 1C, was compared with a comparative cold compression device that does not apply intermittent compression. The comparative device (Moji Knee, by Moji, Inc., Glenview, Ill.) is a two-piece design with an outer wrap that surrounds the front of the knee joint having upper and lower stretchable (migratable) straps that each wrap around the leg (above and below the knee, each strap connecting back to the front of the wrap). A second piece is an interior cold cell unit with about 20 independent cold cells that are physically separated from each other and surround the front and sides of the knee joint.

The described device had a hydrogel that had been cooled to 0 degrees F. prior to use. The cold cell unit of the comparative device was also initially cooled to 0 degrees Fahrenheit before use. Both the described device and the comparative device were positioned on one knee of the same person. Treatment time was 16 minutes for both devices; however, the described device was also compressed intermittently via an air pump for 10 cycles of compression at 50 mm Hg that included 45 seconds of inflation and 30 seconds of deflation. Both devices were removed after the 16 minute treatment time. Skin temperature was measured on the inner side of the knee just below the patella and oxygenation was measured on the inner and outer sides just below the patella; all measurements were taken at 0 minutes, 16 minutes, 31 minutes and 60 minutes after treatment initiation. To obtain oxygenation measurements, a near infrared spectroscopy unit (InSpectra™ Monitor, model 650, a trademark of Hutchinson Technology Incorporated, Minnesota) was used.

Immediately after application of compression, both devices were removed and the knees were visualized as well as photographed. The left knee, to which the described invention was positioned, showed more visible redness, pointing to increased blood flow. Further data is shown in TABLE 4. Each data was an average after performing three separate measurements.

TABLE 4

| Time | Skin Temperature (F.) | | Oxygenation (inner knee) | | Oxygenation (outer knee) | |
|---|---|---|---|---|---|---|
| (min) | IC | No IC | IC | No IC | IC | No IC |
| 0 | 82.4 | 81.9 | 53 | 57 | 62 | 62 |
| 16 | 49.1 | 71.8 | 85.5 | 52 | 87 | 58 |
| 31 | 58.9 | 72.2 | 80 | 50 | 85 | 55 |
| 60 | 66.9 | 74.4 | 53 | 50 | 71 | 62 |

Figure 21:
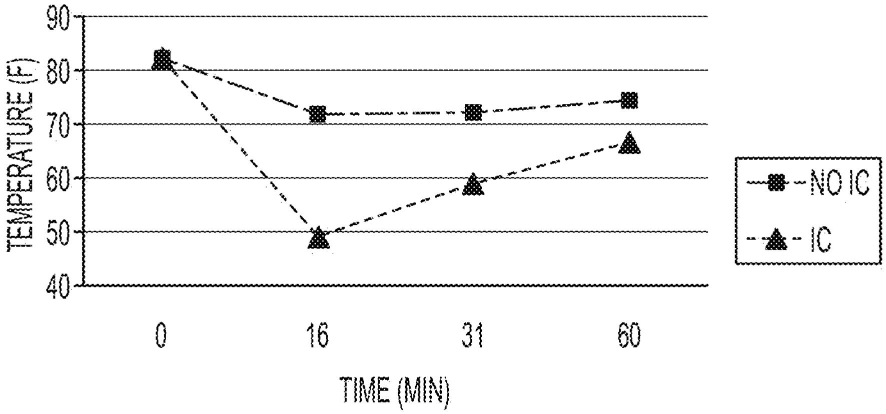
FIG. 21 depicts temperature measurements taken at various time points at the knee when provided with a representative device described herein (IC, triangles) as compared with a comparative device (No IC, squares).
Figure 22:
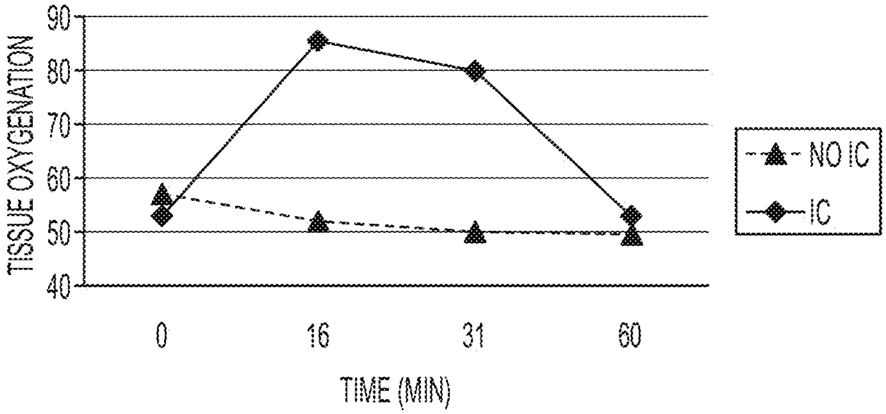
FIG. 22 depicts tissue oxygenation measurements taken at various time points at the knee when provided with a representative device described herein (IC, diamonds) as compared with a comparative device (No IC, triangles).
Figure 23:
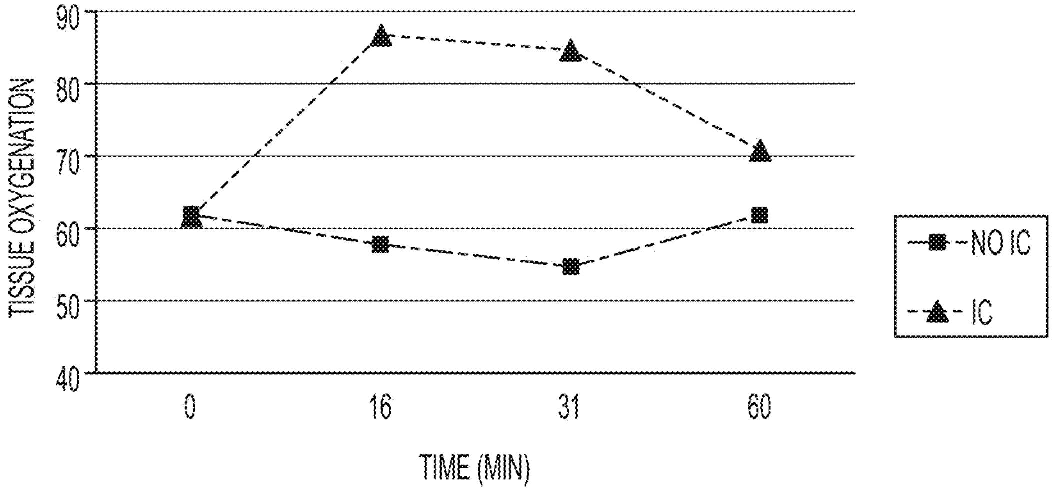
FIG. 23 depicts additional tissue oxygenation measurements taken at various time points at the knee when provided with a representative device described herein (IC, triangles) as compared with a comparative device (No IC, square).

Results differed when a knee was provided intermittent cold compression with a device described herein as compared with only cold compression using a comparative device. For example, tissue near the knee reached a temperature of 49.1 degrees F. when treated with the described device (IC) and only reached a temperature of 71.8 degrees F. when treated with the comparative device (No IC). In addition, tissue oxygenation near the inner side of the knee increased by 61% when treated with the described device (IC) as compared with no apparent effect with the comparative device (No IC). The same was found with the outer side of the knee, which showed an increase in oxygenation of 40% after treatment with the described device (IC) as compared with no apparent effect after treatment with the comparative device (No IC). This is also exemplified in FIGS. 21-23, which show that the lowest skin temperatures and highest oxygenation amounts were achieved with application of the device described herein, which included a temperature cooling material combined with application of intermittent compression directed site specifically.

In a further example, a device described herein, similar to one depicted in FIGS. 1A and 1C, was compared with a comparative device that applies intermittent compression in a different manner and non-site specifically. The described device had a hydrogel that had been cooled to 0 degrees F. prior to use. The comparative device (Game Ready® Knee Wrap; a trademark of CoolSystems, Inc., Concord, Calif.) is a water cooled compression wrap that encircles a large portion of the leg from above the ankle to mid-thigh. The comparative device circulates over the entire wrap cold or ice water in an inner chamber and has an outer air chamber that inflates and deflates air over the entire wrap at a fixed pressure setting. The described device was positioned on one knee of a person and the comparative device was positioned on the other leg of the same person. Both devices were activated for sixteen minutes and then removed thereafter. The described device was pre-programmed for 10 cycles, each including compression for 45 seconds and deflation for 30 seconds at a pressure of 50 mm Hg. The comparative device was wrapped around the entire leg and set to its maximum cold setting and a medium compression setting. Skin temperature was measured on the inner side of the knee just below the patella and oxygenation was measured on the inner and outer sides just below the patella; all measurements were taken at 0 minutes, 16 minutes, 31 minutes, 46 minutes and 60 minutes following treatment initiation. To obtain oxygenation measurements, a near infrared spectroscopy unit (InSpectra™ Monitor, model 650, a trademark of Hutchinson Technology Incorporated, Minnesota) was used.

Immediately after application of compression, both devices were removed and the knees were visualized as well as photographed. The left knee, to which the described invention was positioned, showed more visible redness, pointing to increased blood flow. Additional data are presented in TABLE 5. Each data was an average after performing three separate measurements. The described device achieved a lower tissue temperature about the knee. In addition, the described device improved oxygenation about the knee.

TABLE 5

| Time | Skin Temperature (F.) | | Oxygenation (inner knee) | | Oxygenation (outer knee) | |
|---|---|---|---|---|---|---|
| (min) | IC-knee | IC-leg | IC-knee | IC-leg | IC-knee | IC-leg |
| 0 | 82.4 | 82.25 | 67 | 61 | 68 | 65.5 |
| 16 | 49.1 | 61.8 | 92.5 | 58 | 89.5 | 73.5 |
| 31 | 58.9 | 67.1 | 92 | 55 | 82 | 64 |
| 46 | 66.9 | 71.2 | 71 | 48 | 71 | 58 |
| 60 | 68.8 | 72.7 | 56 | 45 | 55 | 54 |

Figure 24:
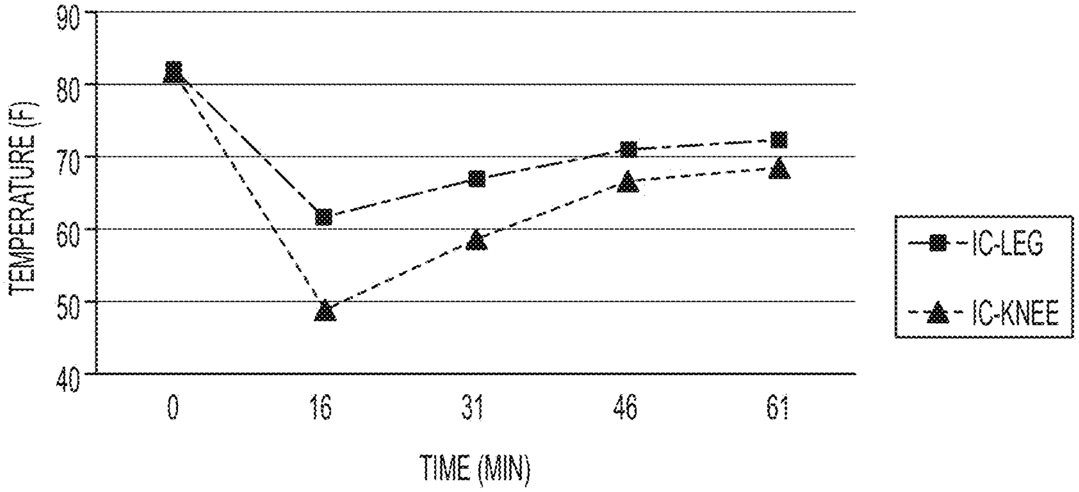
FIG. 24 depicts temperature measurements taken at various time points at the knee when provided with a representative device described herein (IC-knee, triangles) as compared with a comparative device (IC-leg, square).
Figure 25:
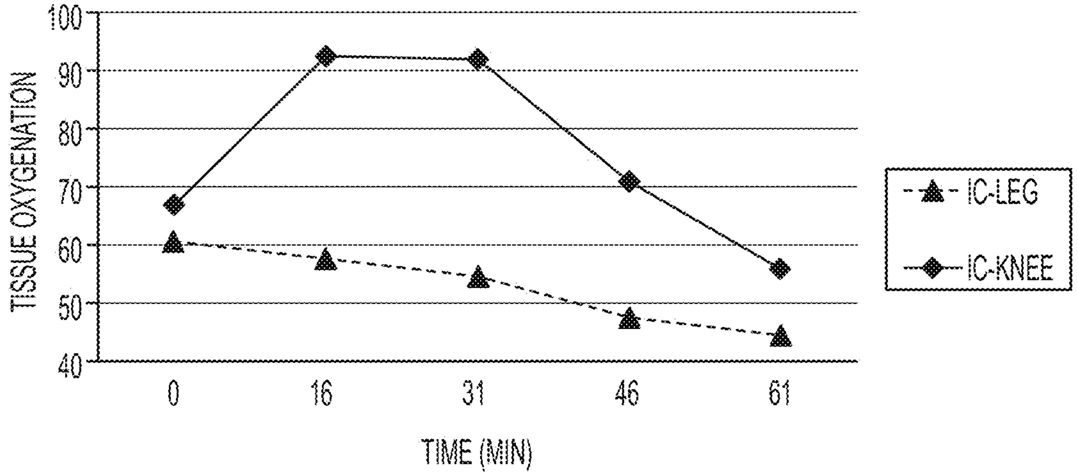
FIG. 25 depicts tissue oxygenation measurements taken at various time points at the knee when provided treatment with a device described herein (IC-knee, diamond) as compared with a comparative device (IC-leg, triangles).
Figure 26:
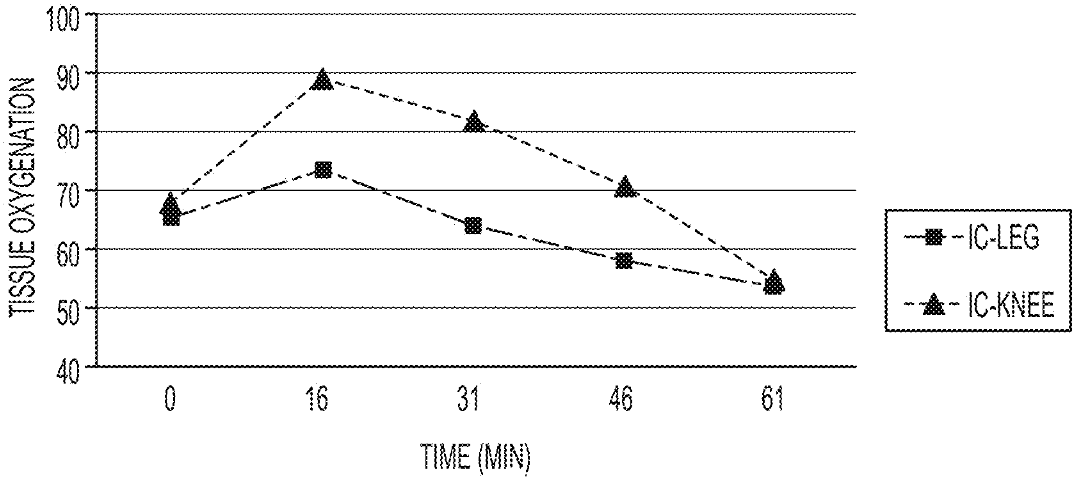
FIG. 26 depicts additional tissue oxygenation measurements taken at various time points at the knee when provided treatment with a device described herein (IC-knee, triangles) as compared with a comparative device (IC-leg, squares).
Figure 27:
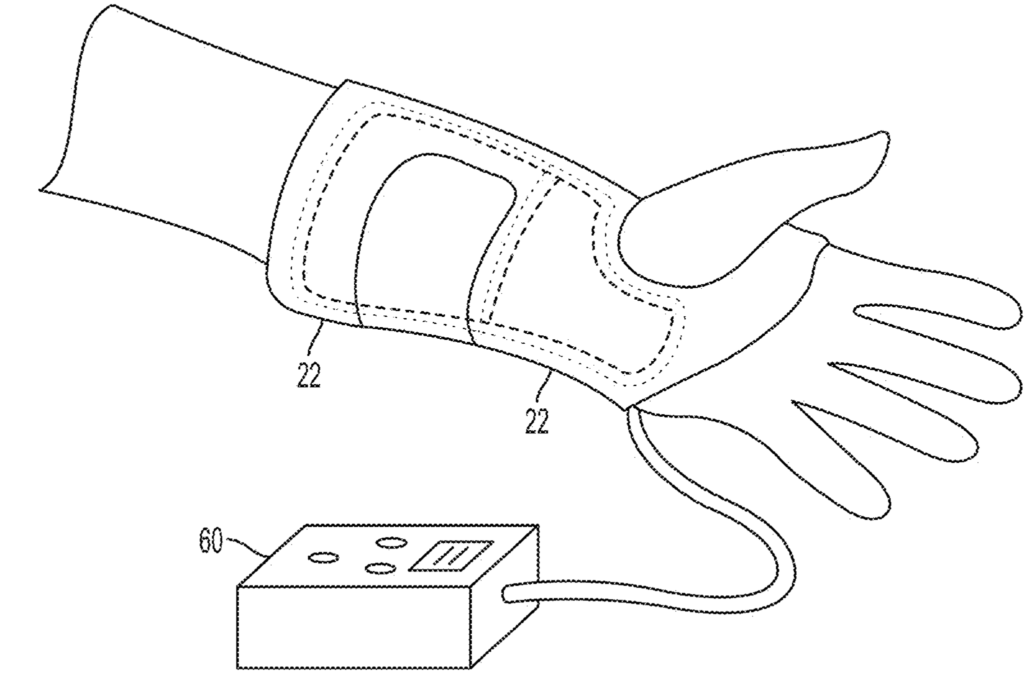
FIGS. 27-30 depict further representative devices on anatomic structures as described herein.

This is further exemplified in FIGS. 24-26, which, together, show that lower tissue temperatures and higher oxygenation amounts were achieved with application of the device described herein by providing site specifically with intermittent compression a temperature cooling material at a desired temperature, likely cooler than the comparative device. Tissue oxygenation measured at the inner side of the knee increased by 38% with the described device (IC-knee) as compared to no apparent effect recorded after use of the comparative device (IC-leg). Tissue oxygenation measured at the outer side of the knee increased by 32% with the described device (IC-knee) as compared to no apparent effect recorded after use with the comparative device (IC-leg).

Figure 28:
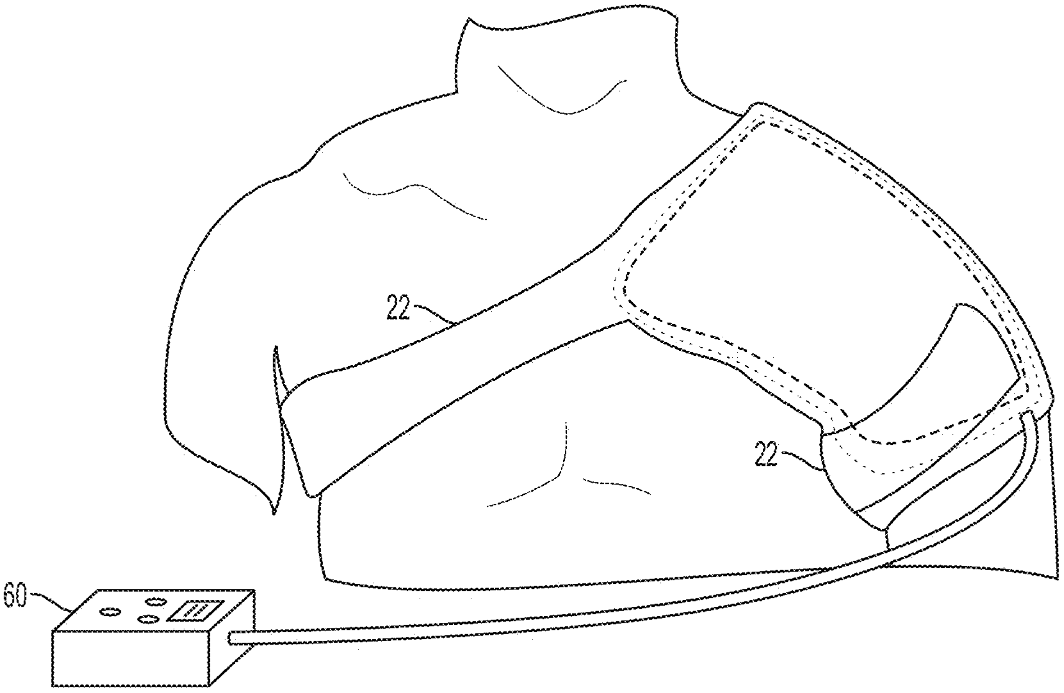
Figure 29:
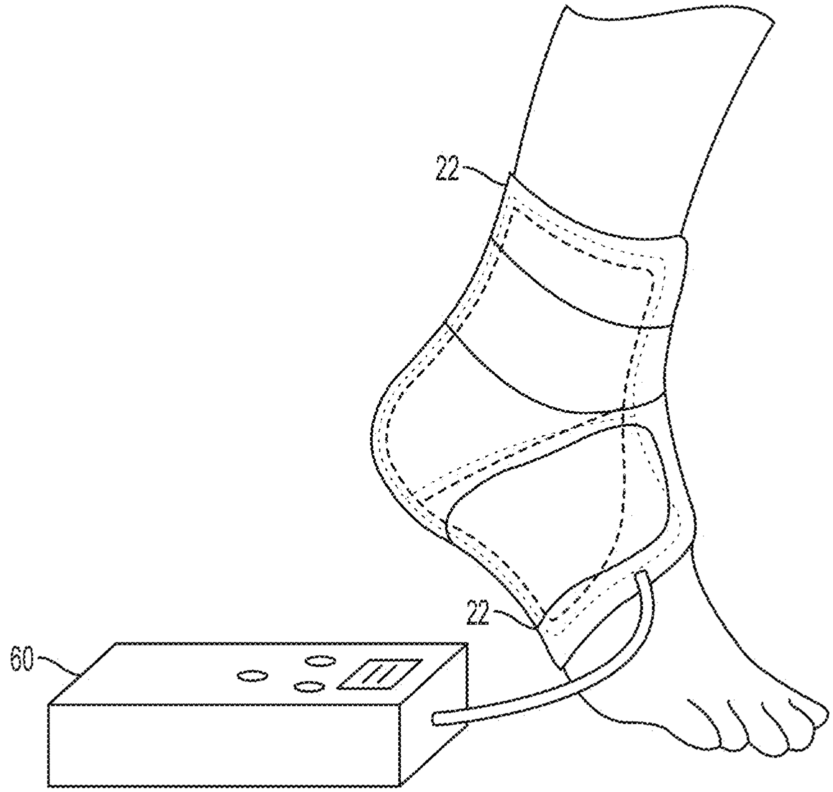

FIGS. 27-36 show representative devices for positioning around other anatomic structures of the body, including the wrist (FIG. 27, FIGS. 36A-36F), shoulder (FIG. 28; FIGS. 35A-35F), ankle (FIG. 29; FIGS. 31A-31F), knee (FIGS. 33A-33E), leg, (FIGS. 34A-34F), and elbow (FIG. 30; FIGS. 32A-32E). In these representative embodiments, the temperature sensitive component or elements are housed in a second segment that is smaller or slightly smaller in overall size (see outline in dashed lines) than the bladder (see outline in dotted lines), such as when viewed in a front view. Similarly, the bladder, when configured to fit within the interior of the first segment, was smaller or slightly smaller in overall size (see outline in dashed lines) than the overall size of the first segment, such when viewed in a front view. The bladder, when configured to fit within the interior of the first segment will often encompass much of the body, excluding the extensions or areas used for fastening or securing the device in position or for securing on the limb or the trunk.

In FIGS. 27-30, the device is shown in use when positioned on a portion of the body in need thereof. In FIGS. 31-36, representative devices for the ankle, elbow, knee, leg, shoulder, and wrist are shown, such that each component of these exemplary devices have been separated for a more detailed viewing of parts and illustrated when flat and not positioned for use. FIGS. 31A, 32A, 33A, 34A, 35A and 36A each depict front views of the first outer facing surface (outside when positioned for use), while FIGS. 31B, 32B, 33B, 34B, 35B and 36B, each depict front views of the second outer facing surface (inside when positioned for use). FIGS. 31C, 32C, 33C, 34C, 35C and 36C each depict a front view of one of the facing surfaces of the bladder. FIGS. 31D, 32D, 33D, 34D, 35D and 36D each depict a side view of the bladder, showing elements therein. FIGS. 31D, 32D, 33D, 34D, 35D and 36D each depict a front view of one of the facing surfaces of the second segment. FIGS. 31F, 34F, 35F and 36F each depict a side view of the second segment.

Figure 30:
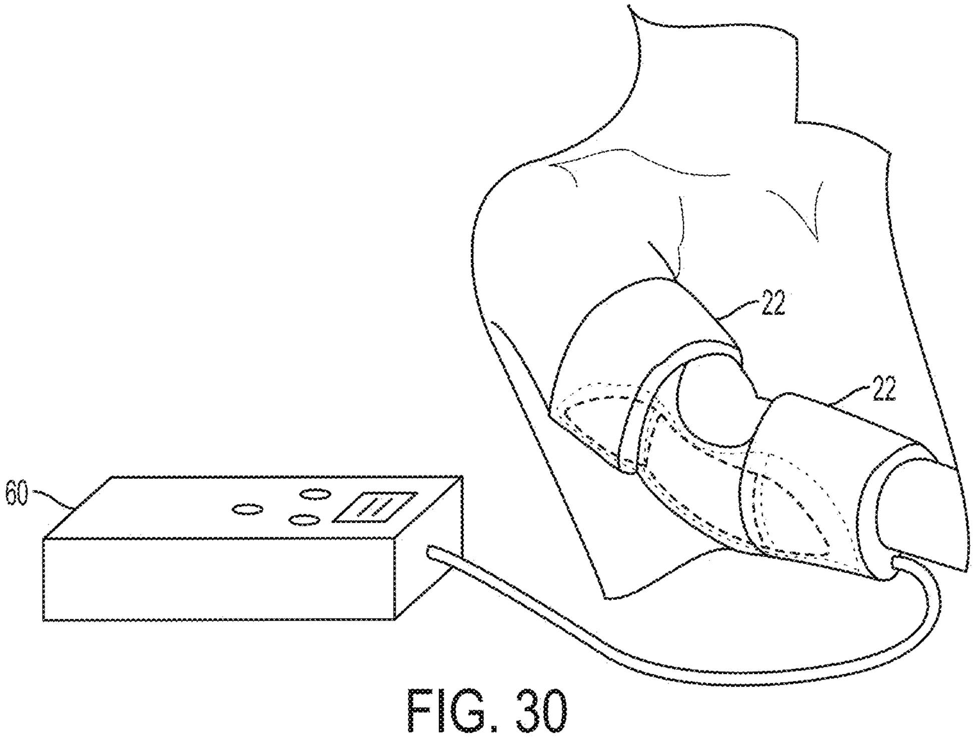
Figure 31B:
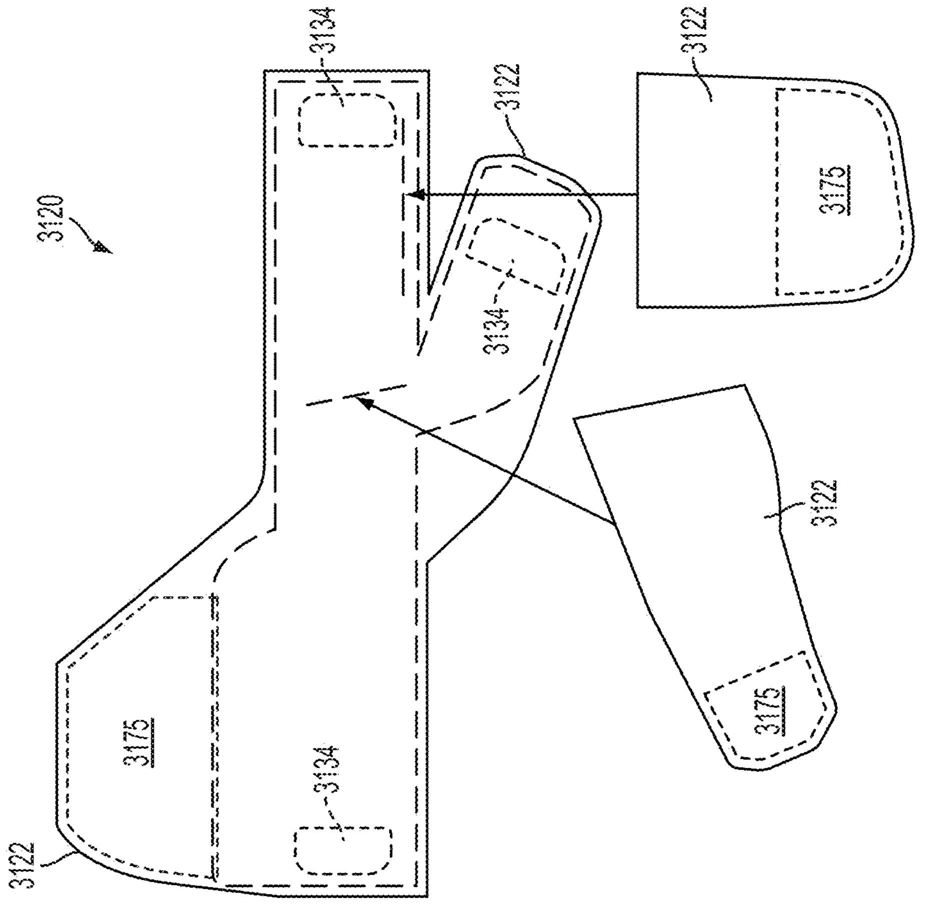
FIGS. 31A-31F depict a representative device and components thereof for positioning on a portion of the body, such as the ankle.
Figure 31C:
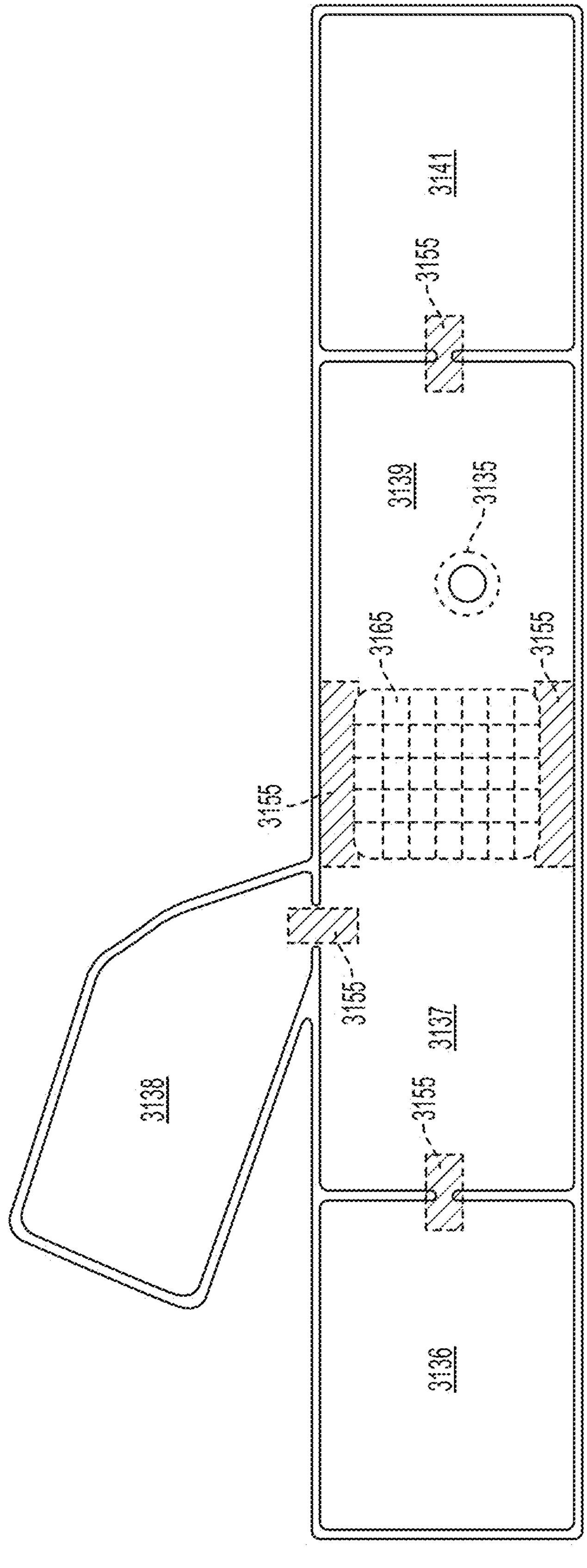
Figure 31E:
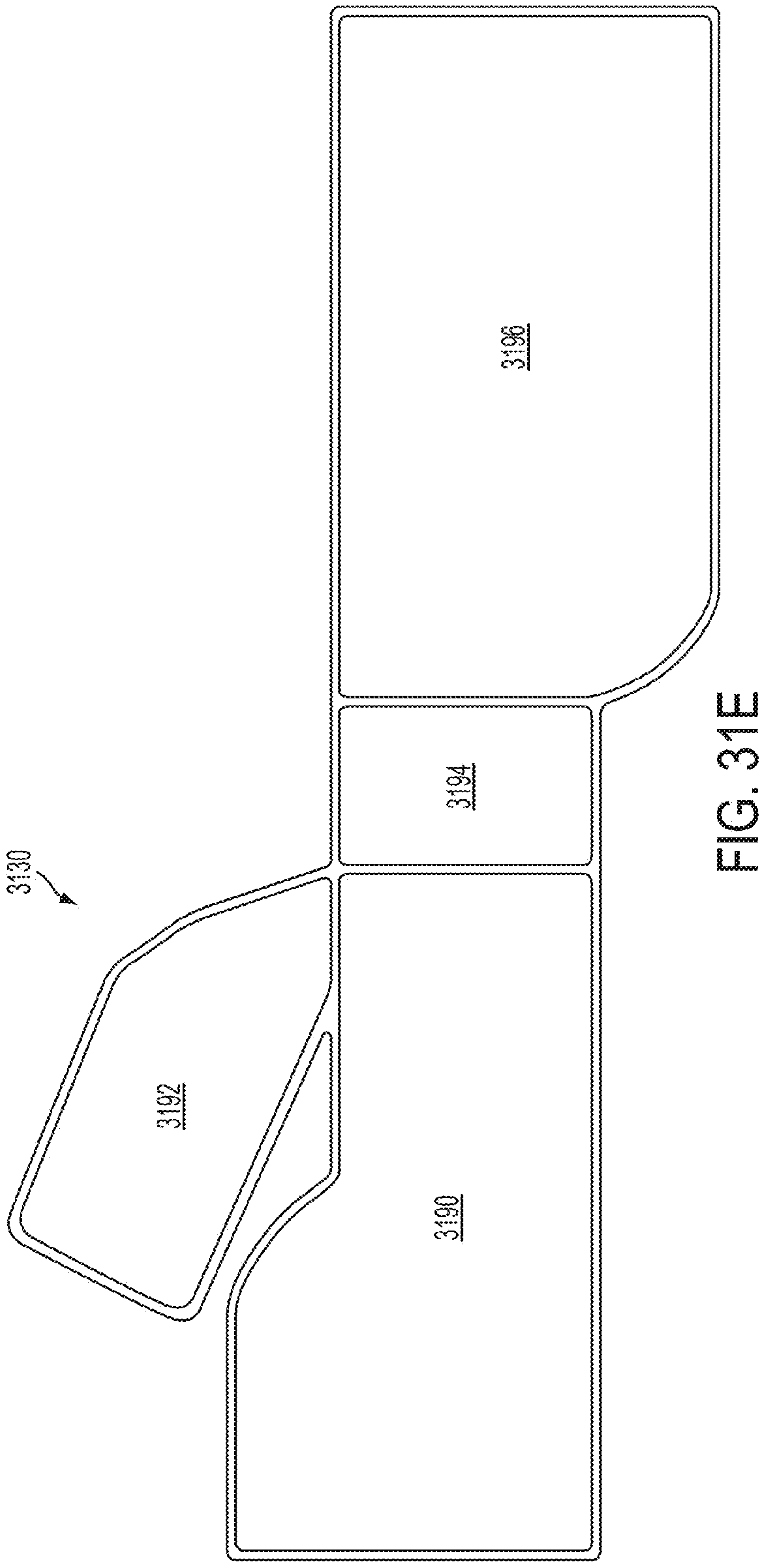
Figure 32B:
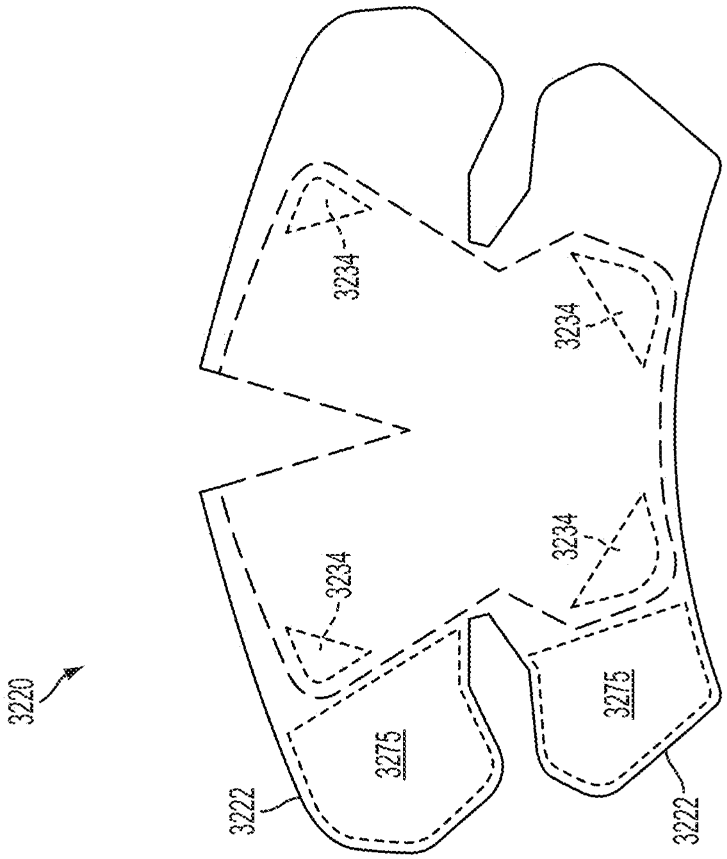
FIGS. 32A-32E depict representative device and components thereof for positioning on a portion of the body, such as the elbow.
Figures 35A, 35B:
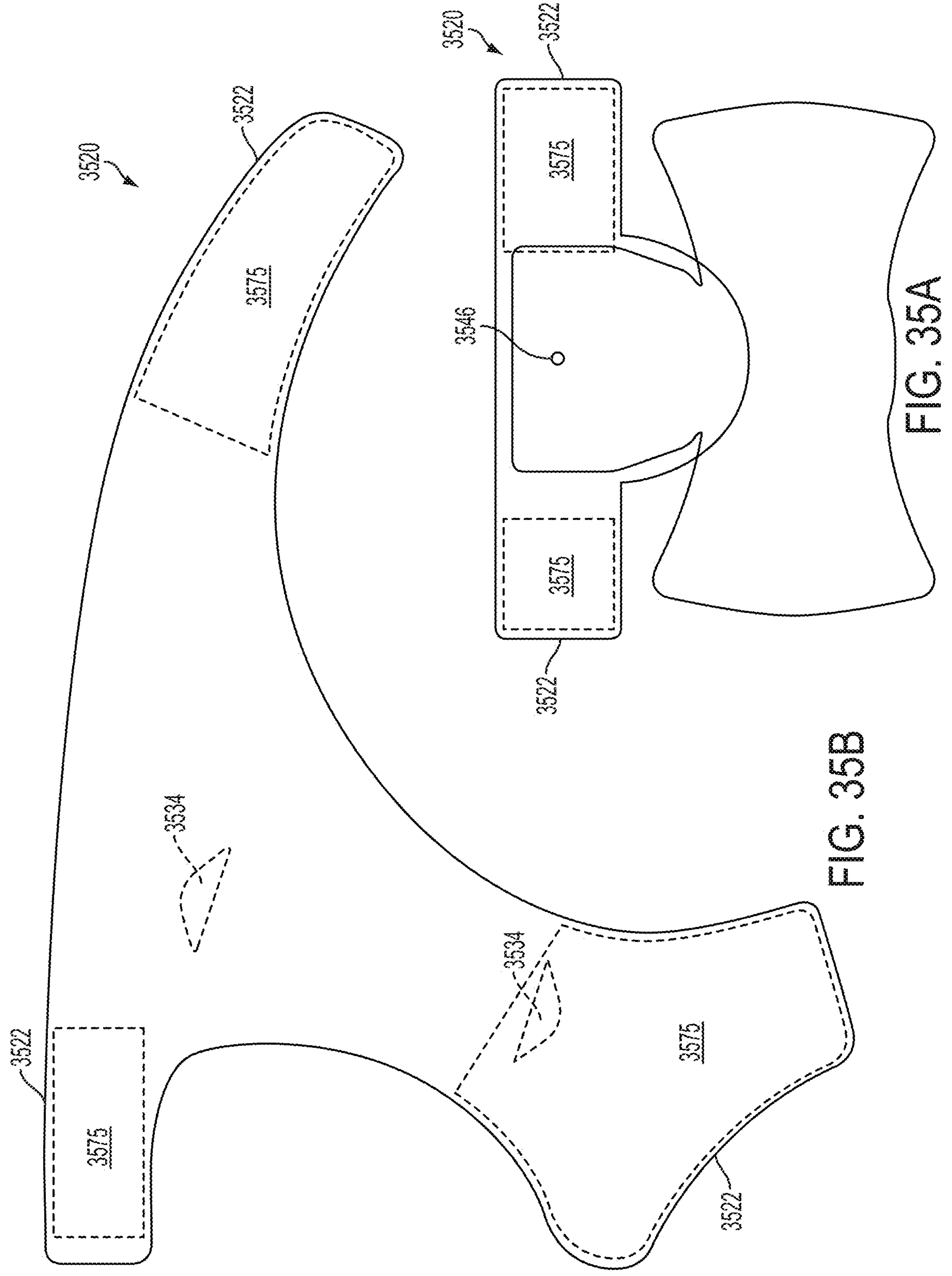
FIGS. 35A-35F depict representative device and components thereof for positioning on a portion of the body, such as the shoulder.
Figure 35C:
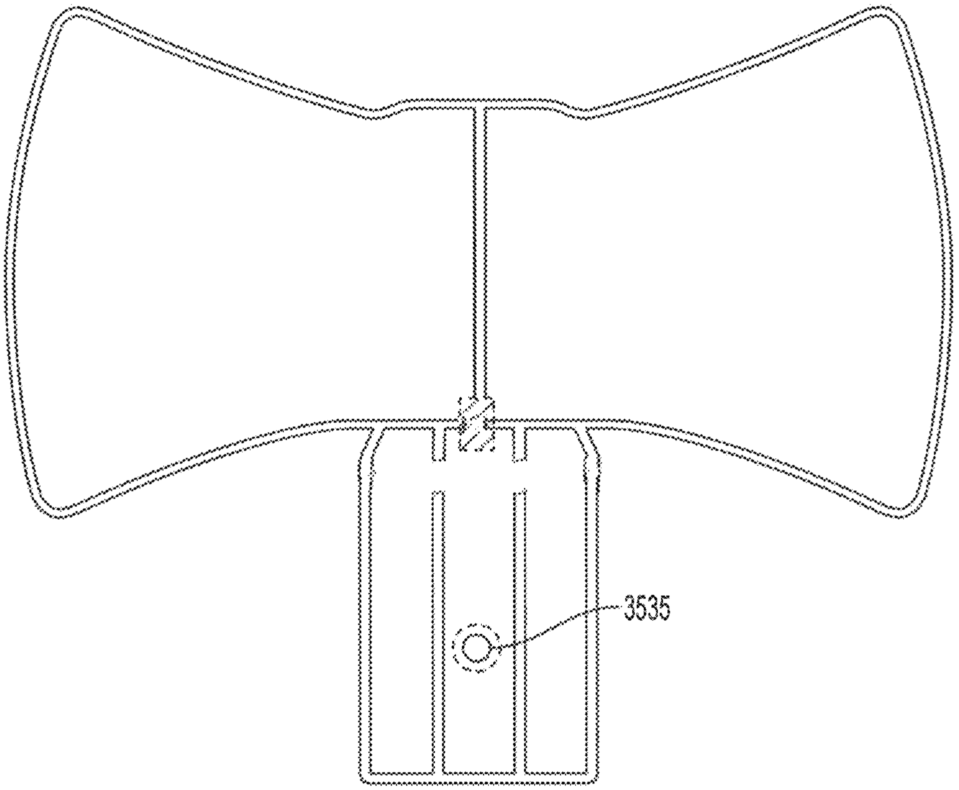
Figure 35D:
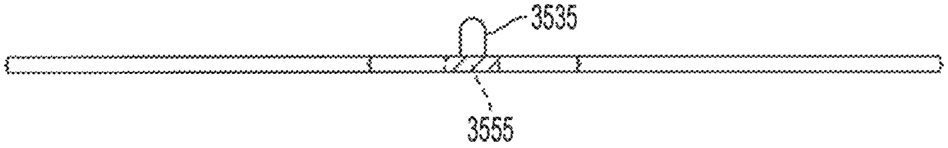
Figure 35E:
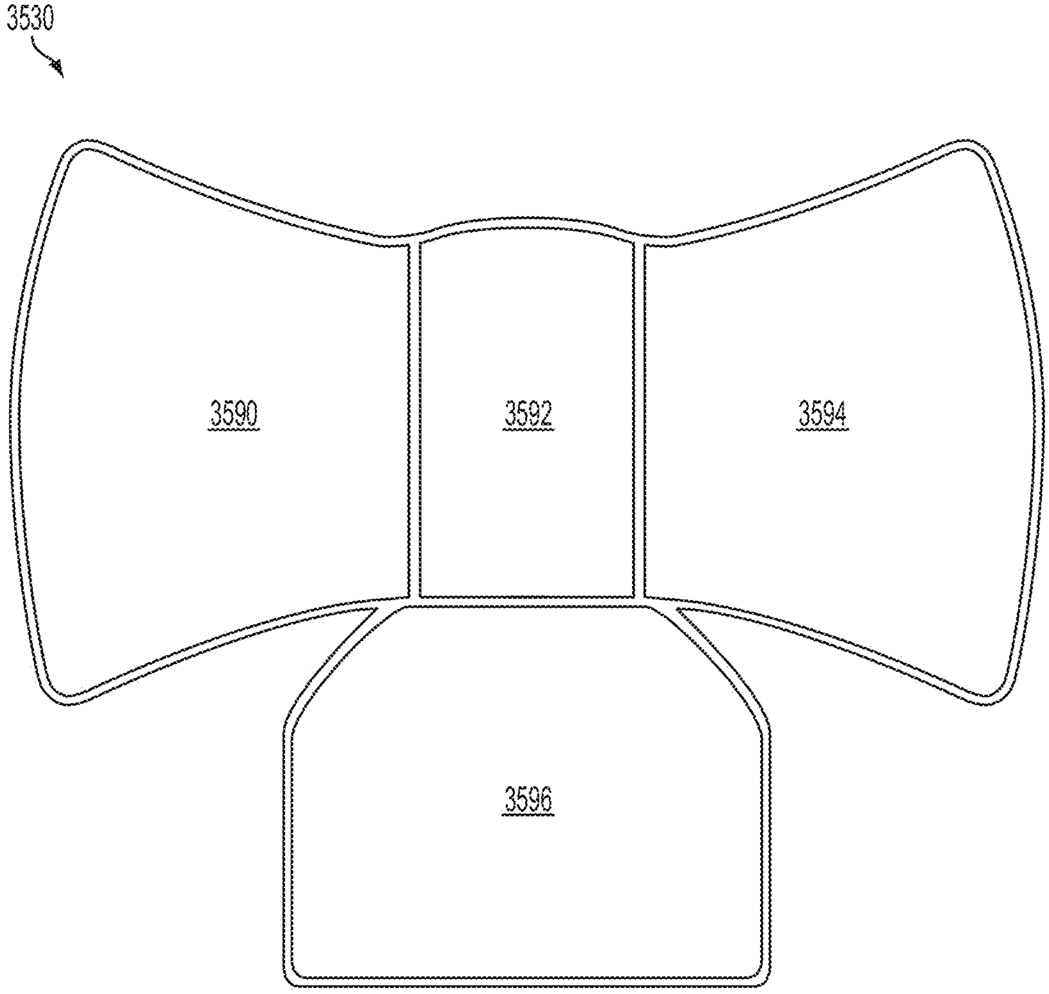

FIGS. 27 and 29, and FIGS. 36A and 36C show that each of the housings for the temperature sensitive component and the bladder are defined by two compartments or chambers. FIG. 28 shows that the housing for the temperature sensitive component and the bladder are defined by one compartment or chamber. On the other hand, a similar device for the shoulder may have the temperature sensitive component and the bladder defined by more than one compartment or chamber (FIGS. 35C and 35E). In fact, the number of compartments or chambers does not need to be the same for the housing for temperature sensitive components as for the bladder. For example, a bladder may be configured to include two compartments (FIG. 35C) while the second segment compatible with the same device may be configured to include 3 or 4 compartments (FIG. 35E). Furthermore, the different compartments for the temperature sensitive component may include the same or differing amounts of the temperature sensitive component. FIGS. 30, 33C and 33D show that each of the housing for the temperature sensitive component and the bladder are defined by three compartments or chambers. On the other hand, FIGS. 32C and 32E show that a representative device for the elbow may also be defined by two compartments or chambers. FIGS. 33C and 33E show that housing for each of the temperature sensitive component and the bladder may be defined by more than three compartments. In this embodiment, the temperature sensitive component is defined by four components or chambers in the second segment (FIG. 33E). In addition, the amount of the temperature sensitive component may vary, such that the amount in the compartment nearest the center of the device may be greater than the amount contained in the compartments farthest from the center of the device (e.g., near the periphery). FIGS. 31C and E show that housings for the temperature sensitive components and the bladder may be defined by different numbers of compartments. For example, the housing for the temperature sensitive component may be defined by four compartments (FIG. 31E), while the housing for the bladder may be defined by five compartments (FIG. 31C). Each of said representative embodiments shows one of many representative designs that may further include additional features, such as added extension elements and source, as well as additional securing elements or features (cut-outs, inserts, foldings, darting, etc.) that facilitate anatomic shaping of the device while also aiding in the prevention of movement of the device while positioned and in use.

Figure 31A:
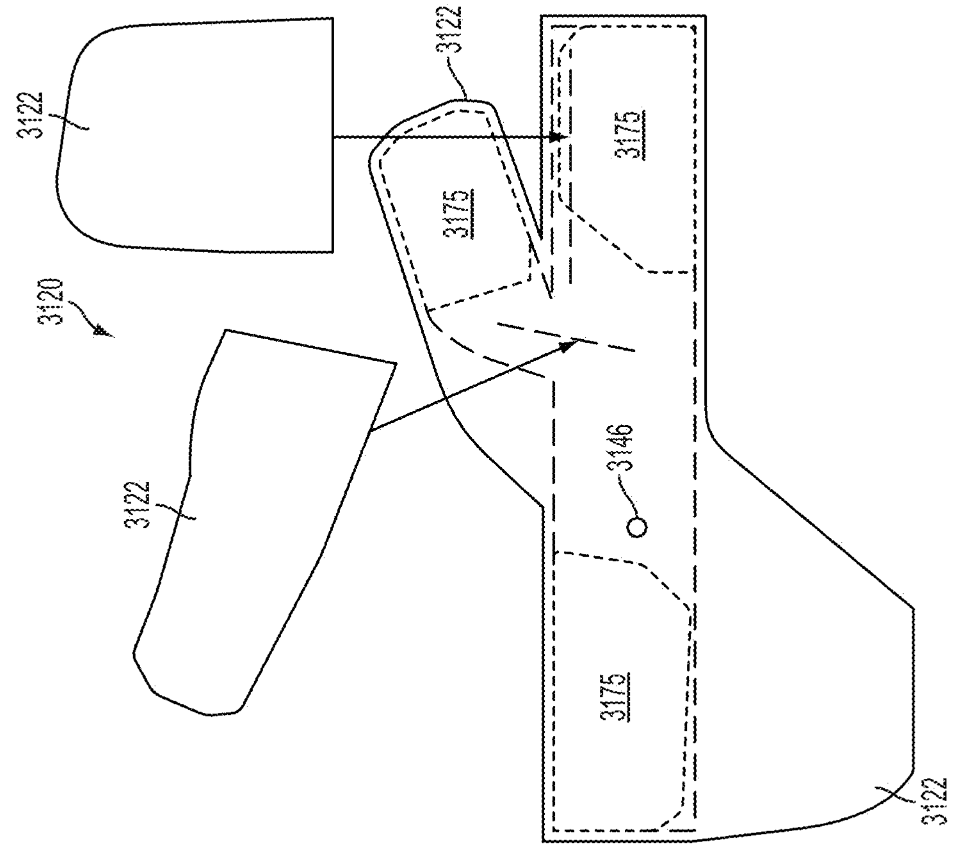
Figure 31D:
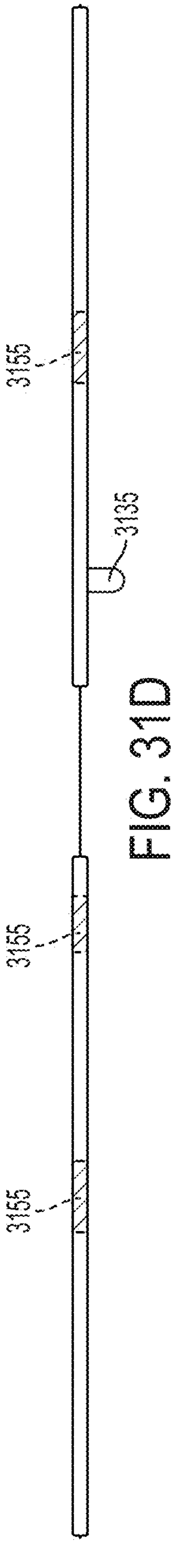
Figure 31F:
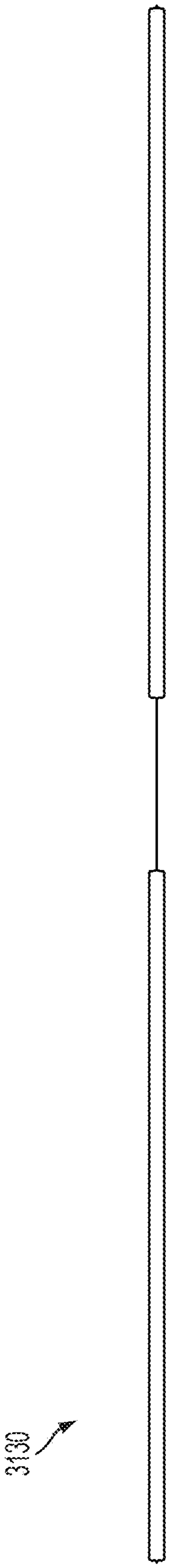

Referring to the representative device and components thereof for the ankle, FIG. 31A illustrates the first segment 3120, outside facing surface, with representative locations for the inlet 3146 (for positioning the fill port 3135 on the bladder), extensions 3122, and securing elements 3175 (such as hooks) for securing and mating the extensions. FIG. 31B illustrates the first segment 3120, inside facing surface, showing representative locations for securing elements 3175 (such as loops) for securing and mating the extensions, and securing elements 3134 for securing the second segment. The inside and outside facing surfaces depicted in FIGS. 31A-31B are sewn or otherwise adhered together at or near its outermost edges (e.g., at or near its periphery), thereby forming an interior space, and so that the outside facing surface is an exterior surface when positioned for use and the inside facing is an interior surface of the first segment when positioned for use. The long dashed lines in FIG. 31A illustrate the relative position for the bladder. The long dashed lines in FIG. 31B illustrate the relative position for the second segment, when included. As shown in FIG. 31C, in this embodiment, the bladder is configured into five compartments or chambers 3136, 3137, 3138, 3139 and 3141, such that with fluid (e.g., air) entering fill port 3135, section 3139 and 3137 and 3138 will fill first followed by 3141 and 3136. Some compartments may be separated by a separation zone 3165, as a noninflatable or non-expanding region, utilizing a noninflatable or non-expanding material, such as a mesh. This is particularly useful for sensitive regions, such as the back of the ankle (near Achilles tendon). At various locations, a filler material 3155, e.g., a porous material or foam, may be included, between compartments to allow flow there between. The filler material assists in maintaining an opening between compartments and is generally positioned in a space provided along a seam line formed between compartments. FIG. 31D shows fill port 3135. FIG. 31E illustrates the second segment 3130, that is optional, and designed for removable fitting with first segment 3130, thus can be attached and detached from the first segment as desired. In the embodiment of FIG. 31E, the second segment is shown as being configured with four compartments, 3190, 3192, 3194, and 3196. Said compartments may be filled with a similar amount of the temperature sensitive component per unit area, or may have different amounts of the temperature sensitive component per unit area. In this embodiment, compartment 3194 is not be filled with a temperature sensitive component, as is depicted in FIG. 31F. The back facing side of second segment 3130 (not shown) will have securing elements that mate with those on the inside facing surface of first segment 3120 depicted in FIG. 31B, mating with securing elements 3134. Said securing elements on the second segment may be heat sealed or otherwise securely and permanently adhered to the second segment.

Figure 32A:
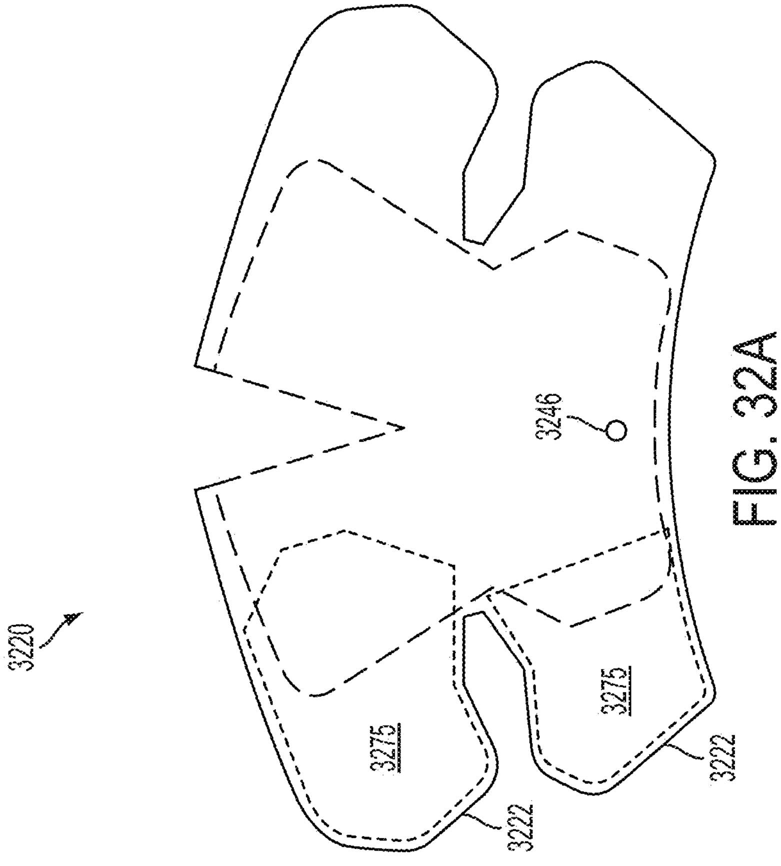
Figure 32C:
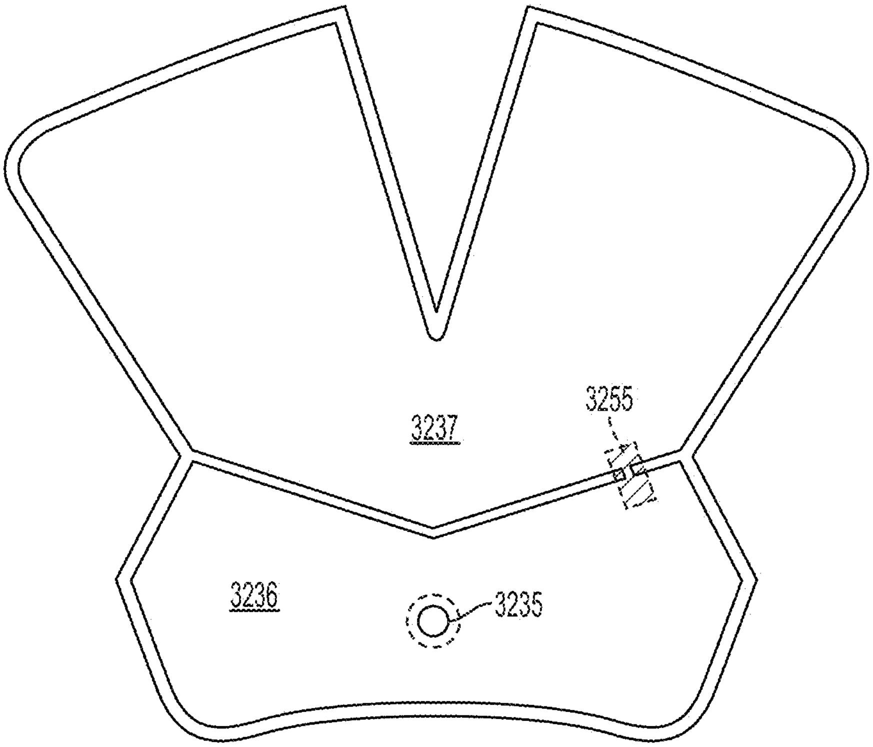
Figure 32D:
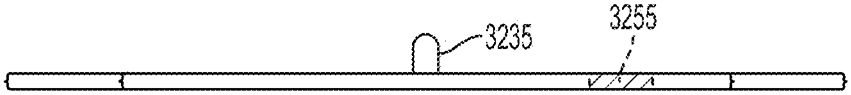
Figure 32E:
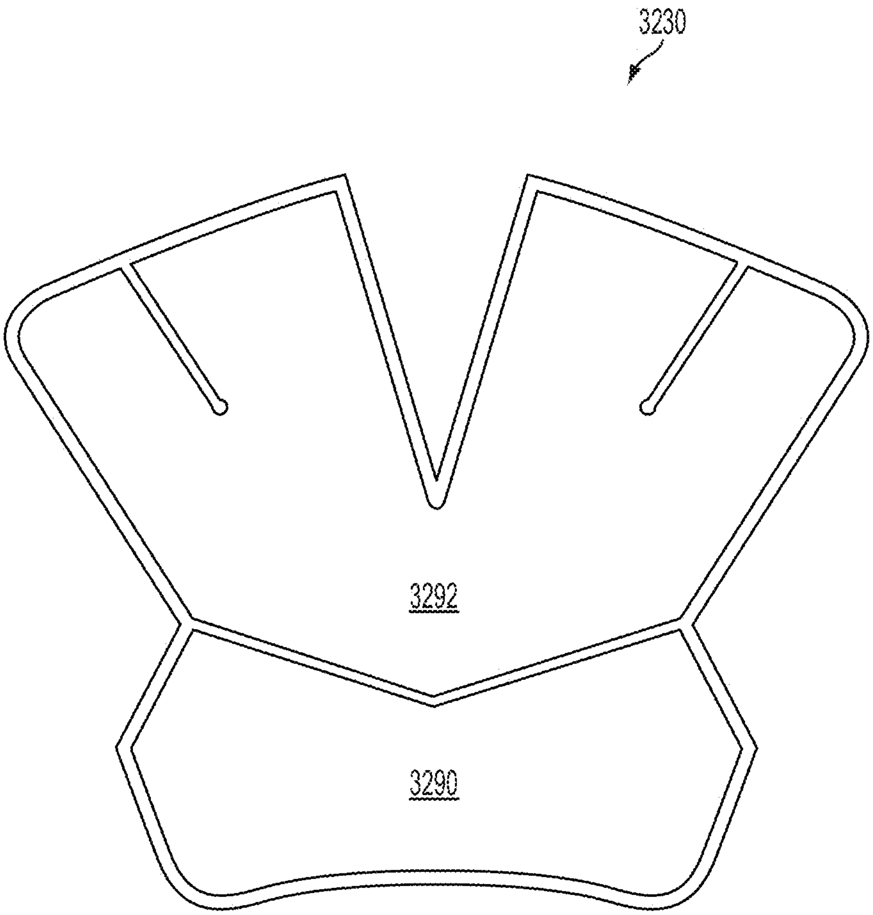

For the representative device for the elbow, FIG. 32A illustrates the outside facing surface of the first segment 3220 with representative locations for the inlet 3246 (for positioning the fill port 3235 on the bladder), extensions 3222, and securing elements 3275 (such as hooks) for securing and mating the extensions. FIG. 32B illustrates the inside facing surface of the first segment 3220, showing representative locations for securing elements 3275 (such as loops) for securing and mating with the extensions, and securing elements 3234 for securing with the second element, when desired. The inside and outside facing surfaces depicted in FIG. 32A and in FIG. 32B are sewn or otherwise adhered together at or near its outermost edges (e.g., at or near its periphery), thereby forming an interior space, and so that the outside facing surface is an exterior surface when positioned for use and the inside facing is an interior surface of the first segment when positioned for use. The long dashed lines in FIG. 32A illustrate the relative position for the bladder. The long dashed lines in FIG. 32B illustrate the relative position for the second segment, when included. As shown in FIG. 32C, in this embodiment, the bladder is configured into two compartments 3236 and 3237, such that with fluid entering fill port 3235, section 3236 will fill first, followed by 3237. A filler material 3255, e.g., a porous material or foam, is included for providing flow from compartment 3236 and 3237. FIG. 32D shows a fill port 3235. The filler material assists in maintaining an opening between compartments and is generally positioned in a space provided along a seam line formed between compartments. FIG. 32E illustrates the optional second segment or leakproof element 3230, in which, in this embodiment, the segment is configured with two compartments, 3290 and 3292. Said compartments may be filled with a similar amount of the temperature sensitive component per unit area, or may have different amounts of the temperature sensitive component per unit area. In this embodiment, compartments for the second segment are generally compatible with and configured to have a similar shape as the compartments housed in the bladder. The back facing side of second segment 3230 (not shown) will have securing elements that mate with and can detach from those securing elements 3234 on the inside facing surface of first segment 3220 depicted in FIG. 32B. Said securing elements on the second segment may be heat sealed or otherwise securely and permanently adhered to the second segment.

Figure 33A:
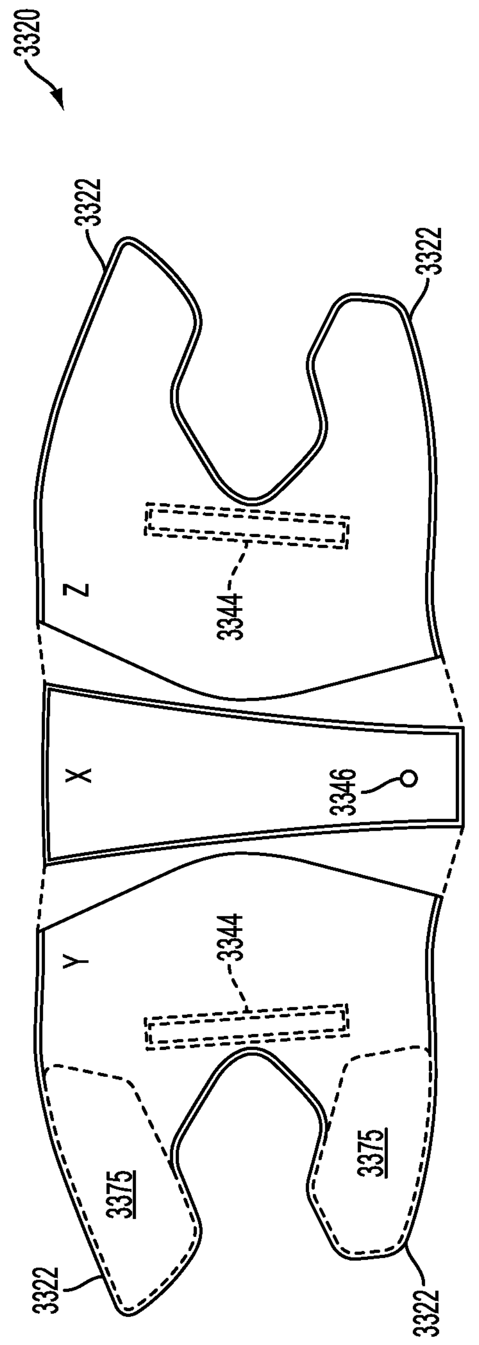
FIGS. 33A-33E depict representative device and components thereof for positioning on a portion of the body, such as the knee.
Figure 33B:
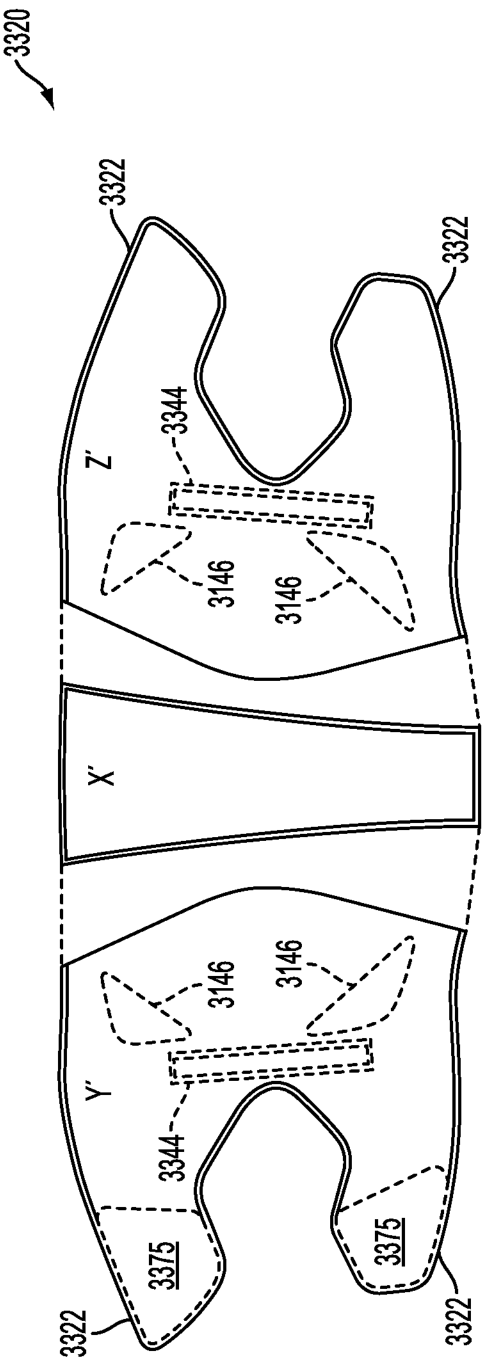
Figure 33C:
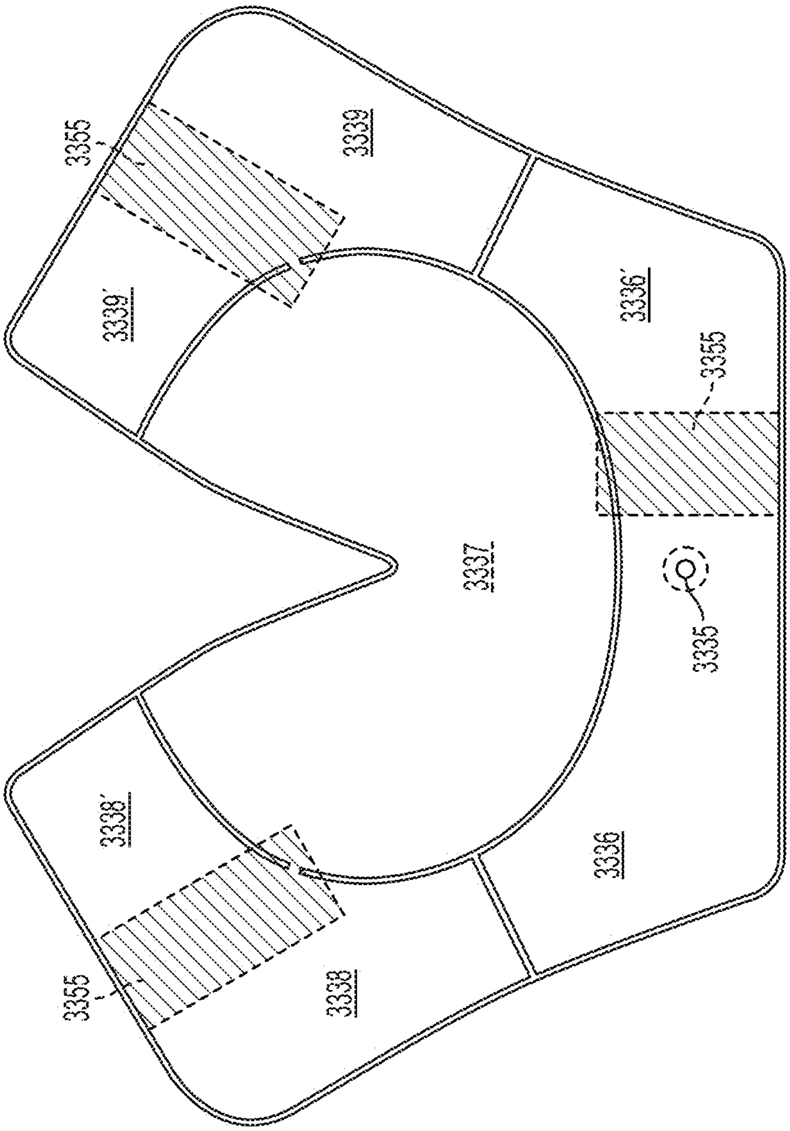
Figure 33D:
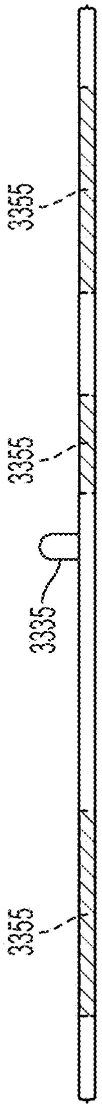
Figure 33E:
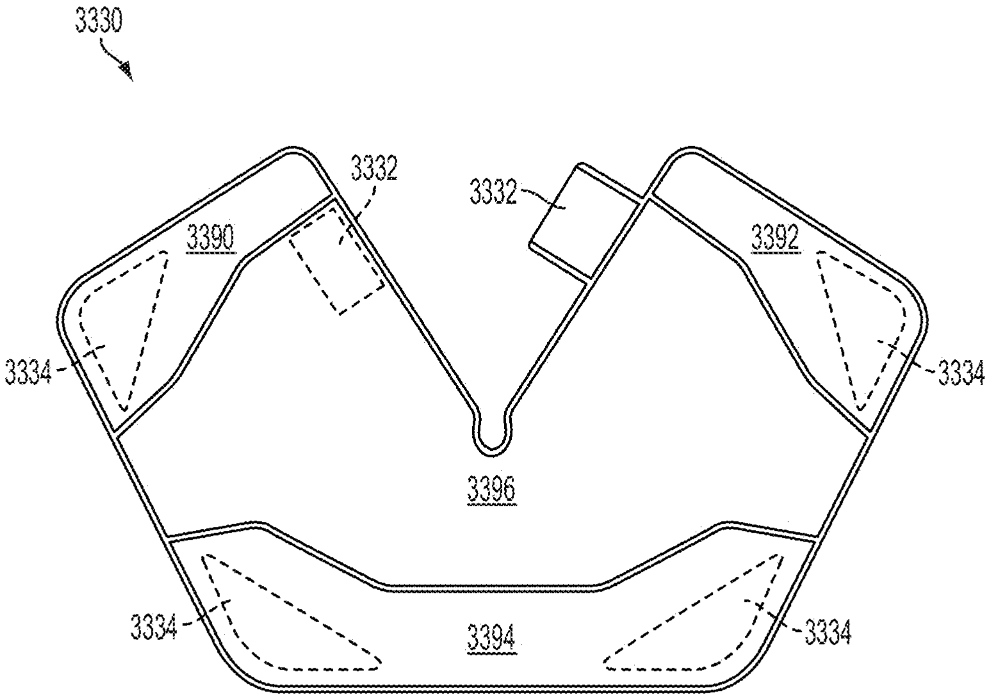

For the representative device and components thereof for the knee, FIG. 33A illustrates the components for the outside facing surface of the first segment 3320 showing representative locations for the inlet 3346 (for positioning the fill port 3335 on the bladder), extensions 3322, and securing elements 3375 for securing the extensions, and securing elements 3334 (e.g., hook) for securing the second element. FIG. 33B illustrates components for the inside facing surface of the first segment 3320, showing representative locations for means for securing elements 3375 (e.g., loops) for mating and securing with complementary elements from the outside facing surface. The three components X, Y, and Z of FIG. 33A are sewn or otherwise adhered together, so that the inner component X is permanently affixed and joined with the two outer components Y and Z, and said outer components may include further stitching at 3344 (e.g., gathering), so that the overall shape conforms to the shape of a knee. Similarly, the three components X', Y' and Z' of FIG. 33B are sewn or otherwise adhered together, so that the inner component X' is permanently affixed and joined with the two outer components Y' and Z', and said outer components may include further stitching at 3344 (e.g., gathering), so that when finally formed, the inside facing surface is compatible with and conforms with the shape of the outside facing surface when it is fully formed. Upon fully forming the outside facing surface and fully forming the inside facing surface, the inside and outside facing surfaces depicted in FIGS. 33A-33B are sewn or otherwise adhered together at or near its outermost edges (e.g., at or near its periphery), thereby forming an interior space therein, and so that the outside facing surface is an exterior surface when positioned for use and the inside facing is an interior surface of the first segment when positioned for use. In the embodiment of FIG. 33C, the bladder is configured into compartments 3336, 3336', 3337, 3338, 3338', 3339, and 3339', such that with fluid entering fill port 3335, compartment 3336 and then 3336' will fill first, followed by compartment 3337 and then compartments 3338, 3339, 3338' and 3339'. At various locations, a filler material 3355, e.g., a porous material or foam, may be included between compartments of the bladder allowing fluid flow there between. The filler material assists in maintaining an opening between compartments and is positioned either near a space provided along a seam line formed between compartments or is positioned within a large or irregular shaped compartment to prevent collapsing and ensure proper filling of the compartment. FIG. 33D shows a fill port 3335. In the embodiment of FIG. 33E, the second segment or leakproof element 3330 is configured with four compartments, 3390, 3392, 3394, and 3396. Said compartments, in this embodiment, are filled with varying amounts of the temperature sensitive component. Compartment 3396 will contain the most amount (in total) of the temperature sensitive component, compartment 3394 will contain an amount of the temperature sensitive component that is less than the amount in compartment 3396, and compartments 3390 and 3392 will have even less of the temperature sensitive component than the amount in compartment 3394. In one example, compartment 3396 contains about 400 grams of the temperature sensitive component, compartment 3394 contains about 100 grams of the temperature sensitive component, and compartments 3390 and 3392 each contain about 40 grams of the temperature sensitive component. More of the temperature sensitive component provides more of a temperature change in that compartment and more of the temperature sensitive component means the temperature at a first state is maintained for a longer period of time before returning back to its second state. The second segment 3330 is optional. It will further comprises securing elements 3334 in suitable positions for securing and mating with and capable of detaching from the inside facing surface of first segment 3320. As is shown, the number and size of the compartments in the second segment overlap in part with compartments in the bladder but are not in the exact same locations or the exact same overall shape and size. In addition mating couplers 3332 are positioned as indicated for shaping the second segment in order for it to conform with the shape of the first segment and with the knee. As with all securing elements and couplers described herein, a portion of each mating coupler, as well as a portion of each securing element on the first segment and the second segment will be permanently affixed to or adhered to the said segment while another portion will be for removable mating (allowing attachment and detachment) with its compatible coupler, or compatible securing element. Heat sealing or other permanent adherence known in the art is used for permanence.

Figure 34A:
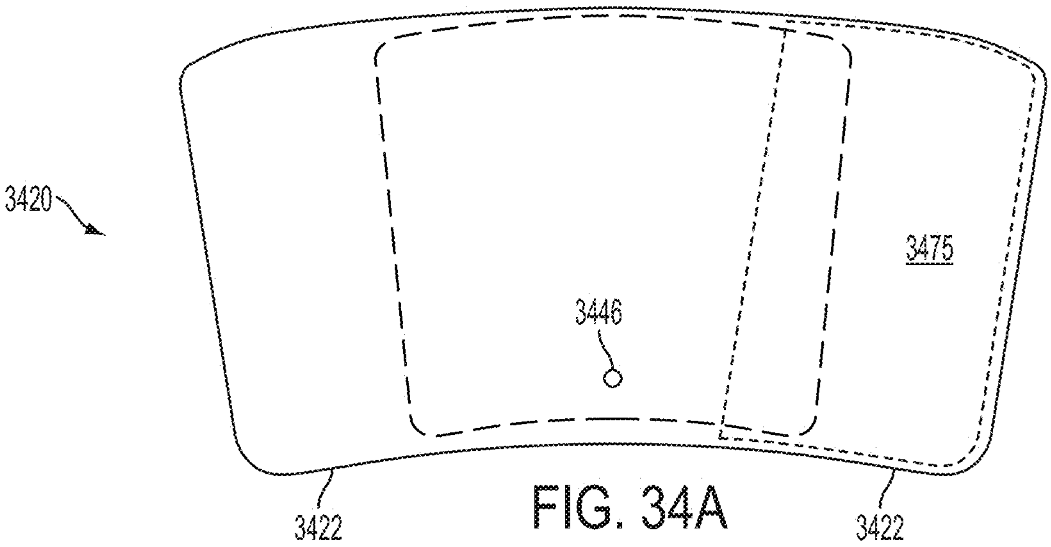
FIGS. 34A-34F depict representative device and components thereof for positioning on a portion of the body, such as the leg.
Figure 34B:
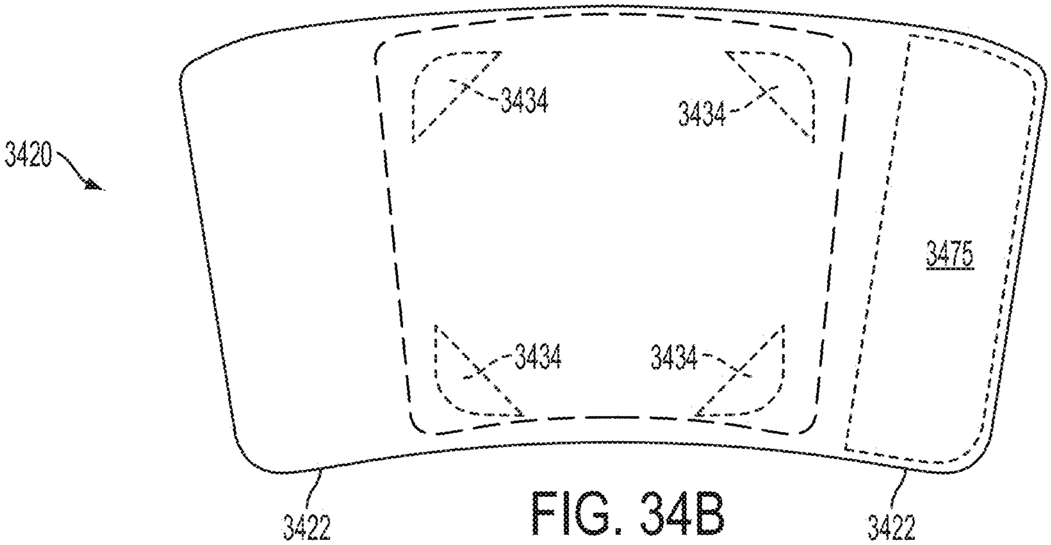
Figure 34C:
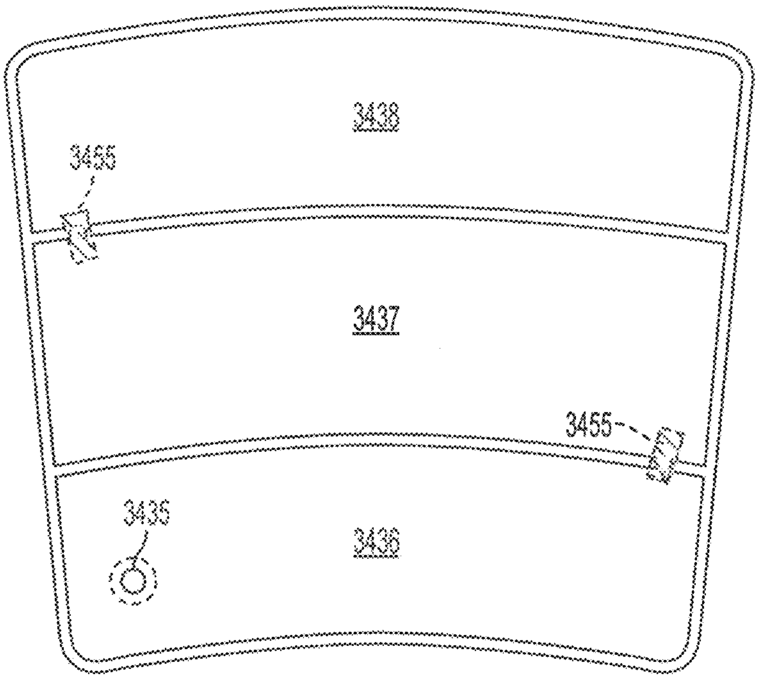
Figure 34D:
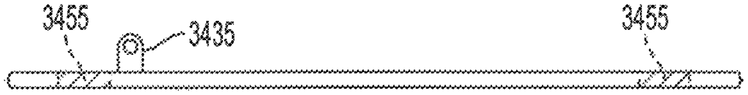
Figure 34E:
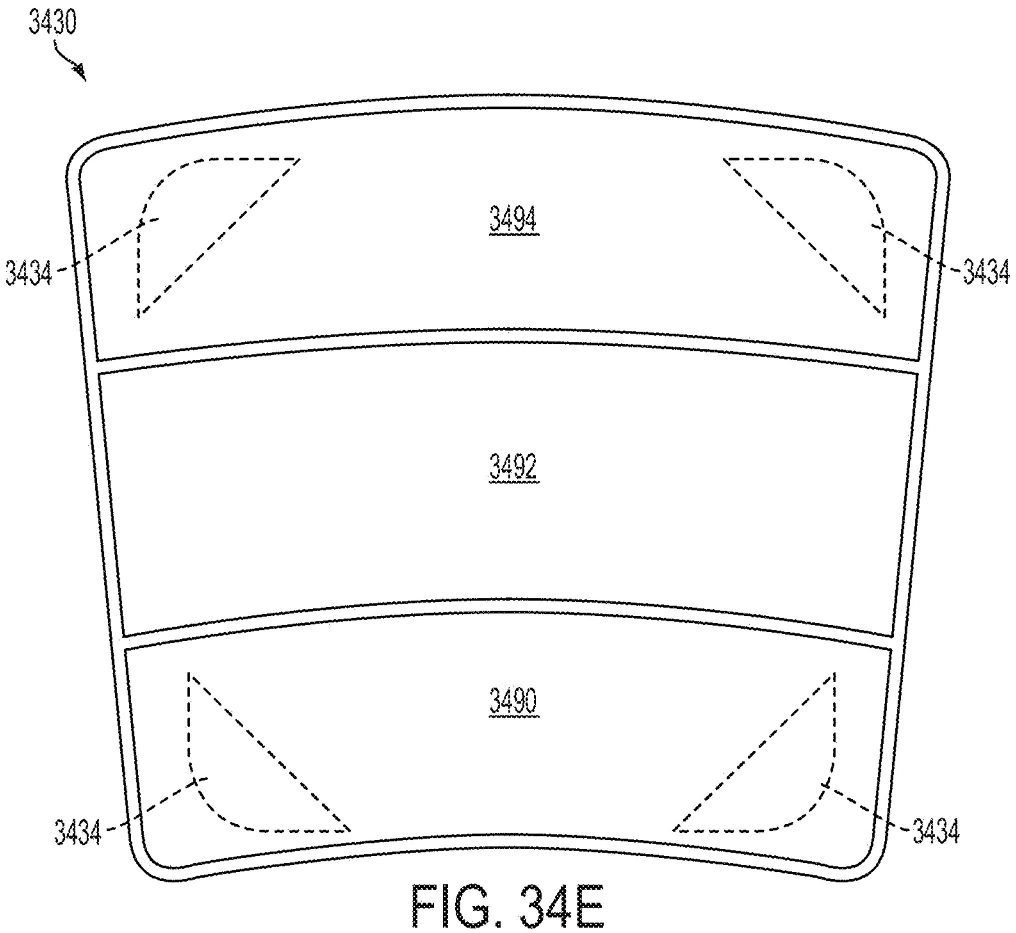
Figure 34F:
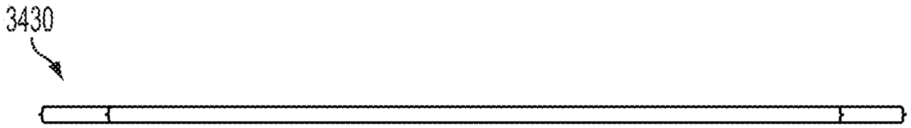

For the representative device and components thereof for the leg, FIG. 34A illustrates the outside facing surface of the first segment 3420 with representative locations for the inlet 3446 (for positioning the fill port 3435 on the bladder), extensions 3422, and securing elements 3475 (e.g., hook) for mating and securing with a compatible securing element 3475 on the inside facing surface as depicted in FIG. 34B. FIG. 34B illustrates the inside facing surface of the first segment 3420, showing representative locations for securing elements 3475 (e.g., loop) for mating and securing with the compatible securing element 3475 on the outside facing surface as depicted in FIG. 34A. Securing elements 3434 may be included with the inside facing surface of the first segment when desiring to secure an optional (and removable) second segment to the first segment. The inside and outside facing surfaces depicted in FIGS. 34A-34B are sewn or otherwise adhered together at or near its outermost edges (e.g., at or near its periphery), thereby forming an interior space, and so that the outside facing surface is an exterior surface when positioned for use and the inside facing is an interior surface of the first segment when positioned for use. The long dashed lines in FIG. 34A illustrate the relative position for the bladder. The long dashed lines in FIG. 34B illustrate the relative position for the second segment, when included. In the embodiment of FIG. 34C, the bladder is configured into three compartments 3436, 3437 and 3438, such that with fluid entering fill port 3435, compartment 3436 will fill first, followed by compartment 3437 and then compartment 3438. At various locations, a filler material 3455, e.g., a porous material or foam, may be included between compartments for ensuring flow between compartments. The filler material assists in maintaining an opening between compartments and is generally positioned in a space provided along a seam line formed between compartments. FIG. 34D also shows a fill port 3435 and the filler materials 3455. FIG. 34E illustrates the front view of the optional second segment or leakproof element 3430 and FIG. 34F illustrates a side view. In the illustrated embodiment, the second segment (which is optional) is configured with three compartments, 3490, 3492 and 3496. Said compartments may be filled with a similar amount of the temperature sensitive component per unit area, or may have different amounts of the temperature sensitive component per unit area, as desired. In this embodiment, compartments for the second segment are each filled with approximately the same amount of the temperature sensitive component (e.g., a similar total amount in each compartment). In addition, compartments 3490, 3492 and 3494 are shown to be generally compatible with and will align with compartments of the bladder when the second segment is positioned for use. The second segment may also include a number of securing elements 3434 that are compatible with (for mating purposes) and generally align with the securing elements 3434, located on the first segment, on its inner facing surface. Securing elements will have a portion thereof that are heat sealed or otherwise securely and permanently adhered to the second segment.

Figure 35F:
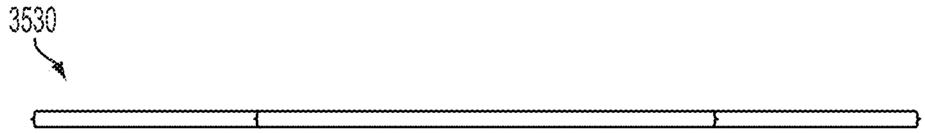

The representative device and components thereof for the shoulder shows an outside facing surface of the first segment 3520 with representative locations for the inlet 3546 (for positioning the fill port 3535 on the bladder), extensions 3522, and securing elements 3575 (e.g., as a hook on one extension and a loop on the mating extension). For FIG. 35A, the extensions wrap around the arm so that the inlet is positioned distally and outwardly on the upper arm (as shown in FIG. 35G, while the remaining portion of the outside facing surface is more proximal and near the shoulder. FIG. 35B depicts an additional portion of first segment 3520, showing its inside facing surface, with extensions 3522, securing elements 3575 (e.g., loops for the upper elements and hook for the lower element) for securing and mating, and securing elements 3534, which are for securing and mating with the second segment when used. FIGS. 35A and B are sewn or otherwise adhered together so that the proximal end of the segment depicted in FIG. 35A is fitted to the arch of the segment of FIG. 35B, thereby providing a one-sleeve like configuration (see. FIG. 35G). In FIG. 35C, the bladder is configured with seam lines that have large spaces there between, thus, fluid entering fill port 3535 will freely flow, therefore filling from the distal end to the proximal end. A filler material 3555, e.g., a porous material or foam, may be included with the bladder to assist in a more uniform flow in the proximal end. The filler material assists in maintaining an opening between compartments and may be positioned near a number of seam line that meet, with gaps formed where said meeting seam lines meet to assist in fluid flow. FIG. 35D also shows a fill port 3535 and the filler material 3555. FIG. 35E illustrates the front view of the optional second segment or leakproof element 3530 and FIG. 35F illustrates a side view. In the illustrated embodiment, the second segment is configured with four compartments, 3590, 3592, 3594 and 3596 with different total amounts of the temperature sensitive component. The back facing side of second segment 3530 (not shown) will have securing elements that mate with those on the inside facing surface of first segment 3520 depicted in FIG. 35B, mating with securing elements 3534, for allowing attachment and detachment of the second segment from the first segment. These securing elements, as with many of the other securing elements, will have a portion that is heat sealed or otherwise securely and permanently adhered to the second segment.

Figure 36A:
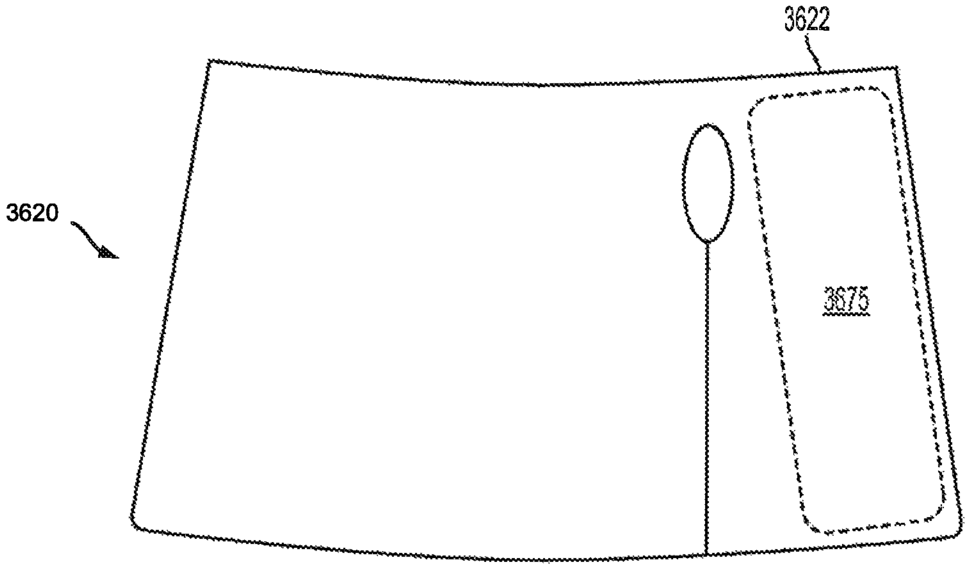
FIGS. 36A-36F depict representative device and components thereof for positioning on a portion of the body, such as the wrist.
Figure 36B:
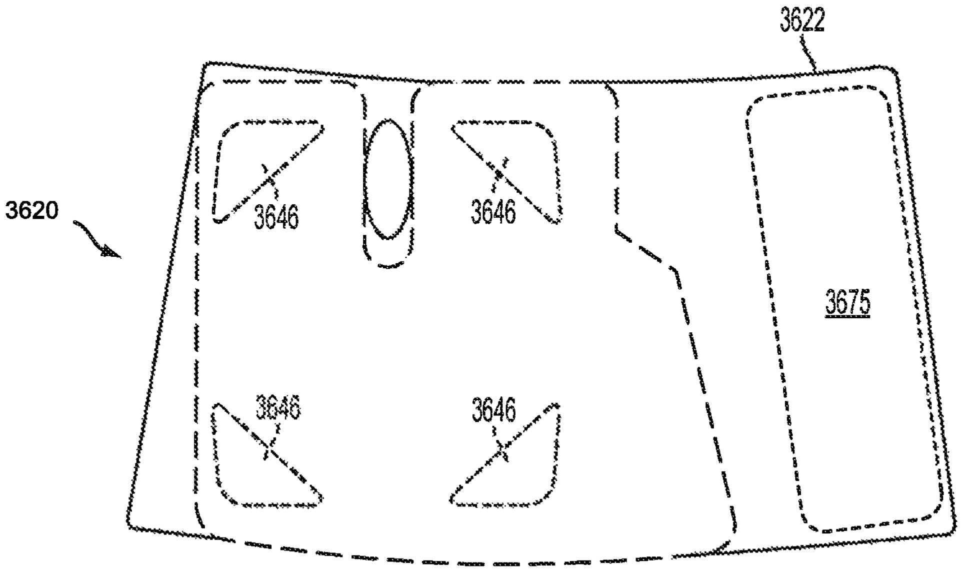
Figure 36C:
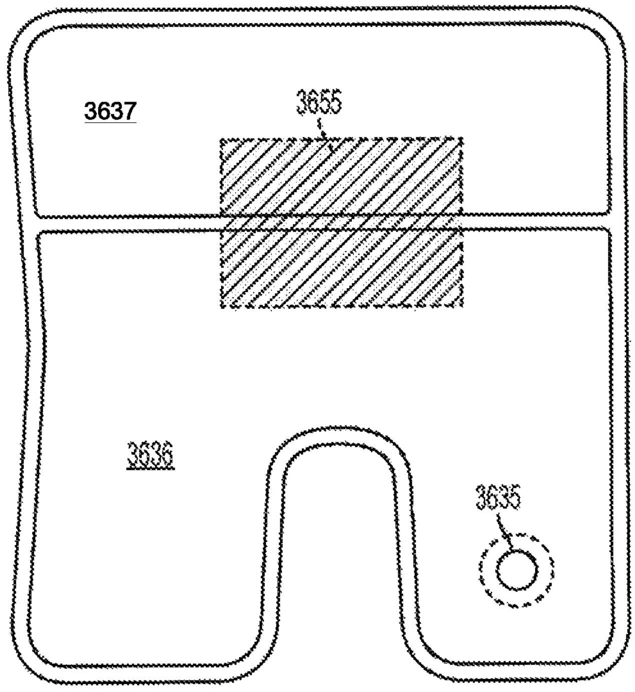
Figure 36D:
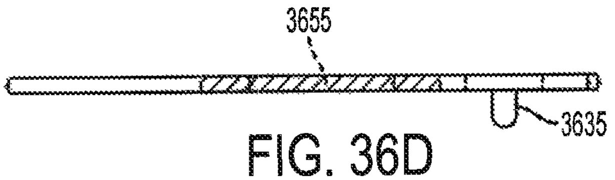
Figure 36E:
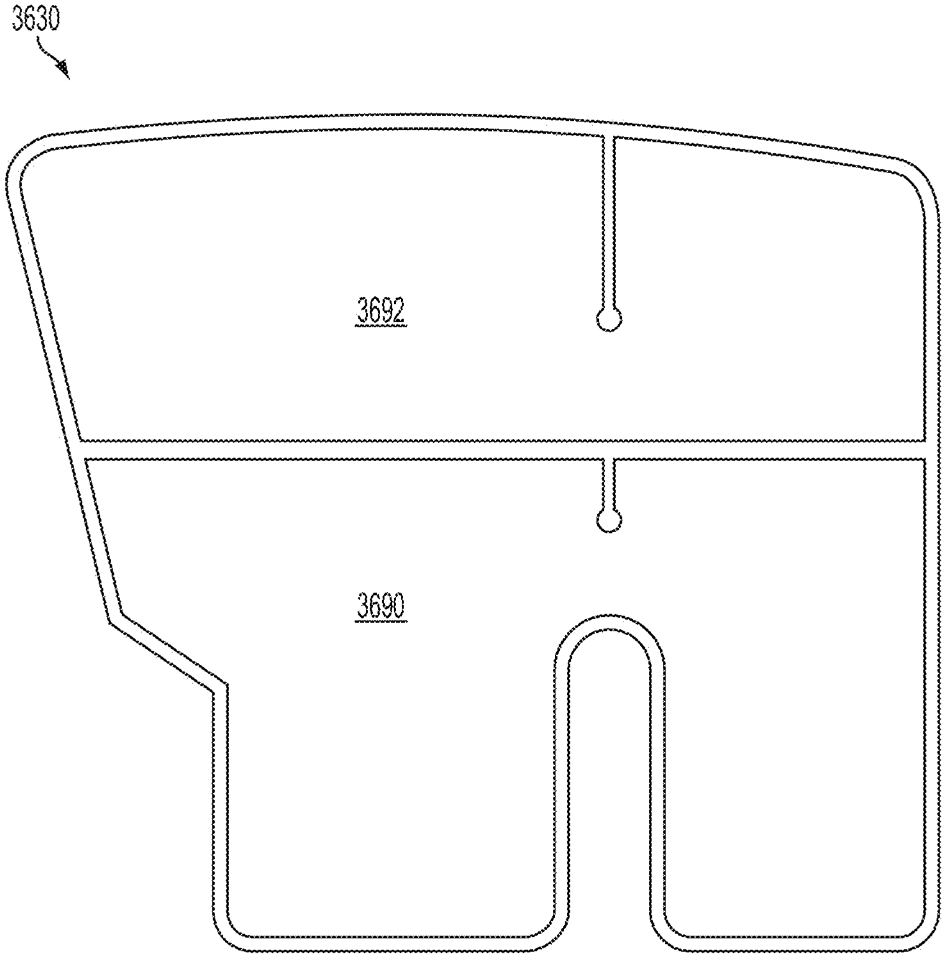
Figure 36F:
Figure 36G:
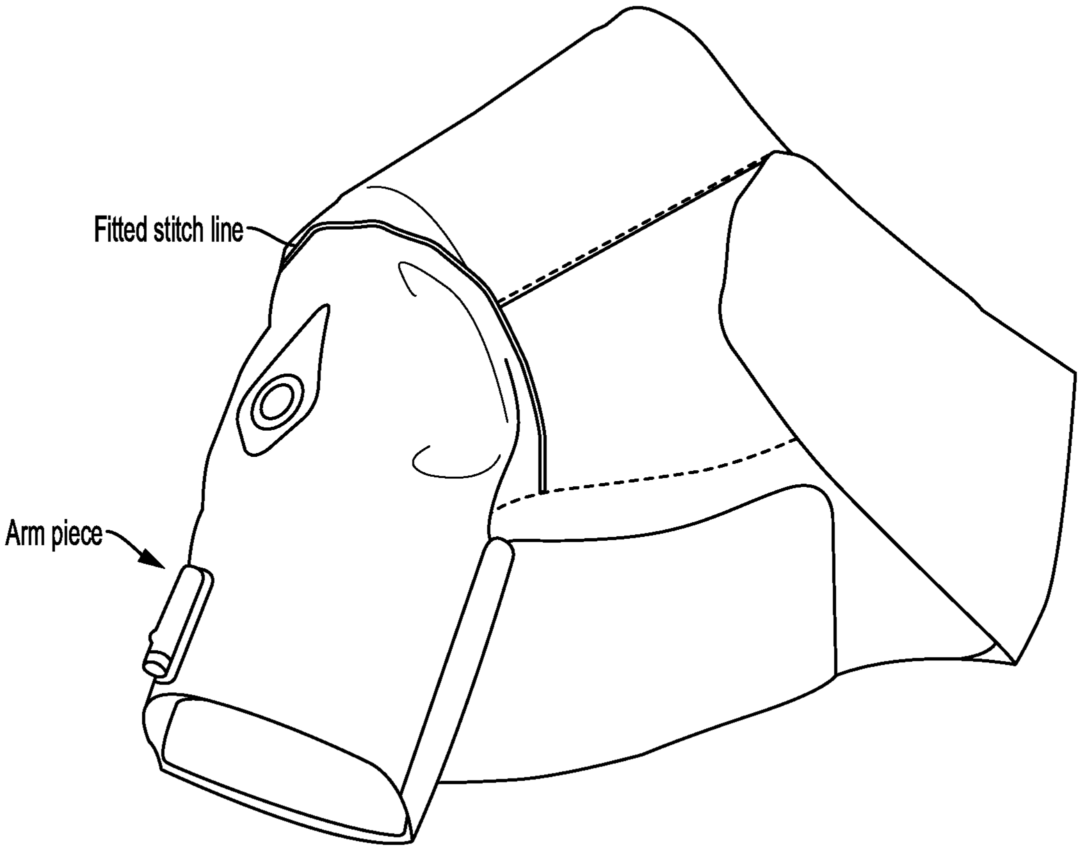
FIG. 36G depicts an example of the device of FIGS. 35A-35F when formed as if it were positioned for use on a shoulder.

Referring to the representative device and components thereof for the wrist, FIG. 36A illustrates the outside facing surface of the first segment 3620 with representative locations for the inlet 3646 (for positioning the fill port 3635 on the bladder), extensions 3622, and securing element 3675 (e.g., hooks) for securing and mating with a compatible securing element 3675 on the inside facing surface depicted in FIG. 36B. FIG. 36B illustrates the inside facing surface of the first segment 3620, showing representative locations for the securing element 3675 (e.g., loops) that mate and secure with the compatible securing element 3675 on the outside facing surface depicted in FIG. 36A. Securing elements 3646 may be included when the first segment is prepared for fitting with and for securing to an optional (and removable) second segment. FIG. 36A also shows a cutout region that assists when shaping (e.g., encircling) the first segment since the wrist is narrower than a more proximal portion of the arm. The long dashed lines in FIG. 36B illustrate the relative position for the second segment, when included. The inside and outside facing surfaces depicted in FIGS. 36A-36B are sewn or otherwise adhered together generally at or near its outermost edges (e.g., at or near its periphery), thereby forming an interior space, and so that the outside facing surface is an exterior surface when positioned for use and the inside facing is an interior surface of the first segment when positioned for use. In FIG. 36C, the bladder is configured into two compartments or chambers 3636, and 3637, such that with fluid entering fill port 3635 located near the distal portion, fills compartment 3636 first, followed by 3637. A filler material 3655, e.g., a porous material or a foam, may be included with the bladder for ensuring more uniform filling on the proximal end. FIG. 36D also shows a fill port 3635 and the filler material 3655. The filler material assists in maintaining an opening between compartments and is positioned either near a space provided along a seam line formed between compartments or is positioned where there is continuity between larger compartments to prevent collapse and to ensure proper filling of the compartments. FIG. 36E illustrates the front view of the optional second segment or leakproof element 3630 and FIG. 34F illustrates a side view. In the illustrated embodiment, the second segment is configured with two compartments, 3690 and 3692. Said compartments may be filled with a similar amount of the temperature sensitive component per unit area, or may have different amounts of the temperature sensitive component per unit area. In one example, the amounts of the temperature sensitive component are about the same in each compartment. The back facing side of second segment 3630 (not shown) will have securing elements that mate with those on the inside facing surface of first segment 3620 depicted in FIG. 36B, mating with securing elements 3634, to allow attachment and detachment of the second segment from the first segment. These securing elements, as with many of the other securing elements, will have a portion that is heat sealed or otherwise securely and permanently adhered to the second segment.

It is understood that alternative designs may be readily contemplated for the fluid source, first segment, extension elements, bladder, and temperature sensitive component housed in a second segment, each of which may be of many alternative sizes and configurations.

Thus, as described, are devices that deliver sequential and intermittent compression to one or more anatomic sites on a person. The device takes advantage of achieving a more uniform temperature and faster temperature adjustment to the anatomic site of interest as well as providing consistent temperature changes by including one or more of the following: using a temperature sensitive component that is malleable and has a freezing temperature that is below that of water, preferably with a long hysteresis; an inflatable bladder uniquely designed to provide compression site specifically and generally uniformly to the temperature sensitive component; a temperature sensitive component in a housing that is compartmentalized to prevent migration of the temperature sensitive component; an inflatable bladder that is generally in a similar size and shape or slightly larger than the housing for the temperature sensitive component; a housing for a temperature sensitive component that includes compartments in a configuration that is often similar to compartments in the bladder; ergonomically shaped extensions or straps (e.g., with curvatures) that prevent movement or migration of the extensions, particularly movement to a sensitive portion of the body; and the use of a time adjusted compression system that allows a user to achieve the same temperature efficacy with different pressures Although representative devices, components and methods of use have been described in detail herein, those skilled in the art will recognize that various substitutions and modifications that may be made without departing from what is described and shown as well as defined by the appended claims.

What is claimed is:

1. An apparatus for compressing at a site of a person in need thereof, the apparatus comprising:

- a portable control unit;
- a segment having a body with a distal end and a proximal end, when the apparatus is placed on the site of the person, an interior space within the body, an inlet to the body located at the distal end for access into the interior space, and one or more extending regions for securing the body at the site;
- an inflatable bladder with a distal end and a proximal end, when the apparatus is placed on the site of the person, one or more compartments and a fluid inlet port at the distal end of the inflatable bladder, the inflatable bladder adapted for intermittent inflation by a fluid from a fluid source under control of the portable control unit and positioned within the interior space of the body;
- a leakproof element containing a temperature sensitive material for cooling the site, the leakproof element having a plurality of sealed compartments adjacent to each other to prevent migration of the temperature sensitive material, wherein at least one of the plurality of sealed compartments has a larger amount or volume of the temperature sensitive material than the others, the leakproof element having coupling elements for detaching and attaching to a portion of the body of the segment; and
- wherein the portable control unit has one or more predefined algorithms that, when the control unit executes the one or more predefined algorithms, cause the apparatus to cool the site and to move the fluid from the distal end to the proximal end of the inflatable bladder in a direction towards a heart of the person by adjusting one or more of fluid pressure and period of inflation associated with the inflatable bladder.

2. The apparatus of claim 1, wherein the inflatable bladder has one compartment.

3. The apparatus of claim 1, wherein the inflatable bladder has more than one compartment.

4. The apparatus of claim 3, wherein the inflatable bladder has a seam between compartments and comprises a filler material positioned where there is a gap in the seam.

5. The apparatus of claim 1, wherein the portable control unit has the one or more predefined algorithms for, when the apparatus is placed on the site, achieving a temperature on the site by adjusting one or more of fluid pressure and period of inflation associated with the inflatable bladder and wherein the temperature on the site is less than 60° F.

6. The apparatus of claim 1, wherein the one or more extending regions are secured by one or more securing elements.

7. The apparatus of claim 1, wherein the one or more extending regions are secured by one or more attachable and detachable securing elements and when secured help prevent movement of the apparatus during operation.

8. The apparatus of claim 1, further comprising a portable fluid source for inflating the inflatable bladder.

9. The apparatus of claim 1, wherein the fluid inlet port of the inflatable bladder exits the inlet of the segment.

10. The apparatus of claim 1, wherein the inflatable bladder and the leakproof element are approximately the same overall size with respect to a front view of each.

11. The apparatus of claim 1, wherein the inflatable bladder is of a larger size than the leakproof element with respect to a front view of each.

12. The apparatus of claim 1, wherein the inflatable bladder and the leakproof element comprise the same number of compartments.

13. The apparatus of claim 1, wherein in operation the inflatable bladder inflates from the distal end to a proximal end.

14. A method of providing an apparatus for compressing at a site in need thereof, the method comprising:

- providing a portable control unit;
- providing a segment having a body with a distal end and a proximal end when the apparatus is placed on the site, an interior space within the body, an inlet to the body located at the distal end for access into the interior space, and one or more extending regions;
- positioning an inflatable bladder with a distal end and a proximal end when the apparatus is placed on the site, the inflatable bladder adapted for intermittent inflation by a fluid from a fluid source under control of the portable control unit in the interior space of the body with a fluid port at the distal end of the bladder extending from the inflatable bladder exiting the inlet of the segment;
- enclosing the inflatable bladder by securing the body along the body's periphery while the inflatable bladder remains within the interior space of the body;
- attaching a leakproof element containing a temperature sensitive material to an exterior portion of the body so that the leakproof element is cooperative with the inflatable bladder, the leakproof element having a plurality of sealed compartments adjacent to each other to prevent migration of the temperature sensitive material, wherein at least one of the plurality of sealed compartments has a larger amount or volume of the temperature sensitive material than the others; and
- wherein the portable control unit has one or more predefined algorithms that, when the control unit executes the one or more predefined algorithms, cause the apparatus to cool the site and to move the fluid from a distal end to a proximal end of the inflatable bladder by adjusting one or more of fluid pressure and period of inflation associated with the inflatable bladder.

15. The method of claim 14, wherein the leakproof element is detachable from the body.

16. The method of claim 14, wherein the enclosing of the inflatable body is reversible.

17. The method of claim 14, wherein the control unit has the one or more predefined algorithms for, when the apparatus is placed on the site, achieving a temperature on the site by adjusting one or more of fluid pressure and period of inflation associated with the inflatable bladder and wherein the temperature on the body site is at least 15° F. cooler than an initial temperature on the site.

18. An apparatus configured for placement on a person at a body site, the apparatus comprising:

a first segment housing a fluid chamber with a distal end and a proximal end, when the apparatus is placed on the body site of the person, the first segment fluidly coupled to a portable control unit, the fluid chamber adapted for intermittent inflation by a fluid from a fluid source and intermittent deflation of the fluid, and the fluid chamber adapted to inflate from the distal end to the proximal end;

a second segment removably coupled to the first segment to receive intermittent compression from the first segment, the second segment housing a temperature sensitive material, wherein the second segment is compartmentalized into a plurality of sealed compartments adjacent to each other to prevent migration of the temperature sensitive material, and wherein each of the plurality of compartments are separate such that the temperature sensitive material cannot migrate between each of the plurality of compartments;

wherein the portable control unit has a predefined algorithm that, when the control unit executes the predefined algorithm, cause the apparatus to cool the body site and to move the fluid from the distal end to the proximal end of the fluid chamber in a direction towards a heart of the person by adjusting one or both of a fluid pressure and a period of inflation associated with the fluid chamber.

19. The apparatus of claim 18, wherein the temperature sensitive material includes a chemical indicator.

20. The apparatus of claim 18, wherein the temperature sensitive material is a hydrogel.

21. The apparatus of claim 18, wherein the first segment is shaped for positioning about a joint.

22. The apparatus of claim 18 further comprising one or more fasteners cooperating with and extending from the first segment for securing the first and second segments about the body site.

23. The apparatus of claim 18 further comprising one or more ergonomically positioned fasteners cooperative with and extending from the first segment for securing the first and second segments about the body site.

24. The apparatus of claim 18, wherein the fluid chamber is contained within the first segment.

25. The apparatus of claim 18, wherein housing for the temperature sensitive material and the fluid chamber are of a similar size in at least two dimensions such that the fluid chamber overlaps substantially all of the temperature sensitive material.

26. The apparatus of claim 18, wherein housing for temperature sensitive material and the fluid chamber each include the same number of compartments.

27. The apparatus of claim 26, wherein the temperature sensitive material is a hydrogel silica gel, hydroethyl cellulose, cellosize, propylene glycol or a slush powder.

28. The apparatus of claim 18, wherein the temperature sensitive material includes an antifreeze material.

29. The apparatus of claim 28, wherein the antifreeze material is propylene glycol, ethylene glycol, glycerol or sodium chloride.

30. The apparatus of claim 18, wherein the fluid pressure is from about 50 mmHg to about 90 mmHg, and the period of inflation is from about 15 seconds to about 60 seconds.

31. A therapy system for use with a body site of a person, the system comprising:

a first segment housing a fluid chamber with a distal end and a proximal end when the therapy system is placed on the body site of the person, the first segment fluidly coupled to a portable control unit, the fluid chamber adapted for sequential and intermittent inflation by a fluid from a fluid source and sequential and intermittent deflation of the fluid, and the fluid chamber adapted to inflate from the distal end to the proximal end;

a second segment removably coupled to the first segment to receive sequential and intermittent compression from the first segment, the second segment housing a temperature sensitive material, wherein the second segment is compartmentalized into a plurality of compartments adjacent to each other to prevent migration of the temperature sensitive material, and wherein each of the plurality of compartments are separate such that the temperature sensitive material cannot migrate between each of the plurality of compartments; and one or more extending members cooperating with and extending from the first segment for securing the first and second segments about the body site, wherein at least a portion of the one or more extending members are shaped curvilinearly to prevent their migration from an initial position.

32. The system of claim 31, wherein the fluid chamber is contained within the first segment.

33. The system of claim 31, wherein the fluid chamber overlaps substantially all of the temperature sensitive material to provide compression to substantially all of the temperature sensitive material.

34. The system of claim 31, wherein the portable control unit has one or more predefined algorithms for achieving a temperature on the body site by adjusting one or both of a fluid pressure and a period of inflation associated with the fluid chamber.

35. The system of claim 34, wherein the temperature on the body site is less than 60° F.

36. A method of introducing a therapy system on a person at a body site comprising:

providing the therapy system to only the body site, the therapy system comprising:

a first segment housing a fluid chamber with a distal end and a proximal end when the therapy system is placed on the body site of the person, the first segment fluidly coupled to a portable control unit, the fluid chamber adapted for intermittent inflation by a fluid from a fluid source and intermittent deflation of the fluid, and the fluid chamber adapted for inflation from the distal end to the proximal end;

a second segment removably coupled to the first segment to receive intermittent compression from the first segment, the second segment housing a first temperature sensitive material, wherein the second segment is compartmentalized into a plurality of compartments adjacent to each other to prevent migration of the temperature sensitive material, and wherein each of the plurality of compartments are separate such that the temperature sensitive material cannot migrate between each of the plurality of compartments;

one or more extending members cooperating with and extending from the first segment for securing the first and second segments about the body site;

introducing fluid intermittently to inflate the fluid chamber thereby intermittently compressing only the body site while maintaining the one or more extending members in their initial position; and moving the fluid from the distal end to the proximal end of the fluid chamber in a direction towards a heart of the person by adjusting one or both of a fluid pressure and a period of inflation associated with the fluid chamber.

37. The method of claim 36, wherein the fluid is a second temperature sensitive material.

38. The method of claim 36, wherein the fluid chamber is adapted for sequential and intermittent inflation by the fluid from the fluid source and sequential and intermittent deflation of the fluid, wherein the second segment is cooperative with the first segment to receive sequential and intermittent compression from the first segment, and wherein the sequential and intermittent compression is from a distal portion of the body site to a proximal portion of the body site.

* * * * *